(12) United States Patent
Andres et al.

(10) Patent No.: US 11,124,519 B2
(45) Date of Patent: Sep. 21, 2021

(54) COCRYSTAL FORMS OF ((1S,2S,4R)-4-{4-[(1S)- 2,3-DIHYDRO-1H-INDEN-1- YLAMINO]-7H-PYRROLO [2,3-D]PYRIMIDIN-7-YL}-2- HYDROXYCYCLOPENTYL) METHYL SULFAMATE, FORMULATIONS AND USES THEREOF

(71) Applicant: Millennium Pharmaceuticals, Inc., Cambridge, MA (US)

(72) Inventors: Patricia Andres, West Lafayette, IN (US); Sarah Bethune, Erie, CO (US); Marianne Langston, Waltham, MA (US); Debra L. Mazaik, Holliston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/648,893

(22) PCT Filed: Sep. 20, 2018

(86) PCT No.: PCT/US2018/051940
§ 371 (c)(1),
(2) Date: Mar. 19, 2020

(87) PCT Pub. No.: WO2019/060536
PCT Pub. Date: Mar. 28, 2019

(65) Prior Publication Data
US 2020/0277294 A1    Sep. 3, 2020

Related U.S. Application Data

(60) Provisional application No. 62/561,527, filed on Sep. 21, 2017.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .......................... C07D 487/04; A61K 31/519
USPC ...................................... 544/280; 514/265.1
See application file for complete search history.

(56) References Cited

U.S. PATENT DOCUMENTS

| | | |
|---|---|---|
| 8,207,177 B2 | 6/2012 | Langston et al. |
| 8,933,225 B2 | 1/2015 | Armitage et al. |
| 9,187,482 B2 | 11/2015 | Armitage et al. |
| 9,683,003 B2 | 6/2017 | Duffey et al. |
| 9,802,938 B2 | 10/2017 | Armitage et al. |
| 9,827,246 B2 | 11/2017 | Blakemore et al. |
| 9,962,386 B2 | 5/2018 | Duffey et al. |
| 10,016,427 B2 | 7/2018 | Armitage et al. |
| 10,335,410 B2 | 7/2019 | Duffey et al. |
| 10,662,477 B2 | 5/2020 | Blakemore et al. |
| 10,745,404 B2 | 8/2020 | Armitage et al. |
| 2006/0189636 A1 | 8/2006 | Critchley et al. |
| 2007/0191293 A1 | 8/2007 | Langston et al. |
| 2009/0036678 A1 | 2/2009 | Armitage et al. |
| 2011/0021544 A1 | 1/2011 | Armitage et al. |
| 2012/0258927 A1 | 10/2012 | Langston et al. |
| 2012/0258977 A1 | 10/2012 | Langston et al. |
| 2013/0289037 A1 | 10/2013 | Langston et al. |
| 2015/0030601 A1 | 1/2015 | Amidon et al. |
| 2015/0119410 A1 | 4/2015 | Benes et al. |
| 2015/0164901 A1 | 6/2015 | Rubin |

(Continued)

FOREIGN PATENT DOCUMENTS

| | | |
|---|---|---|
| WO | WO 2007092213 A2 | 8/2007 |
| WO | WO-2009/042013 A1 | 4/2009 |

(Continued)

OTHER PUBLICATIONS

Armitage, I., et al., "Process Development and GMP Production of a Potent NAE Inhibitor Pevonedistat," *Organic Process Research & Development*, 19 (9): 1299-1307, American Chemical Society, United States (Aug. 2015).

(Continued)

*Primary Examiner* — Jeffrey H Murray
(74) *Attorney, Agent, or Firm* — Sterne, Kessler, Goldstein & Fox P.L.L.C.

(57) ABSTRACT

The present invention is directed to cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate of formula (I). The invention is also directed to methods of making cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate of formula (I). The invention is also directed to the pharmaceutical use of a cocrystal form as an E1 activating enzyme inhibitor, as well as a pharmaceutical composition comprising a cocrystal form. The invention is further directed to a method of treatment comprising administering a cocrystal form of ((1S,2S,4R)-4-{4-[(1S)-2,3-dihydro-1H-inden-1-ylamino]-7H-pyrrolo [2,3-d]pyrimidin-7-yl}-2-hydroxycyclopentyl)methyl sulfamate of formula (I).

(I)

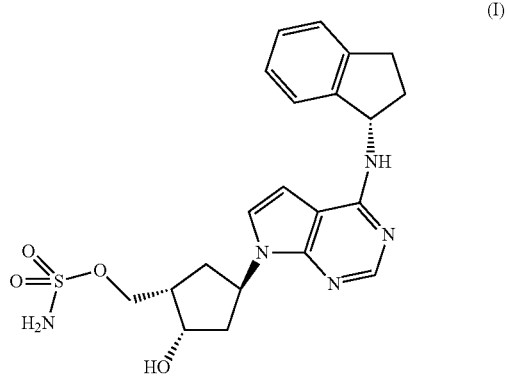

22 Claims, 30 Drawing Sheets

(56) References Cited

U.S. PATENT DOCUMENTS

| | | |
|---|---|---|
| 2016/0030432 A1 | 2/2016 | Armitage et al. |
| 2017/0105995 A1 | 4/2017 | Benes et al. |
| 2017/0107579 A1 | 4/2017 | Amidon et al. |
| 2017/0136024 A1 | 5/2017 | Langston et al. |
| 2019/0255052 A1 | 8/2019 | Langston et al. |
| 2020/0085821 A1 | 3/2020 | Duffey et al. |

FOREIGN PATENT DOCUMENTS

| | | |
|---|---|---|
| WO | WO-2010/132110 A1 | 11/2010 |
| WO | WO-2013/052814 A2 | 4/2013 |
| WO | WO-2013/063481 A1 | 5/2013 |
| WO | WO-2013/063496 A1 | 5/2013 |
| WO | WO-2014/055543 A2 | 4/2014 |
| WO | WO-2016/004136 A1 | 1/2016 |
| WO | WO 2019060536 A1 | 3/2019 |

OTHER PUBLICATIONS

Li, Y., et al., "Synthesis of two isotopically labeled versions of NEDD8-activating enzyme (NAE) inhibitor," *Tetrahedron Letters*, 52(15): 1807-1810, Elsevier, Netherlands (Apr. 2011).

Soucy, T.A., et al., An inhibitor of NEEDD8-activating enzyme as a new approach to treat cancer, *Nature*, 458: 732-737, Springer Nature Limited, Germany (Apr. 2009).

International Search Report and Written Opinion for International Application No. PCT/US18/51940, United States Patent Office, Alexandria, Virginia, dated Feb. 4, 2019, 28 pages.

COCRYSTAL FORMS OF ((1S,2S,4R)-4-{4-[(1S)-2,3-DIHYDRO-1H-INDEN-1-YLAMINO]-7H-PYRROLO [2,3-D] PYRIMIDIN-7-YL}-2-HYDROXYCYCLOPENTYL) METHYL SULFAMATE, FORMULATIONS AND USES THEREOF

This application claims benefit of U.S. Provisional Patent Application Ser. No. 62/561,527, filed on Sep. 21, 2017, which is hereby incorporated by reference in its entirety.

BACKGROUND OF THE INVENTION

Field of the Invention

The present invention relates to cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate of formula (I):

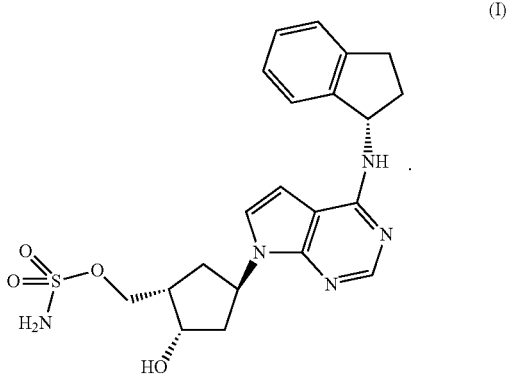 [SMILES: NS(=O)(=O)OC[C@@H]1C[C@@H](n2ccc3c(N[C@H]4CCc5ccccc54)ncnc32)C[C@@H]1O]

(I)

The invention is also directed to methods of making cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate of formula (I). The invention is also directed to the pharmaceutical use of a cocrystal form as an E1 activating enzyme inhibitor, as well as a pharmaceutical composition comprising a cocrystal form. The invention is further directed to a method of treatment comprising administering a cocrystal form of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate of formula (I).

Background Art

The post-translational modification of proteins by ubiquitin-like molecules (ubls) is an important regulatory process within cells, playing key roles in controlling many biological processes including cell division, cell signaling and the immune response. Ubls are small proteins that are covalently attached to a lysine on a target protein via an isopeptide linkage with a C-terminal glycine of the ubl. The ubiquitin-like molecule alters the molecular surface of the target protein and can affect such properties as protein-protein interactions, enzymatic activity, stability and cellular localization of the target.

Ubiquitin and other ubls are activated by a specific E1 enzyme which catalyzes the formation of an acyl-adenylate intermediate with the C-terminal glycine of the ubl. The activated ubl molecule is then transferred to the catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein.

Targeting E1 activating enzymes provides a unique opportunity to interfere with a variety of biochemical pathways important for maintaining the integrity of cell division and cell signaling. E1 activating enzymes function at the first step of ubl conjugation pathways; thus, inhibition of an E1 activating enzyme will specifically modulate the downstream biological consequences of the ubl modification. As such, inhibition of these activating enzymes, and the resultant inhibition of downstream effects of ubl-conjugation, represents a method of interfering with the integrity of cell division, cell signaling, and several aspects of cellular physiology which are important for disease mechanisms. Thus, E1 enzymes such as UAE, NAE, and SAE, as regulators of diverse cellular functions, are potentially important therapeutic targets for the identification of novel approaches to treatment of diseases and disorders.

Langston S. et al., Intl. App. Pub. No. WO 07/092213 and Langston S. et al, U.S. App. Pub. No. 2007/0191293, which are hereby incorporated by reference in their entirety, disclose compounds which are effective inhibitors of E1 activating enzymes, particularly NAE. The compounds are useful for inhibiting E1 activity in vitro and in vivo and are useful for the treatment of disorders of cell proliferation, particularly cancer, and other disorders associated with E1 activity. One class of compounds described in Langston et al. are 4-substituted ((1S, 2S, 4R)-2-hydroxy-4-{7H-pyrrolo [2,3-d]pyrimidin-7-yl}cyclopentyl)methyl sulfamates. Armitage I. et al., U.S. App. Pub. No. 2009/0036678, which is hereby incorporated by reference in its entirety, discloses methods for the preparation of ((1S, 2S, 4R)-2-hydroxy-4-{7H-pyrrolo[2,3-d]pyrimidin-7-yl}cyclopentyl)methyl sulfamates, including ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate. This compound has been reported to be a selective NAE inhibitor. See, e.g., Soucy, T. A., et al., *Nature*, 2009, 458, 732-737 (which refers to the compound as MLN4924).

These applications additionally disclose pharmaceutical compositions containing these compounds, and methods for the treatment or therapy of diseases, disorders, or conditions associated with E1 activating enzymes, particularly NAE, including proliferative diseases such as cancer.

((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I) is described is described in Intl. App. Pub. No. WO 07/092213, U.S. App. Pub. No. 2007/0191293, and U.S. App. Pub. No. 2009/0036678. The potassium salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I) is disclosed in WO 07/092213 and U.S. App. Pub. No. 2007/0191293.

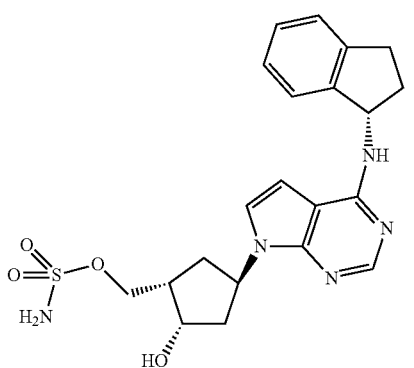

(I)

The large-scale manufacturing of a pharmaceutical composition poses many challenges to the chemist and chemical engineer. While many of these challenges relate to the handling of large quantities of reagents and control of large-scale reactions, the handling of the final product poses special challenges linked to the nature of the final active product itself. Not only must the product be prepared in high yield, be stable, and capable of ready isolation, the product must possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term formulation. Each of these steps may be impacted by various environmental conditions of temperature and humidity.

The pharmaceutically active substance used to prepare the pharmaceutical compositions should be as pure as possible and its stability on long-term storage must be guaranteed under various environmental conditions. These properties are absolutely essential to prevent the appearance of unintended degradation products in pharmaceutical compositions, which degradation products may be potentially toxic or result simply in reducing the potency of the composition.

A primary concern for the manufacture of large-scale pharmaceutical compounds is that the active substance should have a stable crystalline morphology to ensure consistent processing parameters and pharmaceutical quality. If an unstable crystalline form is used, crystal morphology may change during manufacture and/or storage resulting in quality control problems, and formulation irregularities. Such a change may affect the reproducibility of the manufacturing process and thus lead to final formulations which do not meet the high quality and stringent requirements imposed on formulations of pharmaceutical compositions. In this regard, it should be generally borne in mind that any change to the solid state of a pharmaceutical composition which can improve its physical and chemical stability gives a significant advantage over less stable forms of the same drug.

When a compound crystallizes from a solution or slurry, it may crystallize with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

As described generally above, the polymorphic behavior of drugs can be of great importance in pharmacy and pharmacology. The differences in physical properties exhibited by polymorphs affect practical parameters such as storage stability, compressibility and density (important in formulation and product manufacturing), and dissolution rates (an important factor in determining bio-availability). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to thermodynamically more stable polymorph) or both (e.g., tablets of one polymorph are more susceptible to breakdown at high humidity). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While drug formulations having improved chemical and physical properties are desired, there is no predictable means for preparing new drug forms (e.g., polymorphs) of existing molecules for such formulations. These new forms would provide consistency in physical properties over a range of environments common to manufacturing and composition usage. Thus, there is a need for new drug forms that are useful for inhibiting E1 activity in vitro and in vivo, and are useful for the treatment of disorders of cell proliferation, particularly cancer, and other disorders associated with E1 activity, as well as having properties suitable for large-scale manufacturing and formulation.

The hydrochloride salt of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I), crystalline forms thereof, solvates thereof, and methods of making them are described in U.S. Appl. Pub. No. 2011/0021544.

However, U.S. Appl. Pub. No. 2011/0021544 also disclosed that the above hydrochloride salt exhibits limited chemical stability during accelerated stress condition. Therefore, there is a need for new drug forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (1), including other salts, crystalline forms thereof, cocrystals, and solvates thereof.

BRIEF SUMMARY OF THE INVENTION

The present invention is directed to cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate of formula (I), also known as MLN4924 or TAK-924, and solvates thereof. These cocrystal forms have properties that are useful for large-scale manufacturing, pharmaceutical formulation, and storage. The invention is also directed to methods of making cocrystal forms of formula (I). The present invention is also directed to pharmaceutical compositions comprising these cocrystal forms and to methods of uses of these cocrystal forms for the treatment of a variety of diseases, disorders or conditions as described herein.

The present invention shall be more fully discussed with the aid of the following figures and detailed description below.

DETAILED DESCRIPTION OF THE INVENTION

Definitions and Abbreviations

Figure 1:
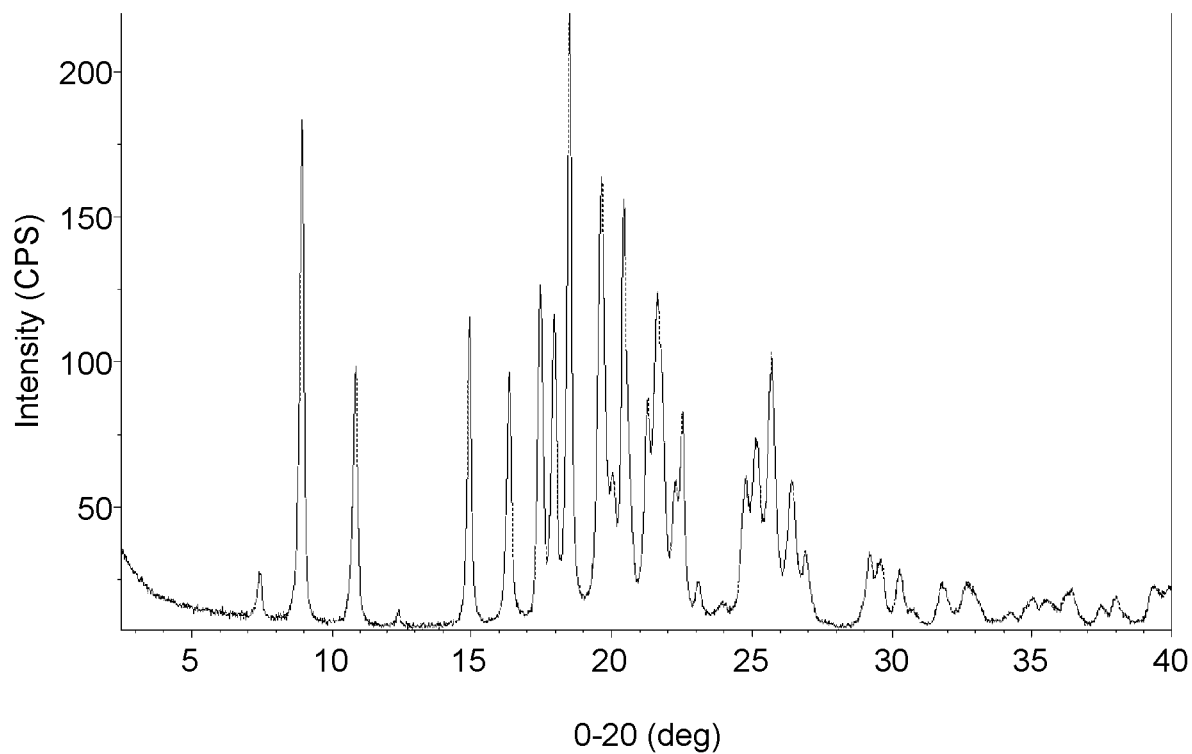
FIG. 1 is an XRPD pattern of cocrystal Form A which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and glycolic acid.

As used above, and throughout the description of the invention, the following terms, unless otherwise indicated, shall be understood to have the following meanings.

As used herein, "cocrystal" refers to a crystalline structure composed of at least two components in the same crystal lattice, where the components may be atoms, ions or molecules. Cocrystals consist of two or more components that form a unique crystalline structure having unique properties. Cocrystals can encompass hydrates, solvates and clathrates.

As used herein, "crystalline" and "crystalline form" refer to a solid having a highly regular chemical structure, including cocrystals. For the purposes of this application, the terms "crystalline form" and "polymorph" are synonymous; the terms distinguish between cocrystal forms that have different properties (e.g., different XRPD patterns, different DSC scan results).

The term "solvate" or "solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" or "solvated" encompasses both solution-phase and isolable solvates. Representative solvates include, for example, hydrates, ethanolates, and methanolates.

The term "mixture" refers to the combined elements of the mixture regardless of the phase-state of the combination (e.g., liquid or liquid/crystalline).

The term "seeding" refers to the addition of crystalline material to a solution or mixture to initiate crystallization.

Cocrystal Forms

In one aspect, the present invention is directed to cocrystal forms of the compound ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate or a solvate thereof. Accordingly, the present invention provides cocrystal forms of the compound of formula (I):

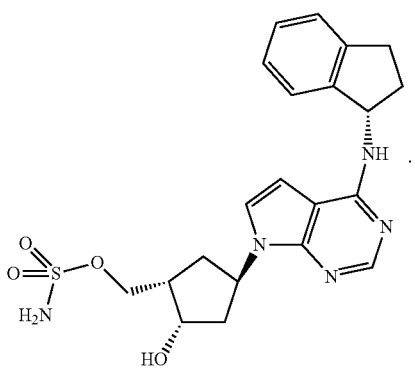
(I)

Provided herein is characterizing information to describe distinct cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I). It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a distinguishing peak can be sufficient for one skilled in the art to appreciate that such particular form is present.

Certain cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (1) have properties that make them suitable for large scale pharmaceutical formulation manufacture.

Embodiments are directed to cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I), wherein the particular cocrystal form (e.g., Form A, Form C) has at least a particular percentage of purity. In some embodiments, the cocrystal form (e.g., Form A, Form C) is at least 80% pure. In some embodiments, the cocrystal form (e.g., Form A, Form C) is at least 85% pure. In some embodiments, the cocrystal form (e.g., Form A, Form C) is at least 90% pure. In some embodiments, the cocrystal form (e.g., Form A, Form C) is at least 95% pure. In another embodiments, the cocrystal form (e.g., Form A, Form C) is substantially pure.

In the following description of the cocrystal forms of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate (I) (MLN4924), embodiments may be described with reference to a particular crystalline form of the cocrystals, as characterized by one or more properties as discussed herein. The descriptions characterizing the crystalline forms may also be used to describe the mixture of different crystalline forms that may be present in a cocrystal. However, the particular cocrystal may also be characterized by one or more of the characteristics of the polymorph as described herein, with or without regard to referencing a particular crystalline form.

Throughout the specification and claims, when a cocrystal form of MLN4924 is identified using one or more XRPD peaks given as angle 2θ, each of the 2θ values is understood to mean the given value±0.2 degrees.

Throughout the specification and claims, when a cocrystal form of MLN4924 is identified using one or more temperatures from a DSC and TGA profile (e.g., onset of endothermic transition, melt, etc.), each of the temperature values is understood to mean the given value±2° C.

In one embodiment, the present invention relates to a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate of formula (I) and a coformer, wherein the coformer is selected from organic acids, organic bases, and amino acids. In another embodiment, the coformer is selected from acetic acid, benzoic acid, camphoric acid, caproic acid, trans-cinnamic acid, ethylenediamine, fumaric acid, gentisic acid, D-glucuronic acid, glycolic acid, hippuric acid, DL-lactic acid, L-lysine, L-malic acid, malonic acid, DL-mandelic acid, meglumine, orotic acid, oxalic acid, piperazine, L-proline, L-pyroglutamic acid, saccharin, succinic acid, and vanillin. In another embodiment, the coformer is selected from hippuric acid, malonic acid, or saccharin.

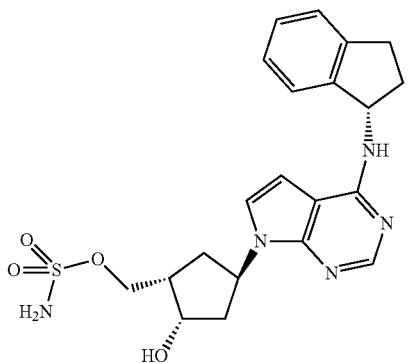

(I)

In one embodiment, the cocrystal is a cocrystal of ((1S, 2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and glycolic acid. In one embodiment, the cocrystal is an anhydrous mono-glycolic acid cocrystal.

In one embodiment, the cocrystal is characterized by an XRPD pattern having peaks at 2θ angles of 8.94°, 18.48°, and 20.41°+0.2°. In one embodiment, the cocrystal is characterized by an XRPD pattern having peaks at 2θ angles of 8.940, 14.94°, 18.48°, 19.62° and 20.41°±0.2°. In another embodiment, the cocrystal is characterized by an XRPD pattern as shown in FIG. 1.

FIG. 1 shows an X-ray powder diffraction (XRPD) pattern of cocrystal Form A obtained using Cu—Kα radiation. Peaks identified in FIG. 1 include those listed in Table 1.

TABLE 1

| Diffraction angle | d spacing (Å) |
|---|---|
| 8.94 ± 0.20 | 9.889 ± 0.226 |
| 10.85 ± 0.20 | 8.156 ± 0.153 |
| 14.94 ± 0.20 | 5.929 ± 0.080 |
| 16.35 ± 0.20 | 5.423 ± 0.067 |
| 17.46 ± 0.20 | 5.078 ± 0.058 |
| 17.95 ± 0.20 | 4.942 ± 0.055 |
| 18.48 ± 0.20 | 4.800 ± 0.052 |
| 19.62 ± 0.20 | 4.525 ± 0.046 |
| 20.41 ± 0.20 | 4.352 ± 0.043 |
| 21.26 ± 0.20 | 4.180 ± 0.039 |
| 21.59 ± 0.20 | 4.116 ± 0.038 |
| 21.79 ± 0.20 | 4.078 ± 0.037 |
| 22.26 ± 0.20 | 3.994 ± 0.036 |
| 22.50 ± 0.20 | 3.953 ± 0.035 |
| 24.73 ± 0.20 | 3.600 ± 0.029 |
| 25.12 ± 0.20 | 3.545 ± 0.028 |
| 25.69 ± 0.20 | 3.468 ± 0.027 |
| 26.42 ± 0.20 | 3.373 ± 0.025 |

Table 2 shows the unit cell parameters of the cocrystal derived from the corresponding indexed XRPD data. In one embodiment, the cocrystal exhibits crystal parameters that are approximately equal to the following: a=5.131 Å, b=9.969 Å, c=12.101 Å, α=82.01°, β=81260, γ=88,60°, volume=605.8 Å³/cell, and space group=P1 (1).

TABLE 2

| | MLN4924 glycolic acid |
|---|---|
| Bravais Type | Triclinic |
| a [Å] | 5.131 |
| b [Å] | 9.969 |

TABLE 2-continued

| | MLN4924 glycolic acid |
|---|---|
| c [Å] | 12.101 |
| α [deg] | 82.01 |
| β [deg] | 81.26 |
| γ [deg] | 88.60 |
| Volume [Å³/cell] | 605.8 |
| Chiral Contents ? | Chiral |
| Extinction Symbol | P - |
| Space Group(s) | P1 (1) |
| Source | Triads Algorithm |

Figure 2:
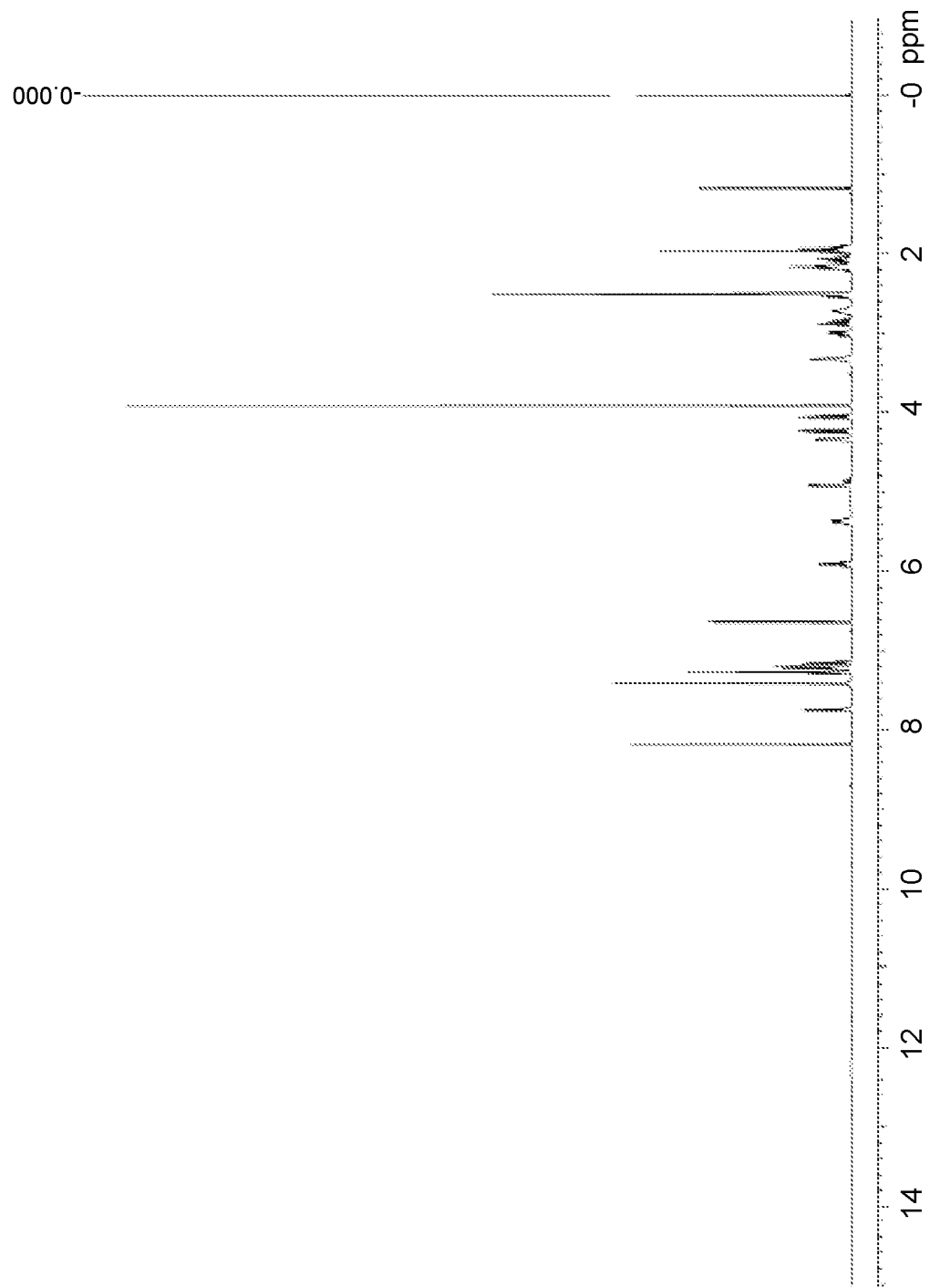
FIG. 2 is a ¹H-NMR of cocrystal Form A which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and glycolic acid.

FIG. 2 shows a ¹H-NMR of cocrystal Form A. The ¹H-NMR indicates that the stoichiometric ratio of MLN4924 to glycolic acid is 1:1 and cocrystal Form A is an anhydrous mono-glycolic acid cocrystal. In one embodiment, the cocrystal is characterized by a ¹H-NMR substantially similar to FIG. 2.

Figure 3:
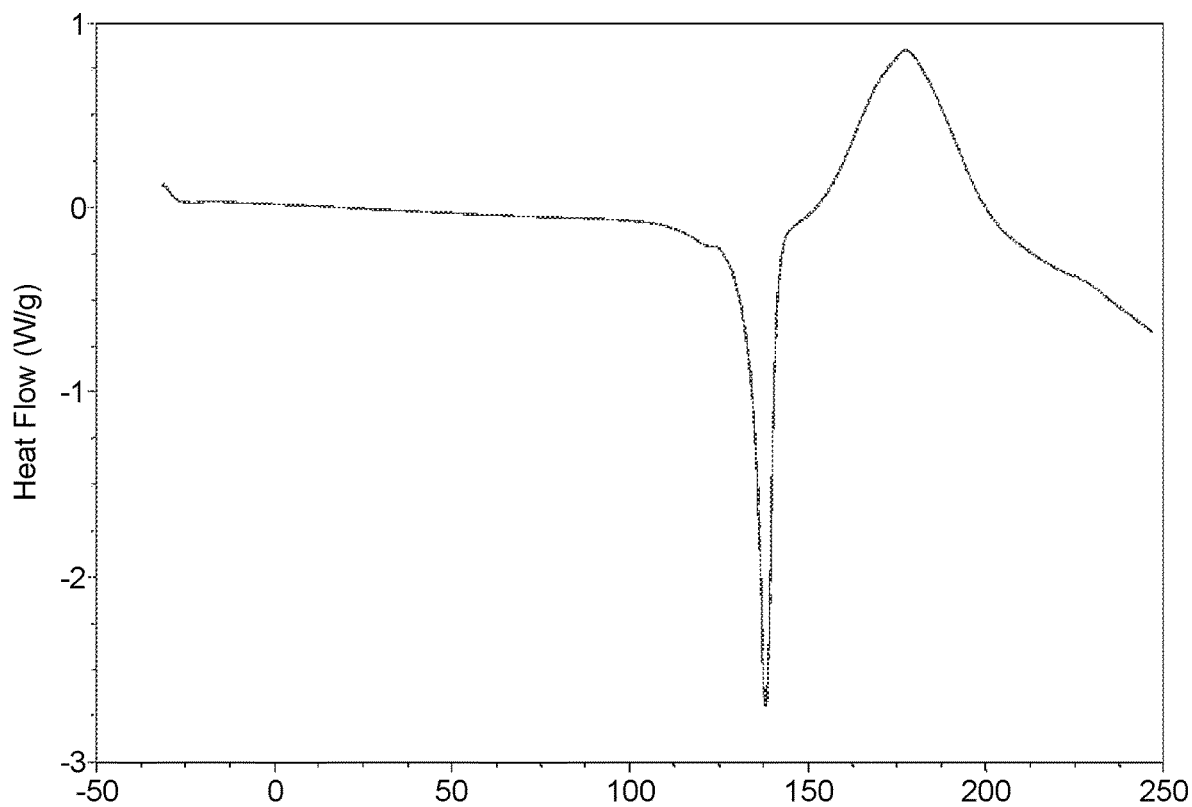
FIG. 3 is a differential scanning calorimetry (DSC) profile for cocrystal Form A which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and glycolic acid.

FIG. 3 shows a differential scanning calorimetry profile (DSC) of cocrystal Form A. The DSC graph plots the heat flow as a function of temperature from a sample, the temperature rate change being about 10° C./min. In one embodiment, the cocrystal is characterized by a DSC profile characterized by an endothermic peak at about 138.1° C. In another embodiment, the cocrystal is characterized by a DSC profile as shown in FIG. 3.

Figure 4:
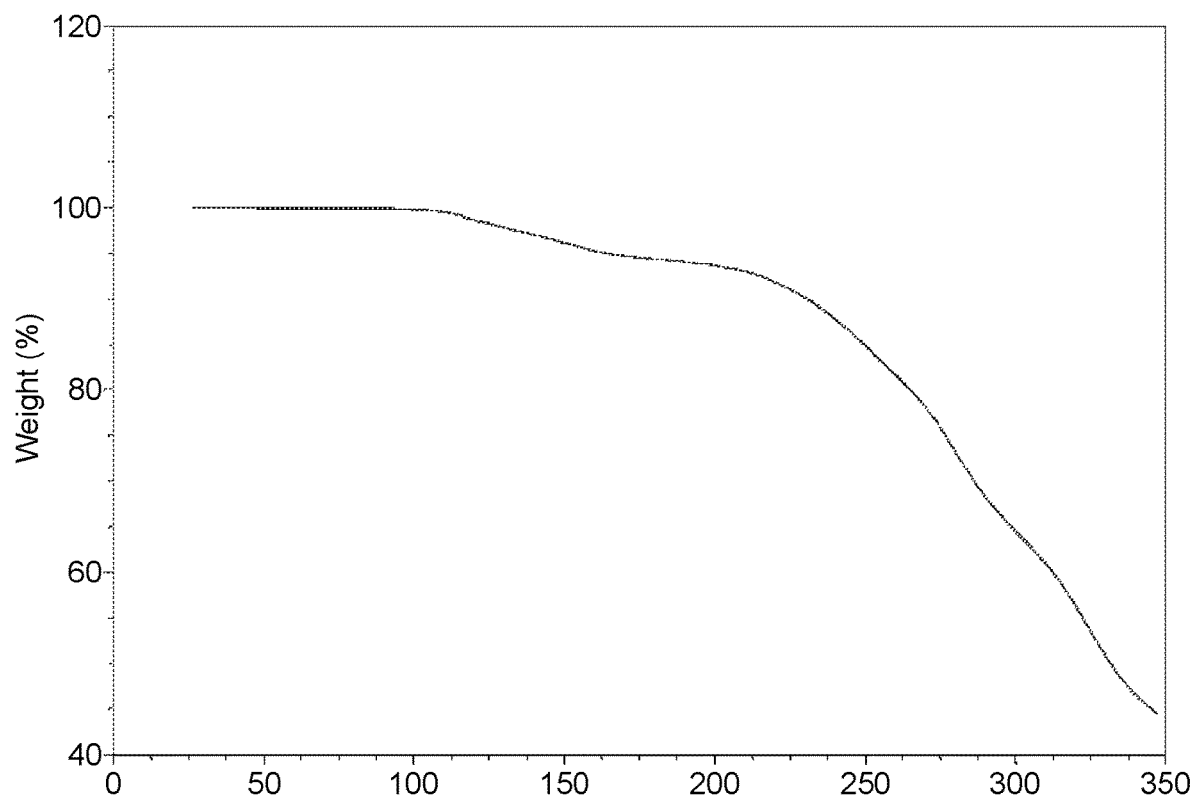
FIG. 4 is a thermal gravimetric analysis (TGA) profile for cocrystal Form A which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and glycolic acid.

FIG. 4 shows a thermal gravimetric analysis (TGA) profile of cocrystal Form A. The TGA profile plots the percent loss of weight of the sample as a function of temperature, the temperature rate change being about 10° C./min. In one embodiment, the cocrystal is characterized by a TGA characterized by an about 5.3 wt % loss between about 101° C. and about 175° C. and a weight loss at about 216° C. In another embodiment, the cocrystal is characterized by a TGA profile as shown in FIG. 4.

In one embodiment, the cocrystal is characterized by at least two of the following features (I-i)-(I-iv):
(I-i) an XRPD pattern having peaks at 2θ angles of 8.94°, 18.48°, and 20.41°±0.2°;
(I-ii) a ¹H-NMR substantially similar to FIG. 2;
(I-iii) a DSC profile as shown in FIG. 3; or
(I-iv) a TGA profile as shown in FIG. 4.

In one embodiment, the cocrystal is cocrystal Form A, which is characterized by one or more of the following features: an XRPD pattern as shown in FIG. 1, a ¹H-NMR substantially similar to FIG. 2, a DSC profile as shown in FIG. 3, or a TGA profile as shown in FIG. 4.

In one embodiment, the cocrystal is characterized by an XRPD pattern having peaks at 2θ angles of 5.10, 18.2°, and 21.7°±0.2°. In one embodiment, the cocrystal is characterized by an XRPD pattern having peaks at 2θ angles of 5.10, 16.30, 18.2°, 20.7°, and 21.7°±0.2°. In another embodiment, the cocrystal is characterized by an XRPD pattern as shown in FIG. 9.

Figure 9:
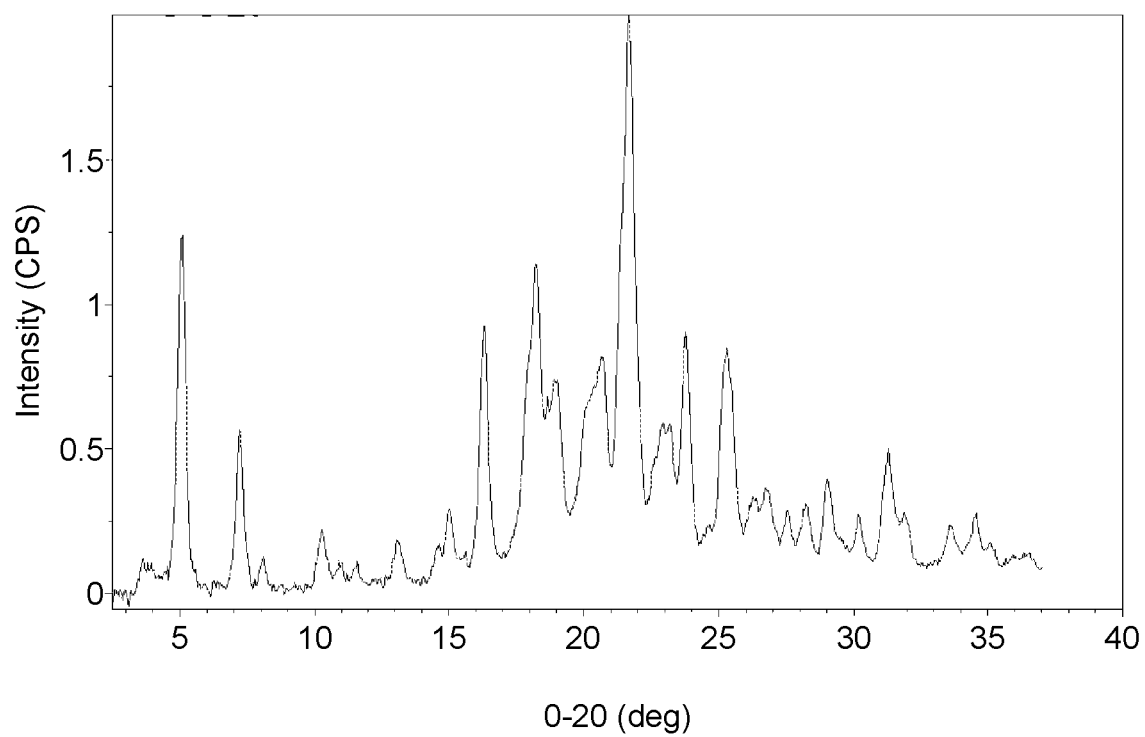
FIG. 9 is an XRPD pattern of cocrystal Form C which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and glycolic acid.

FIG. 9 shows an X-ray powder diffraction (XRPD) pattern of the cocrystal Form C obtained using Cu-Kα radiation. Peaks identified in FIG. 9 include those listed in Table 3.

TABLE 3

| Diffraction angle | d spacing (Å) |
|---|---|
| 3.6 ± 0.2 | 24.408 ± 1.427 |
| 5.1 ± 0.2 | 17.465 ± 0.718 |
| 7.2 ± 0.2 | 12.244 ± 0.348 |
| 8.1 ± 0.2 | 10.970 ± 0.279 |

TABLE 3-continued

| Diffraction angle | d spacing (Å) |
| --- | --- |
| 10.3 ± 0.2 | 8.622 ± 0.171 |
| 10.9 ± 0.2 | 8.117 ± 0.151 |
| 11.6 ± 0.2 | 7.642 ± 0.134 |
| 13.1 ± 0.2 | 6.758 ± 0.104 |
| 14.7 ± 0.2 | 6.043 ± 0.083 |
| 15.0 ± 0.2 | 5.899 ± 0.079 |
| 15.6 ± 0.2 | 5.673 ± 0.073 |
| 16.3 ± 0.2 | 5.438 ± 0.067 |
| 18.2 ± 0.2 | 4.869 ± 0.054 |
| 18.9 ± 0.2 | 4.686 ± 0.050 |
| 20.7 ± 0.2 | 4.291 ± 0.041 |
| 21.7 ± 0.2 | 4.103 ± 0.038 |
| 23.2 ± 0.2 | 3.837 ± 0.033 |
| 23.8 ± 0.2 | 3.742 ± 0.031 |
| 25.3 ± 0.2 | 3.520 ± 0.028 |
| 26.3 ± 0.2 | 3.384 ± 0.025 |
| 26.8 ± 0.2 | 3.329 ± 0.025 |
| 28.2 ± 0.2 | 3.162 ± 0.022 |
| 29.0 ± 0.2 | 3.077 ± 0.021 |

In one embodiment, the cocrystal is cocrystal Form C, which is characterized by an XRPD pattern as shown in FIG. 9.

In one embodiment, the cocrystal is a cocrystal of ((1S, 2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and hippuric acid. In one embodiment, the cocrystal is an anhydrous mono-hippuric acid cocrystal.

In one embodiment, the cocrystal is characterized by an XRPD pattern having peaks at 2θ angles of 4.05°, 19.24°, and 22.60°±0.2°. In one embodiment, the cocrystal is characterized by an XRPD pattern having peaks at 2θ angles of 4.05°, 18.52°, 19.24°, 20.31° and 22.60°±0.2°. In another embodiment, the cocrystal is characterized by an XRPD pattern as shown in FIG. 5.

Figure 5:
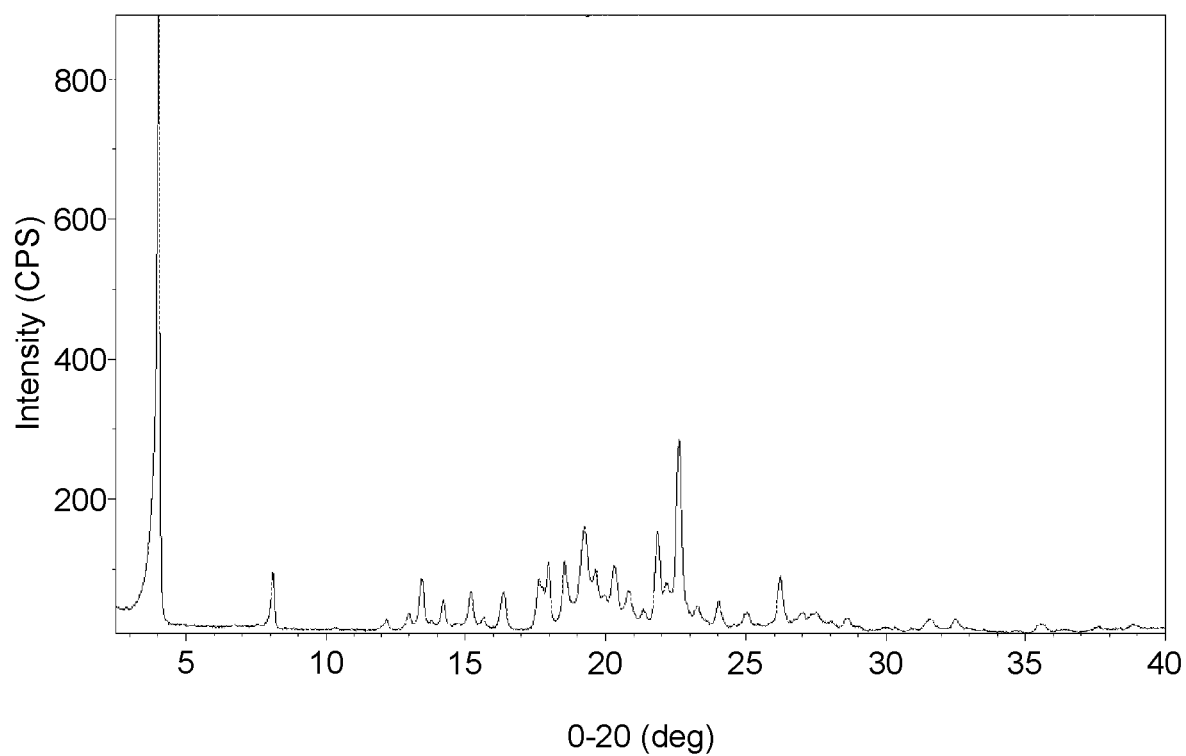
FIG. 5 is an XRPD pattern of cocrystal Form B which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and hippuric acid.

FIG. 5 shows an X-ray powder diffraction (XRPD) pattern of cocrystal Form B obtained using Cu-Kα radiation. Peaks identified in FIG. 5 include those listed in Table 4.

TABLE 4

| Diffraction angle (2θ) | d spacing (Å) |
| --- | --- |
| 4.05 ± 0.20 | 21.819 ± 1.133 |
| 8.13 ± 0.20 | 10.879 ± 0.274 |
| 13.46 ± 0.20 | 6.579 ± 0.099 |
| 15.20 ± 0.20 | 5.831 ± 0.077 |
| 17.59 ± 0.20 | 5.043 ± 0.058 |
| 17.94 ± 0.20 | 4.945 ± 0.055 |
| 18.52 ± 0.20 | 4.791 ± 0.052 |
| 19.24 ± 0.20 | 4.613 ± 0.048 |
| 19.64 ± 0.20 | 4.520 ± 0.046 |
| 20.31 ± 0.20 | 4.373 ± 0.043 |
| 21.85 ± 0.20 | 4.068 ± 0.037 |
| 22.60 ± 0.20 | 3.935 ± 0.035 |
| 26.24 ± 0.20 | 3.396 ± 0.026 |

Table 5 shows the unit cell parameters of cocrystal Form B derived from the corresponding indexed XRPD data. In one embodiment, the cocrystal is selected from the group consisting of a cocrystal that exhibits crystal parameters approximately equal to the following: a=5.069 Å, b=43.443 Å, c=13.792 Å, α=90°, β=90.35, γ=90° volume=3037.1 Å$^3$/cell, and space group=P2$_1$ (4), and a cocrystal that exhibits crystal parameters approximately equal to the following: a=5.068 Å, b=13.779 Å, c=43.395 Å, α=90°, β=90°, γ 90°, volume=3030.4 Å$^3$/cell, and space group=P2$_1$2$_1$2$_1$ (19).

TABLE 5

|  | MLN4924 hippuric acid | MLN4924 hippuric acid |
| --- | --- | --- |
| Bravais Type | Primitive Monoclinic | Primitive Orthorhombic |
| a [Å] | 5.069 | 5.068 |
| b [Å] | 43.443 | 13.779 |
| c [Å] | 13.792 | 43.395 |
| α [deg] | 90 | 90 |
| β [deg] | 90.35 | 90 |
| γ [deg] | 90 | 90 |
| Volume [Å$^3$/cell] | 3037.1 | 3030.4 |
| Chiral Contents ? | Chiral | Chiral |
| Extinction Symbol | P 1 21 1 | P21 21 21 |
| Space Group(s) | P2$_1$ (4) | P2$_1$2$_1$2$_1$ (19) |
| Source | Manual Input | Manual Input |

Figure 6:
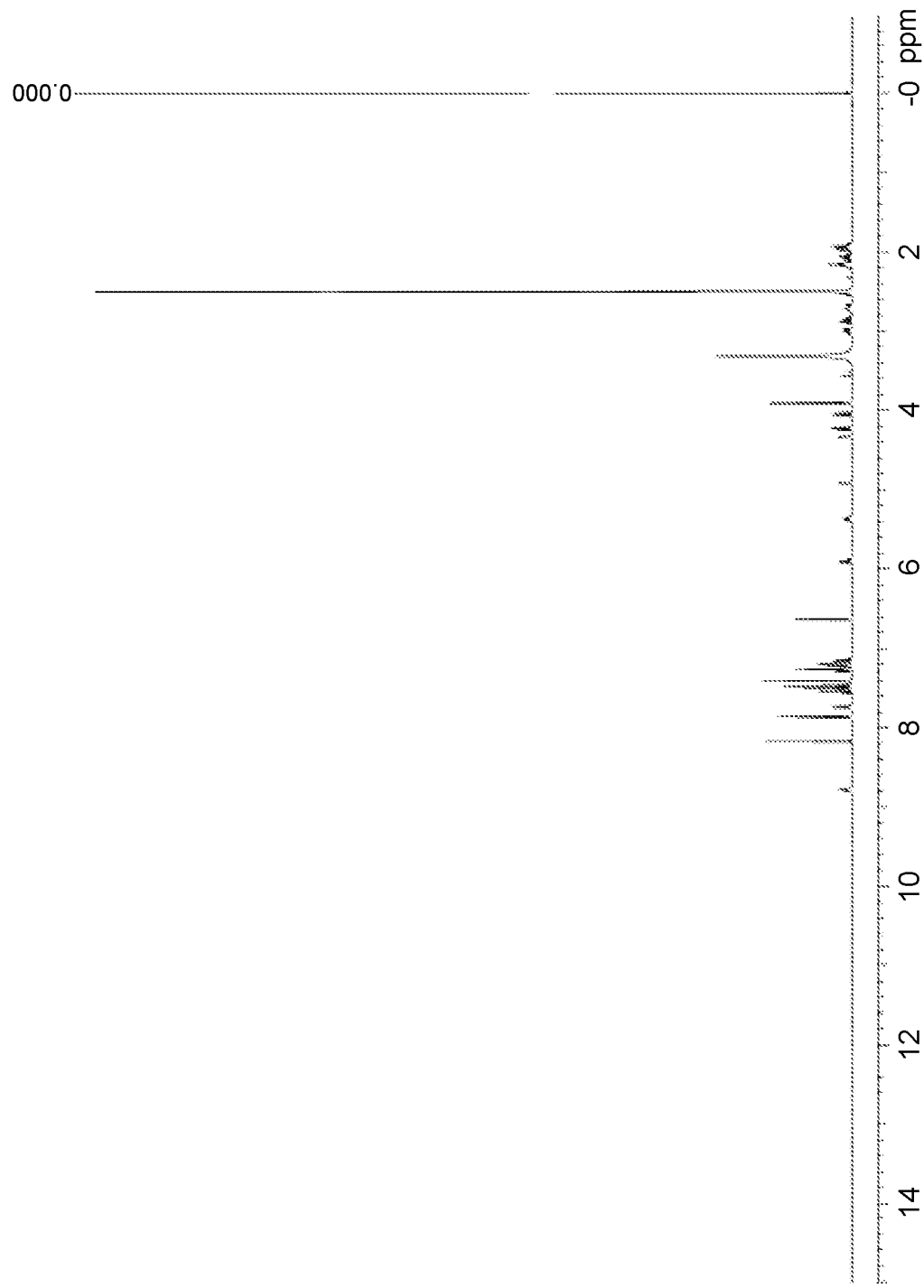
FIG. 6 is a ¹H-NMR of cocrystal Form B which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and hippuric acid.

FIG. 6 shows a $^1$H-NMR of cocrystal Form B. The $^1$H-NMR indicates that the stoichiometric ratio of MLN4924 to hippuric acid is 1:1 and cocrystal Form B is an anhydrous mono-glycolic acid cocrystal. In one embodiment, the cocrystal is characterized by a $^1$H-NMR substantially similar to FIG. 6.

Figure 7:
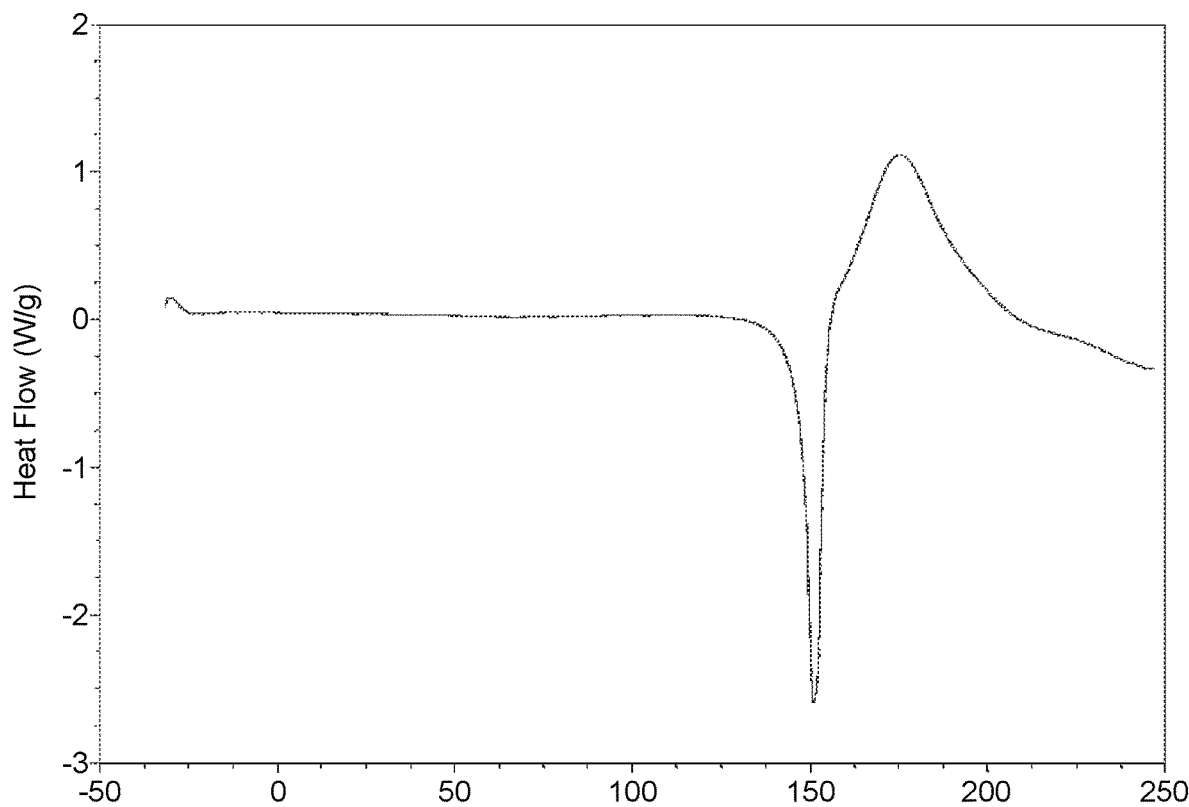
FIG. 7 is a differential scanning calorimetry (DSC) profile for cocrystal Form B which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and hippuric acid.

FIG. 7 shows a differential scanning calorimetry profile (DSC) of cocrystal Form B. The DSC graph plots the heat flow as a function of temperature from a sample, the temperature rate change being about 10° C./min. In one embodiment, the cocrystal is characterized by a DSC profile characterized by an endothermic peak at about 150.9° C. In another embodiment, the cocrystal is characterized by a DSC profile as shown in FIG. 7.

Figure 8:
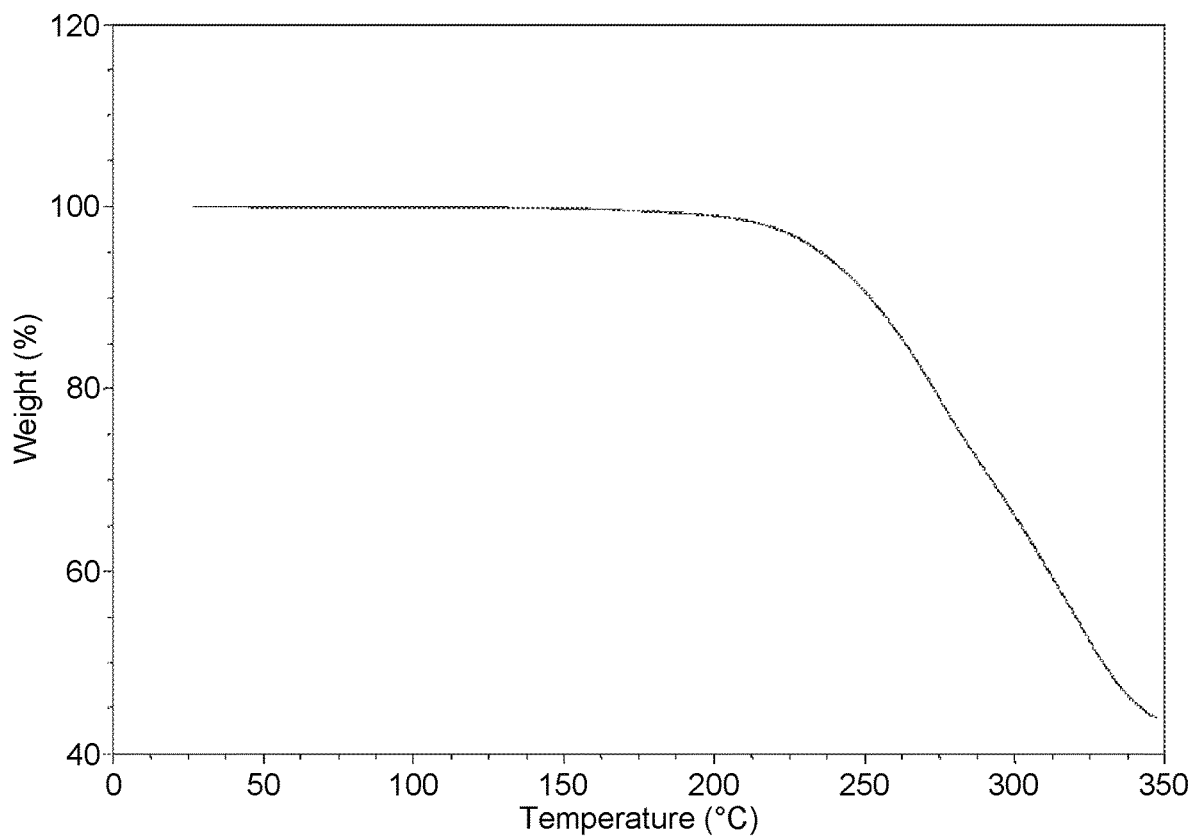
FIG. 8 is a thermal gravimetric analysis (TGA) profile for cocrystal Form B which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and hippuric acid.

FIG. 8 shows a thermal gravimetric analysis (TGA) profile of cocrystal Form B. The TGA profile plots the percent loss of weight of the sample as a function of temperature, the temperature rate change being about 10° C./min. In one embodiment, the cocrystal is characterized by a TGA characterized by a weight loss at about 235° C., suggesting the material is anhydrous and unsolvated. In another embodiment, the cocrystal is characterized by a TGA profile as shown in FIG. 8.

In one embodiment, the cocrystal is characterized by at least two of the following features (I-i)-(I-iv):
(I-i) an XRPD pattern having peaks at 2θ angles of 4.05°, 19.24°, and 22.60°+0.2°;
(I-ii) a $^1$H-NMR substantially similar to FIG. 6;
(I-iii) a DSC profile as shown in FIG. 7; or
(I-iv) a TGA profile as shown in FIG. 8.

In one embodiment, the cocrystal is cocrystal Form B, which is characterized by one or more of the following features: an XRPD pattern as shown in FIG. 5, a $^1$H-NMR substantially similar to FIG. 6, a DSC profile as shown in FIG. 7, or a TGA profile as shown in FIG. 8.

In one embodiment, the cocrystal is a cocrystal of ((1S, 2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and L-proline.

In one embodiment, the cocrystal is characterized by an XRPD pattern having peaks at 2θ angles of 16.1°, 18.4°, and 22.3°+0.2°. In one embodiment, the cocrystal is characterized by an XRPD pattern having peaks at 2θ angles of 16.1°, 18.4°, 19.9°, 21.0°, and 22.3°±0.2°. In another embodiment, the cocrystal is characterized by an XRPD pattern as shown in FIG. 10.

Figure 10:
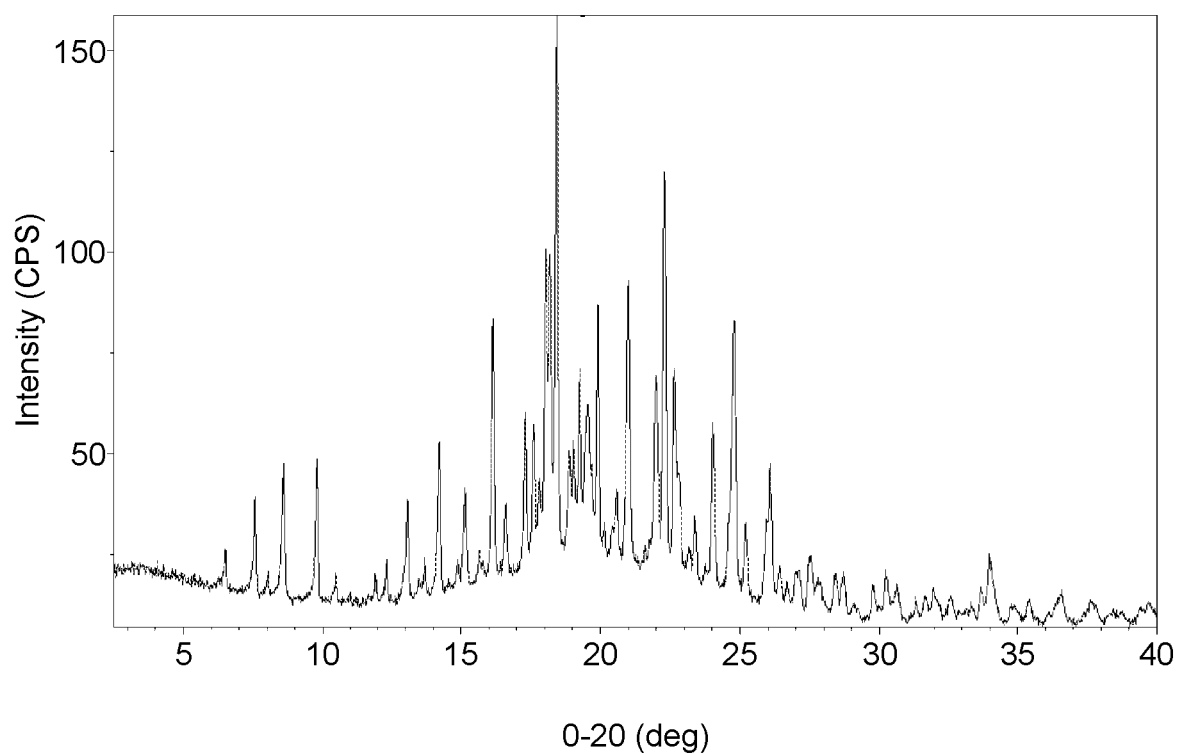
FIG. 10 is an XRPD pattern of cocrystal Form D which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and L-proline.

FIG. 10 shows an X-ray powder diffraction (XRPD) pattern of cocrystal Form D obtained using Cu-Kα radiation. Peaks identified in FIG. 10 include those listed in Table 6.

TABLE 6

| Diffraction angle | d spacing (Å) |
| --- | --- |
| 6.5 ± 0.2 | 13.559 ± 0.429 |
| 7.6 ± 0.2 | 11.676 ± 0.316 |
| 8.1 ± 0.2 | 10.974 ± 0.279 |
| 8.6 ± 0.2 | 10.293 ± 0.245 |
| 9.8 ± 0.2 | 9.031 ± 0.188 |
| 10.5 ± 0.2 | 8.455 ± 0.164 |
| 11.9 ± 0.2 | 7.416 ± 0.126 |
| 12.3 ± 0.2 | 7.186 ± 0.118 |
| 13.1 ± 0.2 | 6.774 ± 0.105 |
| 13.7 ± 0.2 | 6.461 ± 0.095 |
| 14.2 ± 0.2 | 6.227 ± 0.088 |
| 15.1 ± 0.2 | 5.851 ± 0.078 |
| 16.1 ± 0.2 | 5.490 ± 0.068 |
| 16.6 ± 0.2 | 5.342 ± 0.065 |
| 17.3 ± 0.2 | 5.122 ± 0.059 |
| 17.6 ± 0.2 | 5.040 ± 0.057 |
| 18.2 ± 0.2 | 4.879 ± 0.054 |
| 18.4 ± 0.2 | 4.817 ± 0.052 |
| 19.0 ± 0.2 | 4.666 ± 0.049 |
| 19.3 ± 0.2 | 4.610 ± 0.048 |
| 19.6 ± 0.2 | 4.540 ± 0.046 |
| 19.9 ± 0.2 | 4.461 ± 0.045 |
| 20.6 ± 0.2 | 4.314 ± 0.042 |
| 21.0 ± 0.2 | 4.229 ± 0.040 |
| 22.0 ± 0.2 | 4.042 ± 0.037 |
| 22.3 ± 0.2 | 3.988 ± 0.036 |
| 22.6 ± 0.2 | 3.927 ± 0.035 |
| 23.4 ± 0.2 | 3.805 ± 0.032 |
| 24.0 ± 0.2 | 3.703 ± 0.031 |
| 24.8 ± 0.2 | 3.592 ± 0.029 |
| 25.2 ± 0.2 | 3.534 ± 0.028 |
| 26.1 ± 0.2 | 3.418 ± 0.026 |
| 27.5 ± 0.2 | 3.241 ± 0.023 |
| 28.7 ± 0.2 | 3.109 ± 0.021 |
| 29.1 ± 0.2 | 3.066 ± 0.021 |

Figure 11:
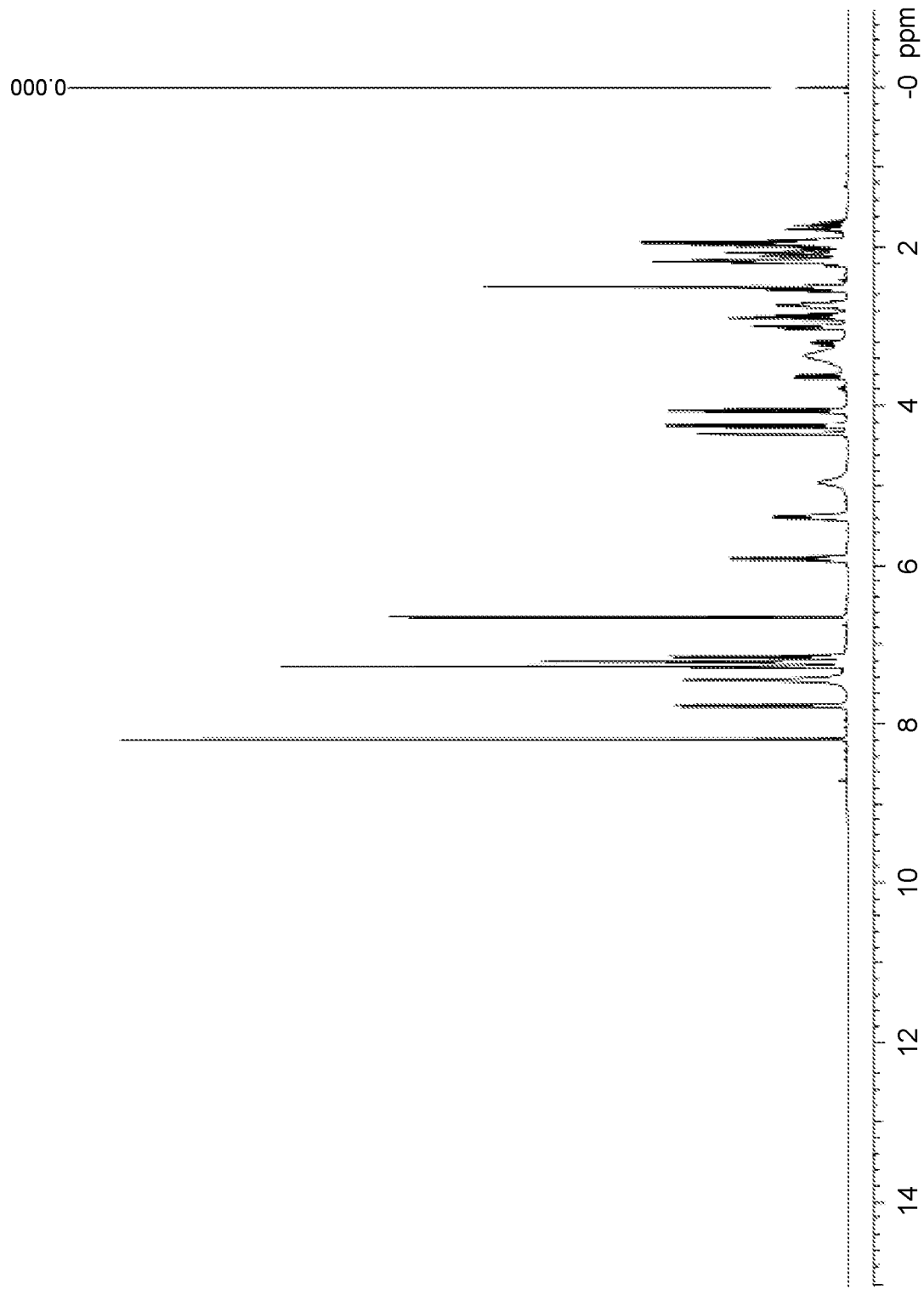
FIG. 11 is a ¹H-NMR of cocrystal Form D which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and L-proline.

FIG. 11 shows a $^1$H-NMR of cocrystal Form D. The $^1$H-NMR indicates that the stoichiometric ratio of MLN4924 to L-proline is 1:0.3. In one embodiment, the cocrystal is characterized by a $^1$H-NMR substantially similar to FIG. 11.

In one embodiment, the cocrystal is characterized by both of the following features (I-i) and (I-ii):

(I-i) an XRPD pattern having peaks at 2θ angles of 16.10, 18.4°, and 22.3°+0.2°; or (I-ii) a $^1$H-NMR substantially similar to FIG. 11.

In one embodiment, the cocrystal is cocrystal Form D, which is characterized by one or more of the following features: an XRPD pattern as shown in FIG. 10 or a $^1$H-NMR substantially similar to FIG. 11.

In one embodiment, the cocrystal is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and saccharin.

In one embodiment, the cocrystal is saccharin cocrystal Form E, which is obtained as a mixture containing Form E, MLN4924, and saccharin.

In one embodiment, the cocrystal is an anhydrous mono-saccharin cocrystal.

In one embodiment, the cocrystal is characterized by an XRPD pattern having peaks at 2θ angles of 7.86°, 15.81°, and 17.97°+0.2°. In one embodiment, the cocrystal is characterized by an XRPD pattern having peaks at 2θ angles of 7.86°, 15.03°, 15.81°, 17.97° and 24.15°+0.2°. In another embodiment, the cocrystal is characterized by an XRPD pattern as shown in FIG. 12.

Figure 12:
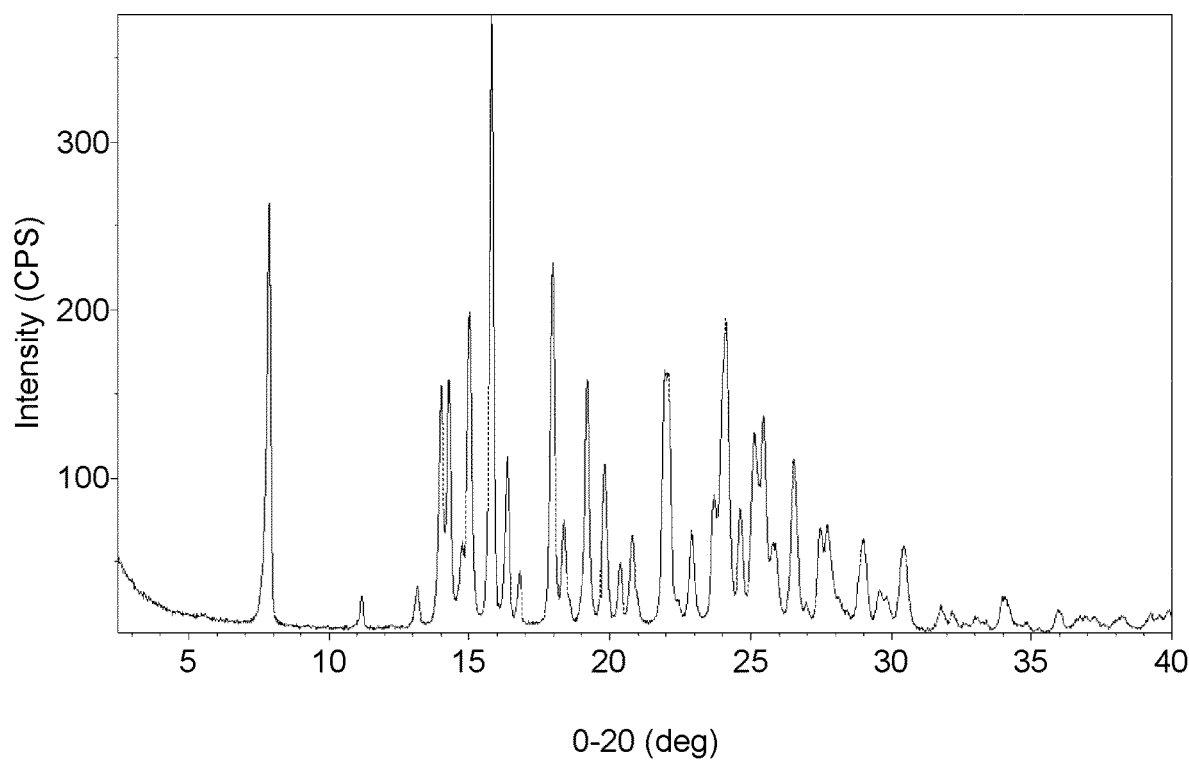
FIG. 12 is an XRPD pattern of cocrystal Form F which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and saccharin.

FIG. 12 shows an X-ray powder diffraction (XRPD) pattern of Form F obtained using Cu-Kα radiation. Peaks identified in FIG. 12 include those listed in Table 7.

TABLE 7

| Diffraction angle | d spacing (Å) |
| --- | --- |
| 7.86 ± 0.20 | 11.254 ± 0.294 |
| 14.02 ± 0.20 | 6.316 ± 0.091 |
| 14.31 ± 0.20 | 6.191 ± 0.087 |
| 15.03 ± 0.20 | 5.897 ± 0.079 |
| 15.81 ± 0.20 | 5.605 ± 0.071 |
| 16.36 ± 0.20 | 5.418 ± 0.067 |
| 17.97 ± 0.20 | 4.937 ± 0.055 |
| 19.24 ± 0.20 | 4.614 ± 0.048 |
| 19.84 ± 0.20 | 4.476 ± 0.045 |
| 21.96 ± 0.20 | 4.048 ± 0.037 |
| 22.11 ± 0.20 | 4.020 ± 0.036 |
| 24.00 ± 0.20 | 3.708 ± 0.031 |
| 24.15 ± 0.20 | 3.685 ± 0.030 |
| 25.14 ± 0.20 | 3.543 ± 0.028 |
| 25.49 ± 0.20 | 3.495 ± 0.027 |
| 26.54 ± 0.20 | 3.359 ± 0.025 |

Table 8 shows the unit cell parameters of cocrystal Form F derived from the corresponding indexed XRPD data. In one embodiment, the cocrystal exhibits crystal parameters that are approximately equal to the following: a=7.412 Å, b=11.993 Å, c=31.631 Å, α=90°, β=90°, γ=90°, volume=2811.7 Å$^3$/cell, and space group=P2$_1$2$_1$2$_1$ (19).

TABLE 8

| | MLN4924 saccharin |
| --- | --- |
| Bravais Type | Primitive Orthohombic |
| a [Å] | 7.412 |
| b [Å] | 11.993 |
| c [Å] | 31.631 |
| α [deg] | 90 |
| β [deg] | 90 |
| γ [deg] | 90 |
| Volume [Å$^3$/cell] | 2811.7 |
| Chiral Contents ? | Chiral |
| Extinction Symbol | P 21 21 21 |
| Space Group(s) | P2$_1$2$_1$2$_1$ (19) |
| Source | Manual Input |

Figure 13:
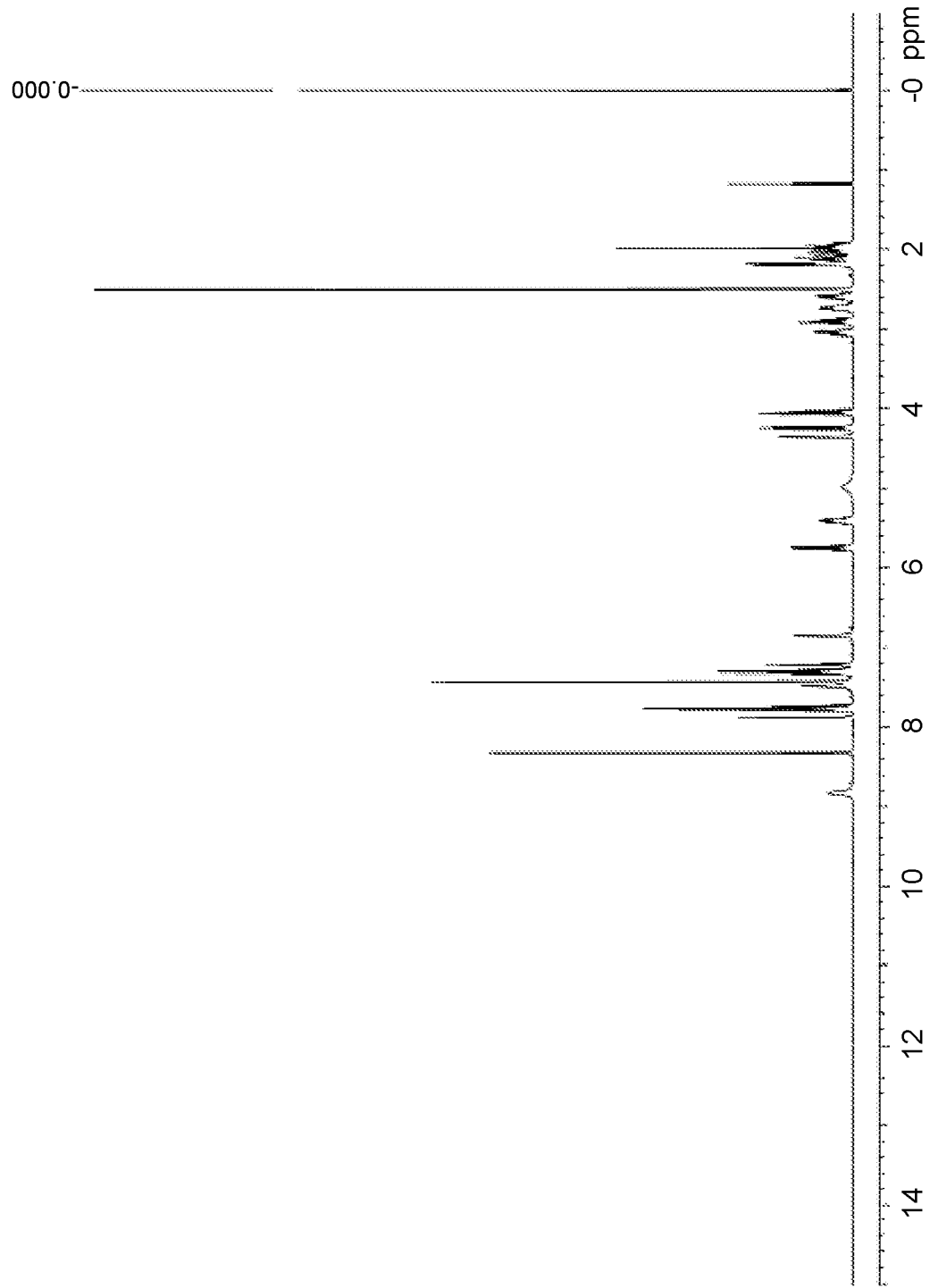
FIG. 13 is a ¹H-NMR of cocrystal Form F which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and saccharin.

FIG. 13 shows a $^1$H-NMR of cocrystal Form F. The $^1$H-NMR indicates that the stoichiometric ratio of MLN4924 to saccharin is 1:1 and cocrystal Form F is an anhydrous mono-saccharin cocrystal. In one embodiment, the cocrystal is characterized by a $^1$H-NMR substantially similar to FIG. 13.

Figure 14:
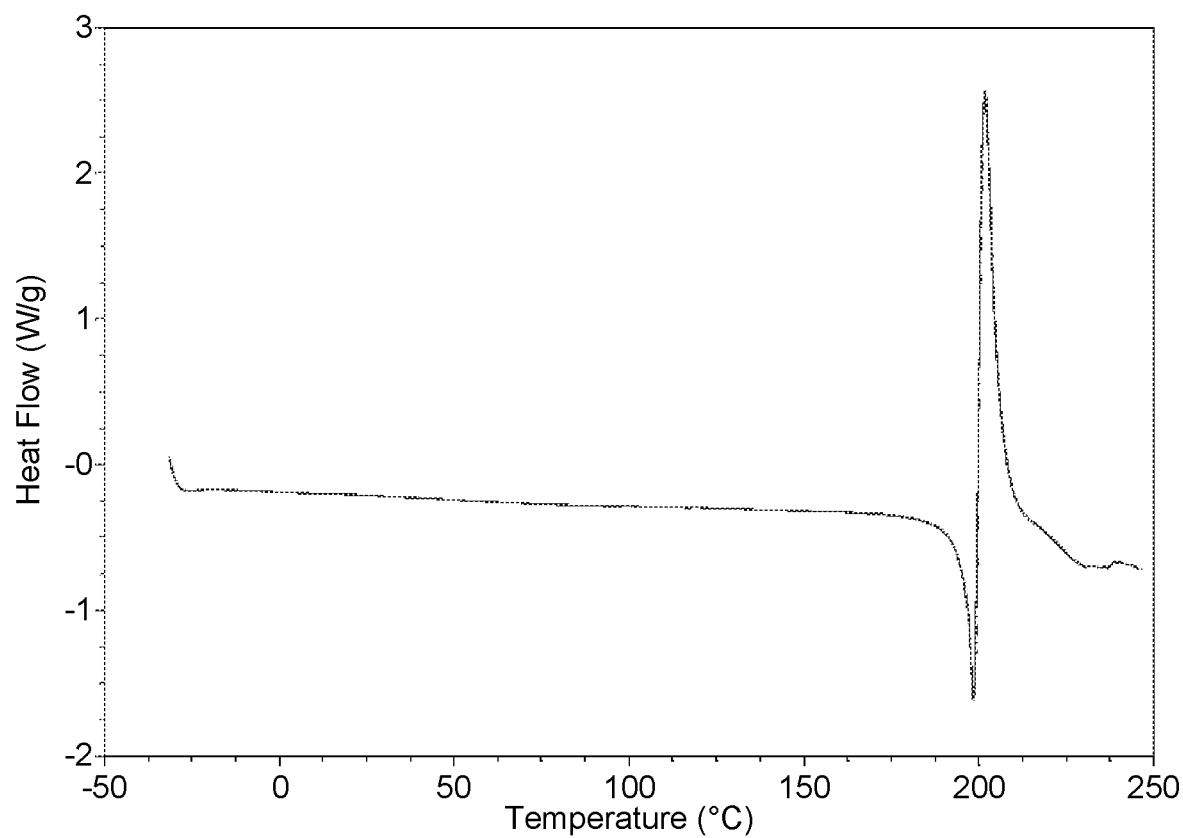
FIG. 14 is a differential scanning calorimetry (DSC) profile for cocrystal Form F which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and saccharin.

FIG. 14 shows a differential scanning calorimetry profile (DSC) of cocrystal Form F. The DSC graph plots the heat flow as a function of temperature from a sample, the temperature rate change being about 10° C./min. In one embodiment, the cocrystal is characterized by a DSC profile characterized by an endothermic peak at about 198.5° C. overlapping with an endothermic peak at about 201.8° C. In another embodiment, the cocrystal is characterized by a DSC profile as shown in FIG. 14.

Figure 15:
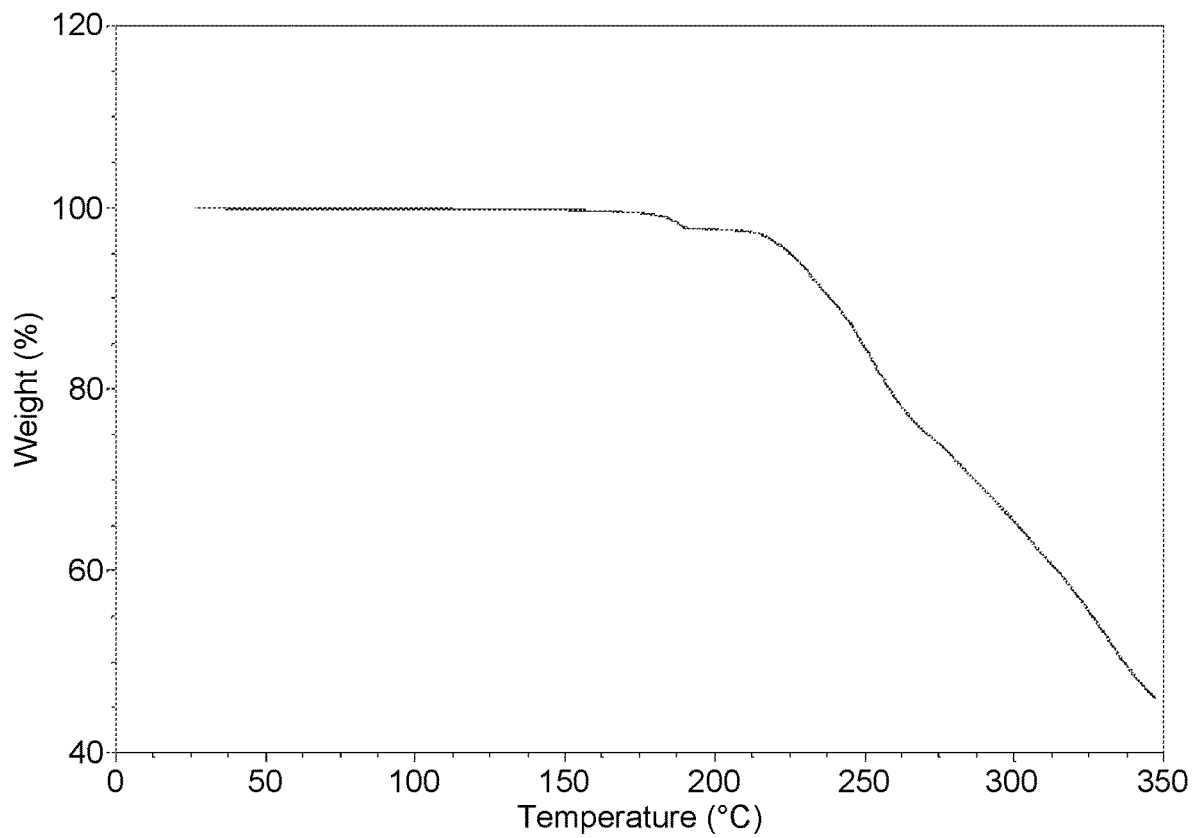
FIG. 15 is a thermal gravimetric analysis (TGA) profile for cocrystal Form F which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and saccharin.

FIG. 15 shows a thermal gravimetric analysis (TGA) profile of cocrystal Form F. The TGA profile plots the percent loss of weight of the sample as a function of temperature, the temperature rate change being about 10° C./min. In one embodiment, the cocrystal is characterized by a TGA characterized by an about 1.9 wt % loss between about 171° C. and about 200° C. In another embodiment, the cocrystal is characterized by a TGA profile as shown in FIG. 15.

In one embodiment, the cocrystal is characterized by at least two of the following features (I-i)-(I-iv):
(I-ii) an XRPD pattern having peaks at 2θ angles of 7.86°, 15.81°, and 17.97°+0.2°;
(I-iii) a ¹H-NMR substantially similar to FIG. 13;
(I-iv) a DSC profile as shown in FIG. 14; or
(I-v) a TGA profile as shown in FIG. 15.

In one embodiment, the cocrystal is cocrystal Form F, which is characterized by one or more of the following features: an XRPD pattern as shown in FIG. 12, a ¹H-NMR substantially similar to FIG. 13, a DSC profile as shown in FIG. 14, or a TGA profile as shown in FIG. 15.

In one embodiment, the cocrystal is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and piperazine. In one embodiment, the cocrystal is piperazine cocrystal acetonitrile solvate. In another embodiment, the cocrystal has a molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate:piperazine:acetonitrile between 1:0.5:0.6 to 1:0.5:0.2

In one embodiment, the cocrystal is characterized by an XRPD pattern having peaks at 2θ angles of 6.7°, 19.10, and 22.0°±0.2°. In one embodiment, the cocrystal is characterized by an XRPD pattern having peaks at 2θ angles of 6.7°, 17.7°, 18.30, 19.10, and 22.0°±0.2°. In another embodiment, the cocrystal is characterized by an XRPD pattern as shown in FIG. 16.

Figure 16:
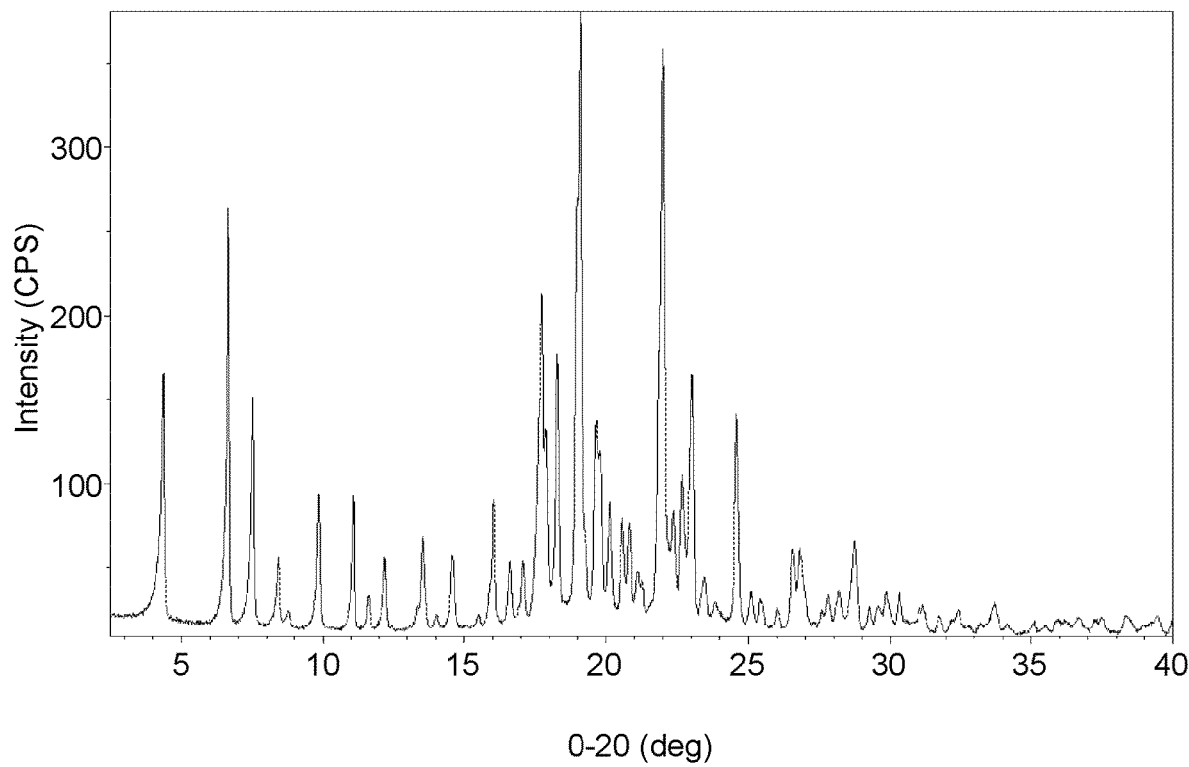
FIG. 16 is an XRPD pattern of cocrystal Form G which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and piperazine.

FIG. 16 shows an X-ray powder diffraction (XRPD) pattern of cocrystal Form G obtained using Cu-Kα radiation. Peaks identified in FIG. 16 include those listed in Table 9.

TABLE 9

| Diffraction angle | d spacing (Å) |
| --- | --- |
| 4.4 ± 0.2 | 20.233 ± 0.971 |
| 6.7 ± 0.2 | 13.279 ± 0.411 |
| 7.5 ± 0.2 | 11.773 ± 0.322 |
| 8.4 ± 0.2 | 10.512 ± 0.256 |
| 8.8 ± 0.2 | 10.092 ± 0.235 |
| 9.9 ± 0.2 | 8.966 ± 0.185 |
| 11.1 ± 0.2 | 7.994 ± 0.147 |
| 11.6 ± 0.2 | 7.616 ± 0.133 |
| 12.2 ± 0.2 | 7.252 ± 0.120 |
| 13.5 ± 0.2 | 6.539 ± 0.098 |
| 14.0 ± 0.2 | 6.307 ± 0.091 |
| 14.6 ± 0.2 | 6.076 ± 0.084 |
| 15.5 ± 0.2 | 5.712 ± 0.074 |
| 16.0 ± 0.2 | 5.523 ± 0.069 |
| 17.7 ± 0.2 | 5.006 ± 0.057 |
| 18.3 ± 0.2 | 4.856 ± 0.053 |
| 19.1 ± 0.2 | 4.649 ± 0.049 |
| 19.7 ± 0.2 | 4.516 ± 0.046 |
| 20.1 ± 0.2 | 4.409 ± 0.044 |
| 20.8 ± 0.2 | 4.268 ± 0.041 |
| 21.1 ± 0.2 | 4.208 ± 0.040 |
| 21.3 ± 0.2 | 4.179 ± 0.039 |
| 22.0 ± 0.2 | 4.041 ± 0.037 |
| 22.4 ± 0.2 | 3.972 ± 0.035 |
| 22.7 ± 0.2 | 3.920 ± 0.034 |
| 23.0 ± 0.2 | 3.864 ± 0.033 |
| 23.5 ± 0.2 | 3.793 ± 0.032 |
| 23.9 ± 0.2 | 3.731 ± 0.031 |
| 24.6 ± 0.2 | 3.621 ± 0.029 |
| 25.1 ± 0.2 | 3.547 ± 0.028 |
| 25.4 ± 0.2 | 3.501 ± 0.027 |
| 26.0 ± 0.2 | 3.426 ± 0.026 |
| 26.6 ± 0.2 | 3.356 ± 0.025 |
| 26.8 ± 0.2 | 3.325 ± 0.025 |
| 27.8 ± 0.2 | 3.208 ± 0.023 |
| 28.2 ± 0.2 | 3.165 ± 0.022 |
| 28.7 ± 0.2 | 3.107 ± 0.021 |

TABLE 9-continued

| Diffraction angle | d spacing (Å) |
| --- | --- |
| 29.3 ± 0.2 | 3.053 ± 0.021 |
| 29.9 ± 0.2 | 2.988 ± 0.020 |

Table 10 shows the unit cell parameters of cocrystal Form G derived from the indexed XRPD data. In one embodiment, the cocrystal exhibits crystal parameters that are approximately equal to the following: a=13.346 Å, b=10.014 Å, c=20.285 Å, α=90°, β=97.01°, γ=90°, volume=2690.7 Å³/cell, and space group=P2₁ (4).

TABLE 10

| | MLN4924 saccharin |
| --- | --- |
| Bravais Type | Primitive Monoclinic |
| a [Å] | 13.346 |
| b [Å] | 10.014 |
| c [Å] | 20.285 |
| α [deg] | 90 |
| β [deg] | 97.01 |
| γ [deg] | 90 |
| Volume [Å³/cell] | 2690.7 |
| Chiral Contents ? | Chiral |
| Extinction Symbol | P 21 21 21 |
| Space Group(s) | P2₁2₁2₁ (19) |
| Source | Triads Algorithm |

Figure 17:
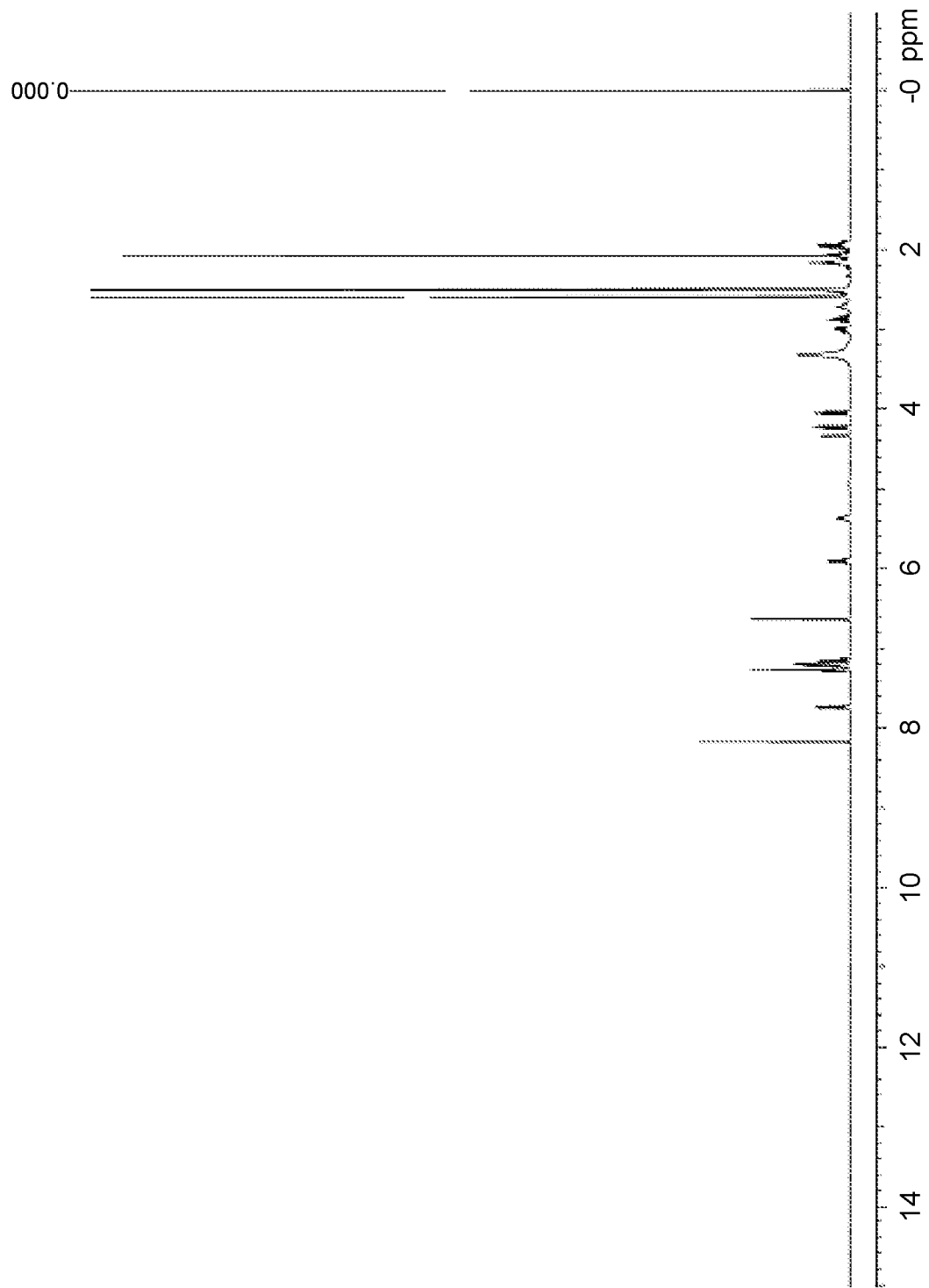
FIG. 17 is a ¹H-NMR of cocrystal Form G which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and piperazine.

FIG. 17 shows a ¹H-NMR of cocrystal Form G. The ¹H-NMR indicates that the stoichiometric ratio of MLN4924:piperazine:acetonitrile is 1:0.5:0.6 and cocrystal Form G is a piperazine cocrystal acetonitrile solvate. In one embodiment, the cocrystal is characterized by a ¹H-NMR substantially similar to FIG. 17.

Figure 18:
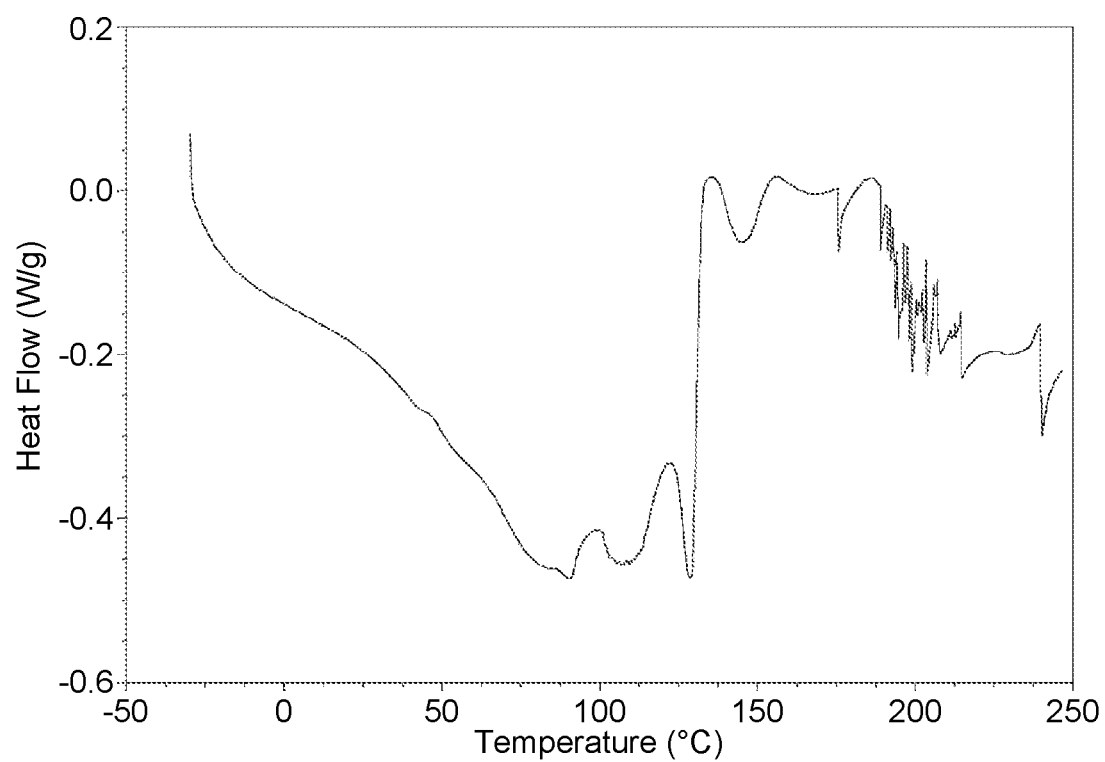
FIG. 18 is a differential scanning calorimetry (DSC) profile for cocrystal Form G which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and piperazine.

FIG. 18 shows a differential scanning calorimetry profile (DSC) of cocrystal Form G. The DSC graph plots the heat flow as a function of temperature from a sample, the temperature rate change being about 10° C./min. In one embodiment, the cocrystal is characterized by a DSC profile as shown in FIG. 18.

Figure 19:
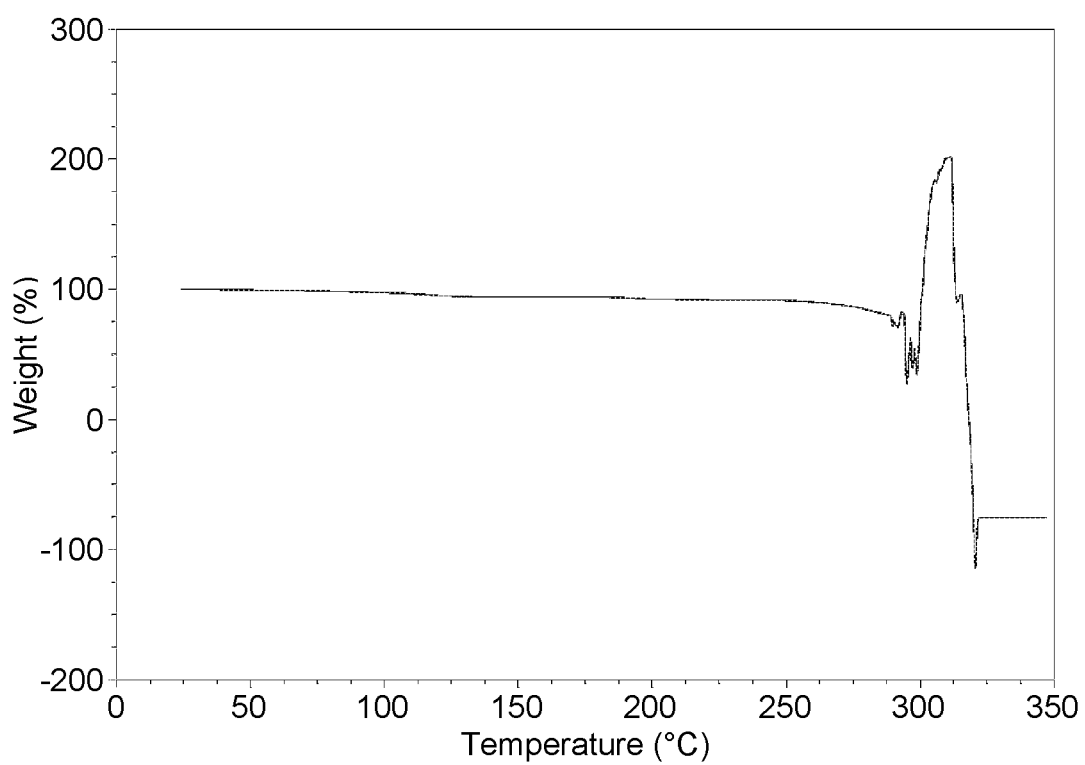
FIG. 19 is a thermal gravimetric analysis (TGA) profile for cocrystal Form G which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and piperazine.

FIG. 19 also shows a thermal gravimetric analysis (TGA) profile of cocrystal Form G. The TGA profile plots the percent loss of weight of the sample as a function of temperature, the temperature rate change being about 10° C./min. In one embodiment, the cocrystal is characterized by a TGA characterized by an about 5.7 wt % loss between about 24° C. and about 150° C. In another embodiment, the cocrystal is characterized by a TGA profile as shown in FIG. 19.

In one embodiment, the cocrystal is characterized by at least two of the following features (I-i)-(I-iv):
(I-i) an XRPD pattern having peaks at 2θ angles of 6.7°, 19.10, and 22.00°±0.2°;
(I-ii) a ¹H-NMR substantially similar to FIG. 17;
(I-iii) a DSC profile substantially as shown in FIG. 18; or
(I-iv) a TGA profile substantially as shown in FIG. 19.

In one embodiment, the cocrystal is cocrystal Form G, which is characterized by one or more of the following features: an XRPD pattern as shown in FIG. 16, a ¹H-NMR substantially similar to FIG. 17, a DSC profile as shown in FIG. 18, or a TGA profile as shown in FIG. 19.

In one embodiment, the cocrystal is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)

methyl sulfamate and gentisic acid. In one embodiment, the cocrystal is gentisic acid cocrystal acetonitrile solvate.

In one embodiment, the cocrystal is characterized by an XRPD pattern having peaks at 2θ angles of 5.1°, 9.4°, and 23.9°+0.2°. In one embodiment, the cocrystal is characterized by an XRPD pattern having peaks at 2θ angles of 5.1°, 9.4°, 19.0°, 21.2°, and 23.9°±0.2°. In another embodiment, the cocrystal is characterized by an XRPD pattern as shown in FIG. 20.

Figure 20:
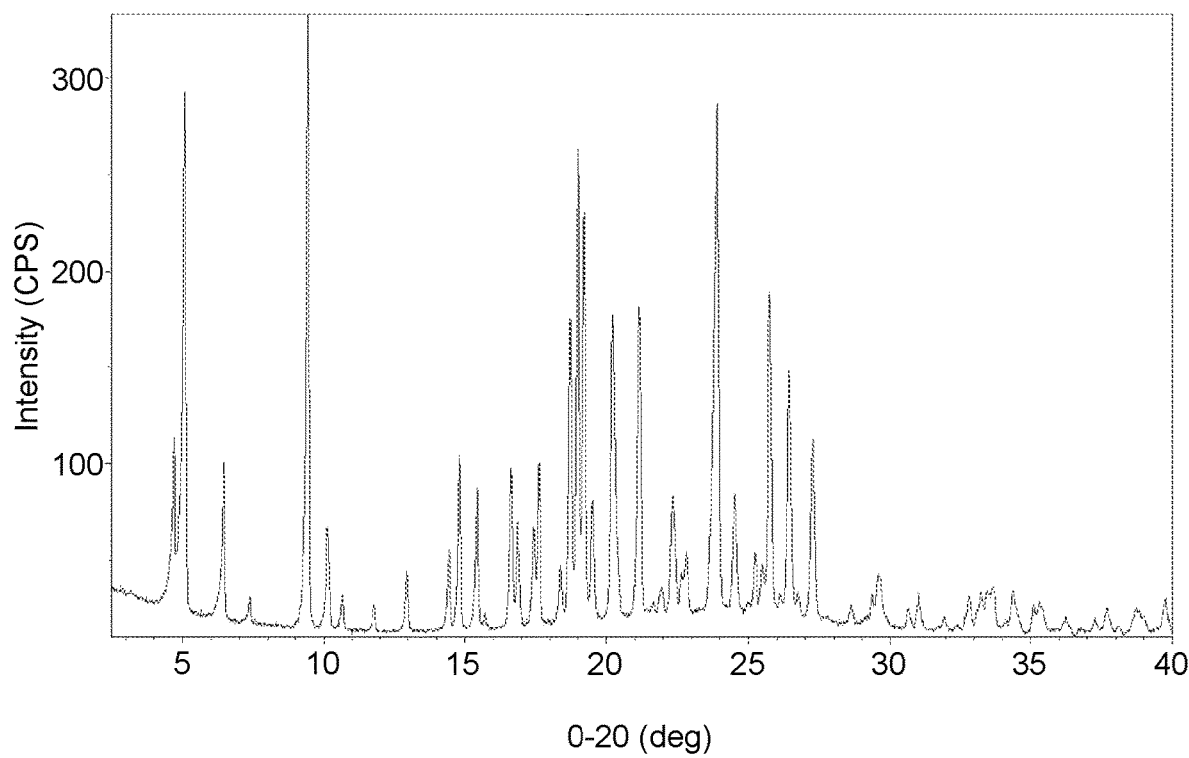
FIG. 20 is an XRPD pattern of cocrystal Form J which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 20 shows an X-ray powder diffraction (XRPD) pattern of cocrystal Form J obtained using Cu-Kα radiation. Peaks identified in FIG. 20 include those listed in Table 11.

TABLE 11

| Diffraction angle | d spacing (Å) |
| --- | --- |
| 4.7 ± 0.2 | 18.811 ± 0.836 |
| 5.1 ± 0.2 | 17.390 ± 0.712 |
| 6.5 ± 0.2 | 13.664 ± 0.435 |
| 7.4 ± 0.2 | 11.993 ± 0.334 |
| 9.4 ± 0.2 | 9.365 ± 0.202 |
| 10.1 ± 0.2 | 8.733 ± 0.175 |
| 10.7 ± 0.2 | 8.297 ± 0.158 |
| 11.8 ± 0.2 | 7.511 ± 0.129 |
| 13.0 ± 0.2 | 6.826 ± 0.106 |
| 14.4 ± 0.2 | 6.134 ± 0.086 |
| 14.8 ± 0.2 | 5.983 ± 0.081 |
| 15.4 ± 0.2 | 5.744 ± 0.075 |
| 16.6 ± 0.2 | 5.331 ± 0.064 |
| 16.9 ± 0.2 | 5.258 ± 0.063 |
| 17.6 ± 0.2 | 5.035 ± 0.057 |
| 18.4 ± 0.2 | 4.835 ± 0.053 |
| 18.7 ± 0.2 | 4.745 ± 0.051 |
| 19.0 ± 0.2 | 4.674 ± 0.049 |
| 19.2 ± 0.2 | 4.618 ± 0.048 |
| 19.5 ± 0.2 | 4.548 ± 0.047 |
| 20.2 ± 0.2 | 4.391 ± 0.043 |
| 21.2 ± 0.2 | 4.199 ± 0.040 |
| 22.3 ± 0.2 | 3.982 ± 0.036 |
| 22.8 ± 0.2 | 3.898 ± 0.034 |
| 23.9 ± 0.2 | 3.723 ± 0.031 |
| 24.5 ± 0.2 | 3.629 ± 0.029 |
| 25.2 ± 0.2 | 3.531 ± 0.028 |
| 25.8 ± 0.2 | 3.459 ± 0.027 |
| 26.4 ± 0.2 | 3.373 ± 0.025 |
| 27.3 ± 0.2 | 3.272 ± 0.024 |
| 28.6 ± 0.2 | 3.118 ± 0.021 |
| 29.4 ± 0.2 | 3.040 ± 0.020 |
| 29.6 ± 0.2 | 3.020 ± 0.020 |

Figure 21:
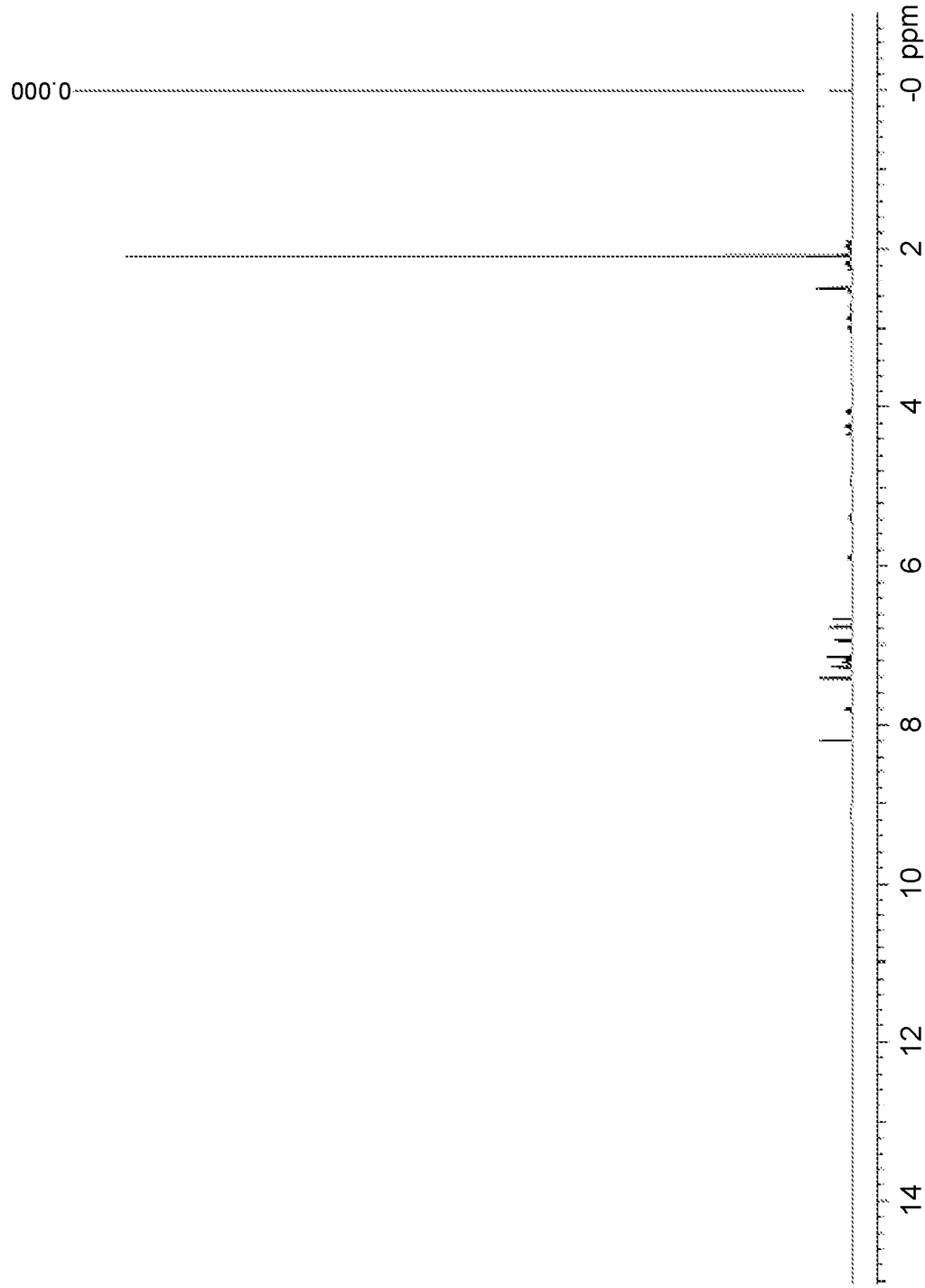
FIG. 21 is a ¹H-NMR of cocrystal Form J which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 21 shows a $^1$H-NMR of cocrystal Form J. The $^1$H-NMR indicates that the stoichiometric ratio of MLN4924:gentisic acid:acetonitrile is 1:1:3 and cocrystal Form J is a gentisic acid cocrystal acetonitrile solvate. In one embodiment, the cocrystal is characterized by a $^1$H-NMR substantially similar to FIG. 21.

In one embodiment, the cocrystal is characterized by both of the following features (I-i) and (I-ii):
(I-i) an XRPD pattern having peaks at 2θ angles of 5.10, 9.40, and 23.9°+0.2°; and
(I-ii) a $^1$H-NMR substantially similar to FIG. 21.

In one embodiment, the cocrystal is cocrystal Form J, which is characterized by one or more of the following features: an XRPD pattern as shown in FIG. 20 or a $^1$H-NMR substantially similar to FIG. 21.

In one embodiment, the cocrystal is characterized by an XRPD pattern having peaks at 2θ angles of 17.0°, 18.5°, and 23.2°+0.2°. In one embodiment, the cocrystal is characterized by an XRPD pattern having peaks at 2θ angles of 4.7°, 17.0°, 18.5°, 22.1°, and 23.2°±0.2°. In another embodiment, the cocrystal is characterized by an XRPD pattern as shown in FIG. 26.

Figure 26:
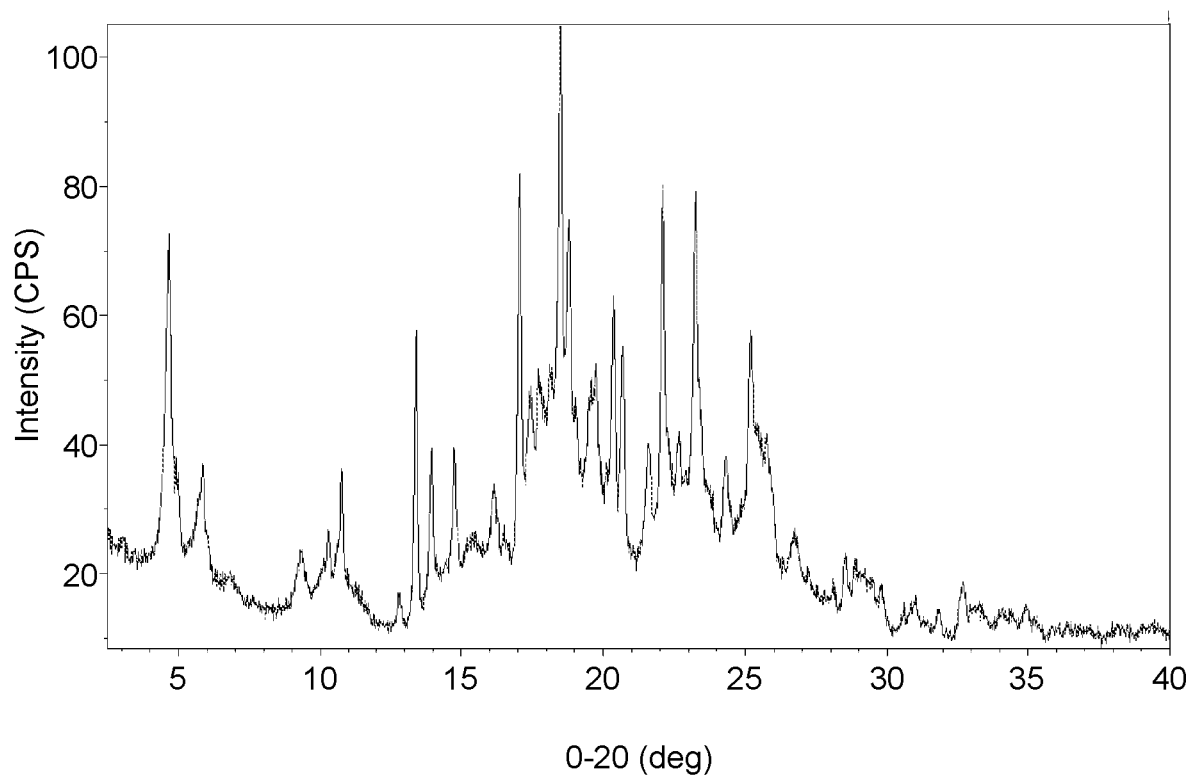
FIG. 26 is an XRPD pattern of cocrystal Form L which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 26 shows an X-ray powder diffraction (XRPD) pattern of cocrystal Form L obtained using Cu-Kα radiation. Peaks identified in FIG. 26 include those listed in Table 12.

TABLE 12

| Diffraction angle | d spacing (Å) |
| --- | --- |
| 3.0 ± 0.2 | 29.034 ± 2.042 |
| 4.7 ± 0.2 | 18.946 ± 0.848 |
| 5.9 ± 0.2 | 15.106 ± 0.534 |
| 6.8 ± 0.2 | 12.961 ± 0.391 |
| 9.3 ± 0.2 | 9.500 ± 0.208 |
| 10.3 ± 0.2 | 8.592 ± 0.170 |
| 10.7 ± 0.2 | 8.232 ± 0.156 |
| 12.8 ± 0.2 | 6.906 ± 0.109 |
| 13.4 ± 0.2 | 6.598 ± 0.099 |
| 13.9 ± 0.2 | 6.354 ± 0.092 |
| 14.8 ± 0.2 | 6.003 ± 0.082 |
| 15.5 ± 0.2 | 5.713 ± 0.074 |
| 16.1 ± 0.2 | 5.490 ± 0.068 |
| 17.0 ± 0.2 | 5.201 ± 0.061 |
| 17.4 ± 0.2 | 5.083 ± 0.058 |
| 17.7 ± 0.2 | 5.002 ± 0.057 |
| 18.1 ± 0.2 | 4.897 ± 0.054 |
| 18.5 ± 0.2 | 4.796 ± 0.052 |
| 18.8 ± 0.2 | 4.724 ± 0.050 |
| 19.7 ± 0.2 | 4.498 ± 0.046 |
| 20.4 ± 0.2 | 4.359 ± 0.043 |
| 20.7 ± 0.2 | 4.297 ± 0.042 |
| 21.6 ± 0.2 | 4.119 ± 0.038 |
| 22.1 ± 0.2 | 4.023 ± 0.036 |
| 22.7 ± 0.2 | 3.921 ± 0.034 |
| 23.2 ± 0.2 | 3.826 ± 0.033 |
| 24.3 ± 0.2 | 3.660 ± 0.030 |
| 25.2 ± 0.2 | 3.536 ± 0.028 |
| 25.8 ± 0.2 | 3.457 ± 0.027 |
| 26.7 ± 0.2 | 3.334 ± 0.025 |
| 27.2 ± 0.2 | 3.278 ± 0.024 |
| 28.1 ± 0.2 | 3.173 ± 0.022 |
| 28.5 ± 0.2 | 3.127 ± 0.022 |
| 28.9 ± 0.2 | 3.092 ± 0.021 |

Figure 27:
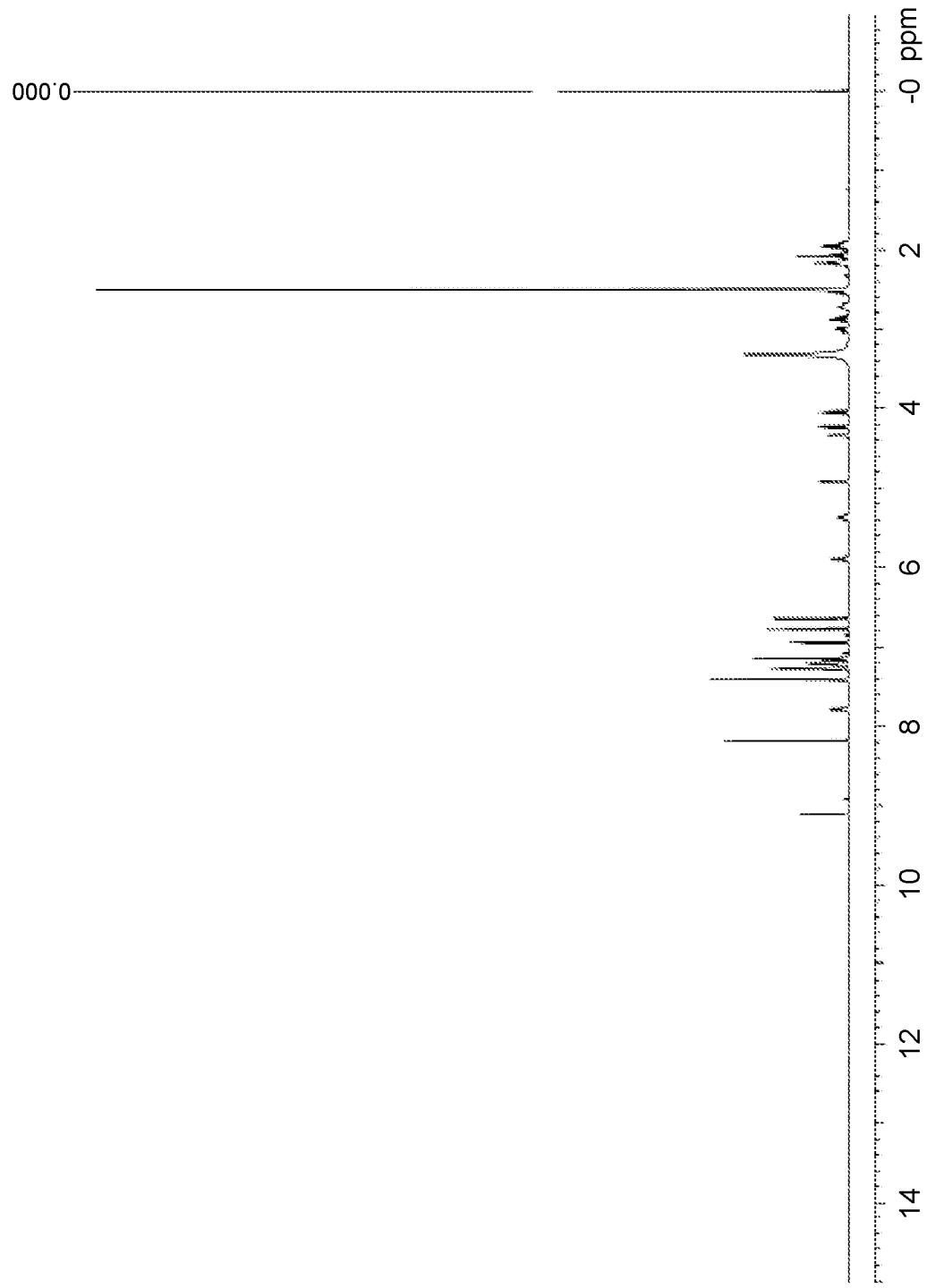
FIG. 27 is a ¹H-NMR of cocrystal Form L which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 27 shows a $^1$H-NMR of cocrystal Form L. The $^1$H-NMR indicates that the stoichiometric ratio of MLN4924:gentisic acid is 1:1. In one embodiment, the cocrystal is characterized by a $^1$H-NMR substantially similar to FIG. 27.

In one embodiment, the cocrystal is characterized by both of the following features (I-i) and (I-ii):
(I-i) an XRPD pattern having peaks at 2θ angles of 17.0°, 18.5°, and 23.2°+0.2°; and
(I-ii) a $^1$H-NMR substantially similar to FIG. 27.

In one embodiment, the cocrystal is cocrystal Form L, which is characterized by one or more of the following features: an XRPD pattern as shown in FIG. 26 or a $^1$H-NMR substantially similar to FIG. 27.

In one embodiment, the cocrystal is characterized by an XRPD pattern having peaks at 2θ angles of 9.6°, 18.10, and 24.5°+0.2°. In one embodiment, the cocrystal is characterized by an XRPD pattern having peaks at 2θ angles of 4.3°, 9.6°, 18.1°, 23.5°, and 24.5°±0.2°. In another embodiment, the cocrystal is characterized by an XRPD pattern as shown in FIG. 28.

Figure 28:
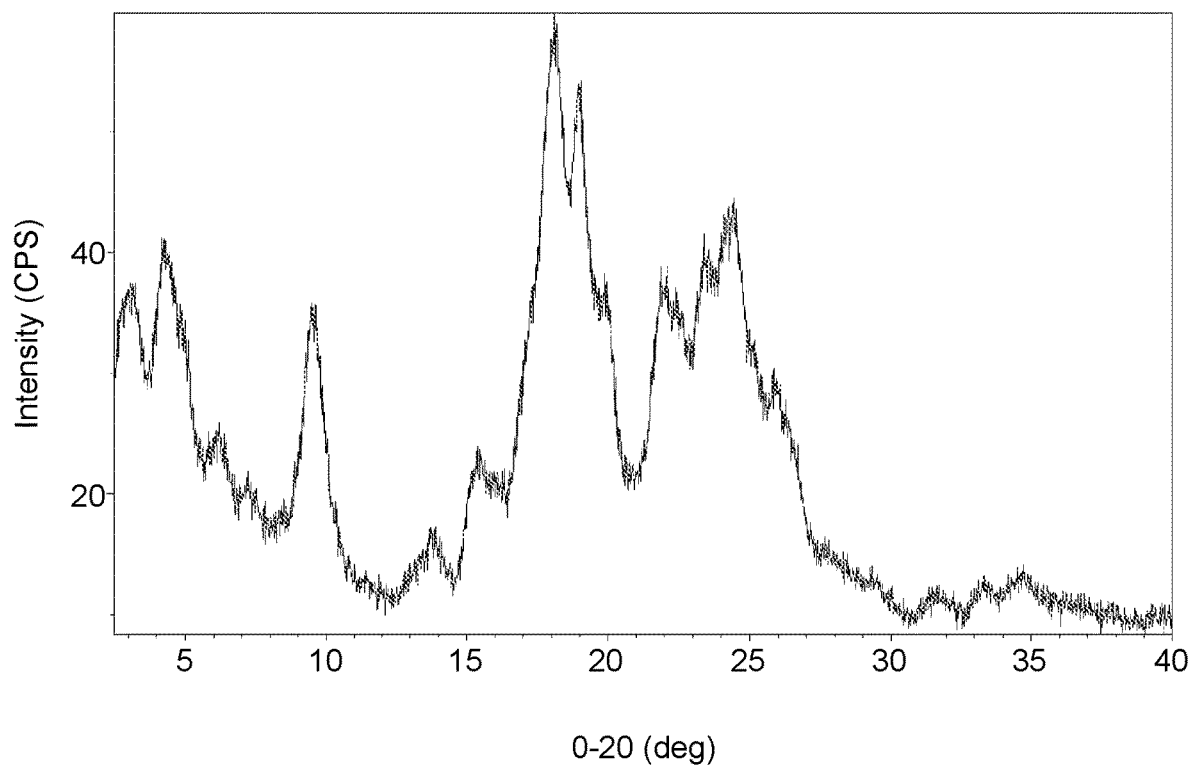
FIG. 28 is an XRPD pattern of cocrystal Form H which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 28 shows an X-ray powder diffraction (XRPD) pattern of cocrystal Form H obtained using Cu-Kα radiation. Peaks identified in FIG. 28 include those listed in Table 13.

TABLE 13

| Diffraction angle | d spacing (Å) |
| --- | --- |
| 3.1 ± 0.2 | 28.563 ± 1.974 |
| 4.3 ± 0.2 | 20.728 ± 1.020 |

TABLE 13-continued

| Diffraction angle | d spacing (Å) |
| --- | --- |
| 6.2 ± 0.2 | 14.214 ± 0.472 |
| 7.2 ± 0.2 | 12.271 ± 0.350 |
| 9.6 ± 0.2 | 9.203 ± 0.195 |
| 13.9 ± 0.2 | 6.376 ± 0.093 |
| 15.4 ± 0.2 | 5.763 ± 0.075 |
| 18.1 ± 0.2 | 4.906 ± 0.054 |
| 19.1 ± 0.2 | 4.658 ± 0.049 |
| 19.9 ± 0.2 | 4.464 ± 0.045 |
| 22.1 ± 0.2 | 4.020 ± 0.036 |
| 23.5 ± 0.2 | 3.778 ± 0.032 |
| 24.5 ± 0.2 | 3.641 ± 0.030 |
| 25.9 ± 0.2 | 3.442 ± 0.026 |

In one embodiment, the cocrystal is cocrystal Form H, which is characterized by an XRPD pattern as shown in FIG. 28.

In one embodiment, the cocrystal is characterized by an XRPD pattern having peaks at 2θ angles of 8.9°, 17.9°, and 22.3°+0.2°. In one embodiment, the cocrystal is characterized by an XRPD pattern having peaks at 2θ angles of 8.9°, 13.8°, 17.9°, 21.4°, and 22.3°±0.2°. In another embodiment, the cocrystal is characterized by an XRPD pattern as shown in FIG. 29.

Figure 29:
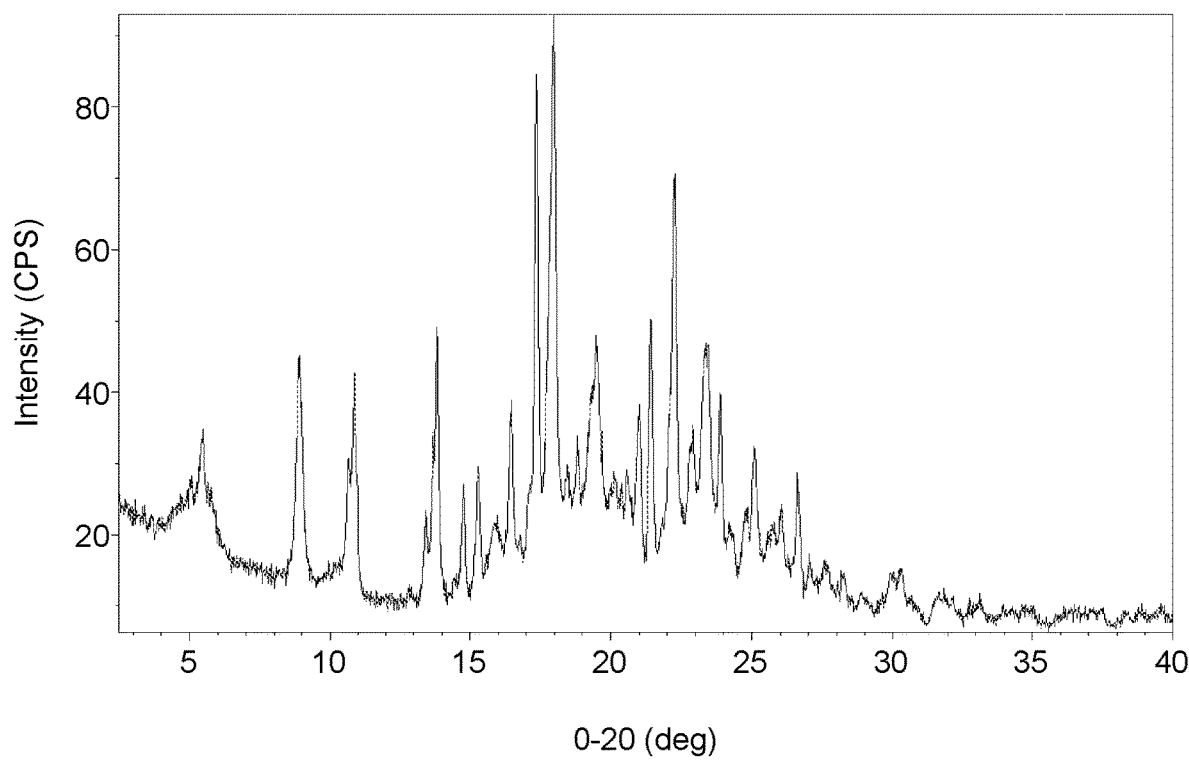
FIG. 29 is an XRPD pattern of cocrystal Form N which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 29 shows an X-ray powder diffraction (XRPD) pattern of cocrystal Form N obtained using Cu-Kα radiation. Peaks identified in FIG. 29 include those listed in Table 14.

TABLE 14

| Diffraction angle | d spacing (Å) |
| --- | --- |
| 5.5 ± 0.2 | 16.168 ± 0.614 |
| 8.9 ± 0.2 | 9.908 ± 0.227 |
| 10.9 ± 0.2 | 8.144 ± 0.152 |
| 13.5 ± 0.2 | 6.581 ± 0.099 |
| 13.8 ± 0.2 | 6.399 ± 0.093 |
| 14.8 ± 0.2 | 6.003 ± 0.082 |
| 15.3 ± 0.2 | 5.800 ± 0.076 |
| 15.9 ± 0.2 | 5.588 ± 0.071 |
| 16.5 ± 0.2 | 5.379 ± 0.066 |
| 17.4 ± 0.2 | 5.107 ± 0.059 |
| 17.9 ± 0.2 | 4.942 ± 0.055 |
| 18.4 ± 0.2 | 4.813 ± 0.052 |
| 18.8 ± 0.2 | 4.720 ± 0.050 |
| 19.5 ± 0.2 | 4.551 ± 0.047 |
| 20.1 ± 0.2 | 4.413 ± 0.044 |
| 21.0 ± 0.2 | 4.229 ± 0.040 |
| 21.4 ± 0.2 | 4.144 ± 0.039 |
| 22.3 ± 0.2 | 3.991 ± 0.036 |
| 22.9 ± 0.2 | 3.881 ± 0.034 |
| 23.4 ± 0.2 | 3.794 ± 0.032 |
| 23.9 ± 0.2 | 3.726 ± 0.031 |
| 24.2 ± 0.2 | 3.678 ± 0.030 |
| 24.8 ± 0.2 | 3.592 ± 0.029 |
| 25.1 ± 0.2 | 3.550 ± 0.028 |
| 26.1 ± 0.2 | 3.420 ± 0.026 |
| 26.6 ± 0.2 | 3.348 ± 0.025 |
| 27.6 ± 0.2 | 3.237 ± 0.023 |
| 28.3 ± 0.2 | 3.158 ± 0.022 |
| 28.9 ± 0.2 | 3.090 ± 0.022 |

Figure 30:
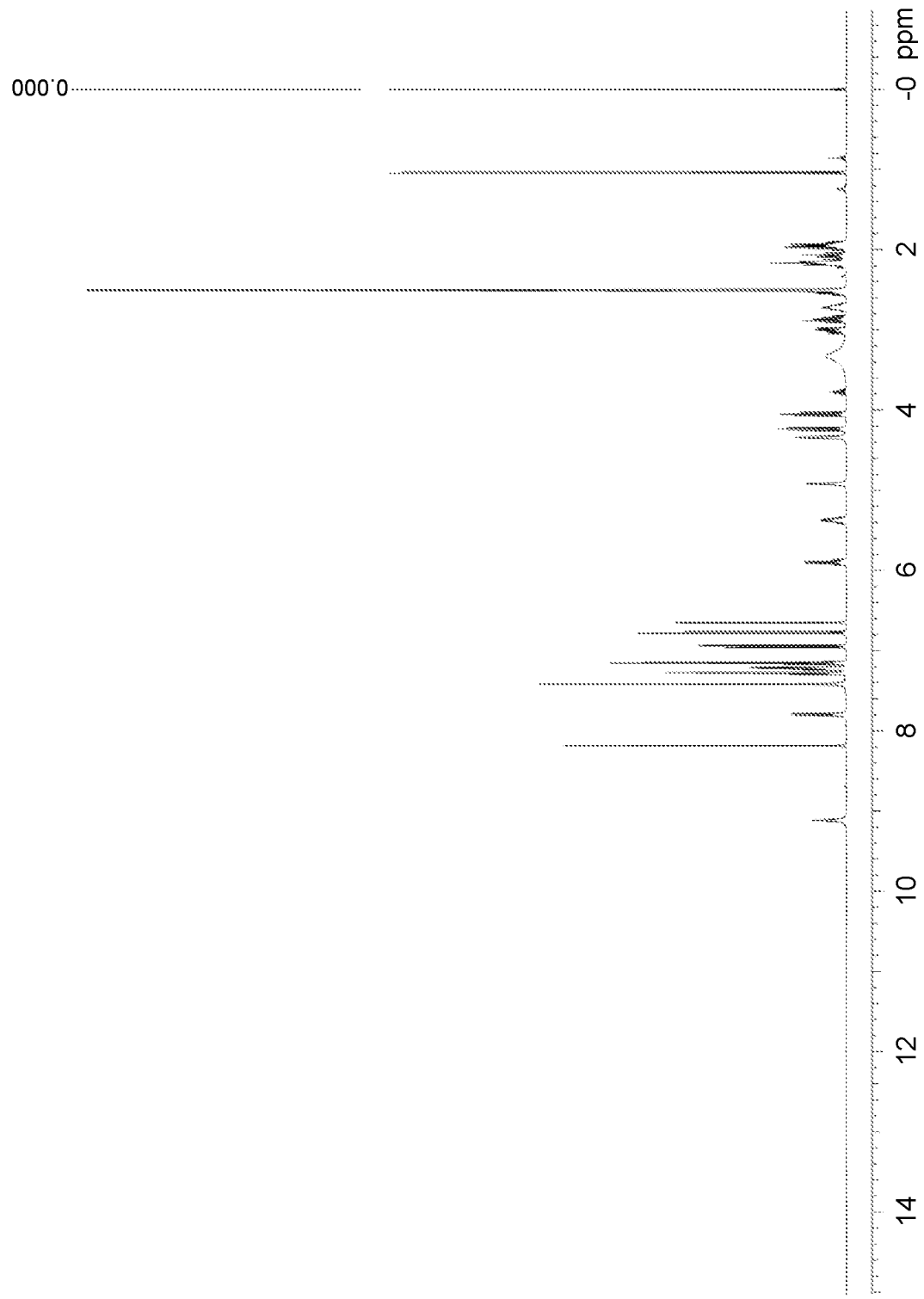
FIG. 30 is a ¹H-NMR of cocrystal Form N which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and gentisic acid.

FIG. 30 shows a $^1$H-NMR of cocrystal Form N. The $^1$H-NMR indicates that the stoichiometric ratio of MLN4924:gentisic acid:isopropanol is 1:1:0.2 and cocrystal Form N is a gentisic acid cocrystal isopropanol solvate. In one embodiment, the cocrystal is characterized by a $^1$H-NMR substantially similar to FIG. 30.

In one embodiment, the cocrystal is characterized by both of the following features (I-i) and (I-ii):
(I-i) an XRPD pattern having peaks at 2θ angles of 8.9°, 17.9°, and 22.3°±0.2°; and
(I-ii) a $^1$H-NMR substantially similar to FIG. 30.

In one embodiment, the cocrystal is cocrystal Form N, which is characterized by one or more of the following features: an XRPD pattern as shown in FIG. 29 or a $^1$H-NMR substantially similar to FIG. 30.

In one embodiment, the cocrystal is a cocrystal of ((1S, 2S,4R)-4-{4-[(1S)-2,3-dihydro-1H-inden-1-ylamino]-7H-pyrrolo[2,3-d]pyrimidin-7-yl}-2-hydroxycyclopentyl) methyl sulfamate and malonic acid. In one embodiment, the cocrystal is anhydrous mon-malonic acid cocrystal.

In one embodiment, the cocrystal is characterized by an XRPD pattern having peaks at 2θ angles of 3.66°, 19.24°, and 25.14°+0.2°. In one embodiment, the cocrystal is characterized by an XRPD pattern having peaks at 2θ angles of 3.66°, 10.21°, 19.24°, 24.87°, and 25.14°±0.2°. In another embodiment, the cocrystal is characterized by an XRPD pattern as shown in FIG. 22.

Figure 22:
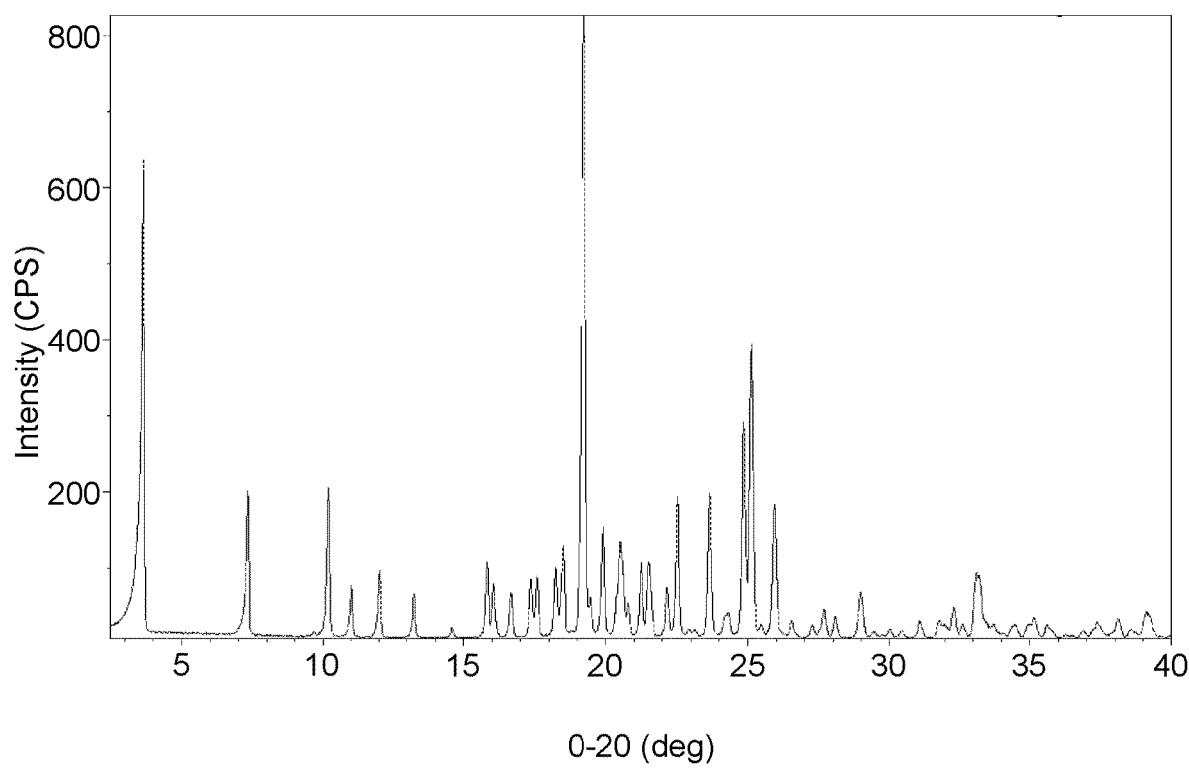
FIG. 22 is an XRPD pattern of cocrystal Form M which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and malonic acid.

FIG. 22 shows an X-ray powder diffraction (XRPD) pattern of cocrystal Form M obtained using Cu-Kα radiation. Peaks identified in FIG. 22 include those listed in Table 15.

TABLE 15

| Diffraction angle | d spacing (Å) |
| --- | --- |
| 3.66 ± 0.20 | 24.132 ± 1.394 |
| 7.34 ± 0.20 | 12.047 ± 0.337 |
| 10.21 ± 0.20 | 8.662 ± 0.173 |
| 19.24 ± 0.20 | 4.614 ± 0.048 |
| 22.53 ± 0.20 | 3.947 ± 0.035 |
| 23.66 ± 0.20 | 3.760 ± 0.032 |
| 24.87 ± 0.20 | 3.581 ± 0.029 |
| 25.14 ± 0.20 | 3.543 ± 0.028 |
| 25.95 ± 0.20 | 3.433 ± 0.026 |

Table 16 shows the unit cell parameters of cocrystal Form M derived from the corresponding indexed XRPD data. In one embodiment, the cocrystal exhibits crystal parameters that are approximately equal to the following: a=5.634 Å, b=9.275 Å, c=48.091 Å, α=90°, β=90°, γ=90°, volume=2513.0 Å$^3$/cell, and space group=P2$_1$2$_1$2$_1$ (19), and with chiral contents.

TABLE 16

| | MLN4924 saccharin |
| --- | --- |
| Bravais Type | Primitive Orthorhombic |
| a [Å] | 5.634 |
| b [Å] | 9.275 |
| c [Å] | 48.091 |
| α [deg] | 90 |
| β [deg] | 90 |
| γ [deg] | 90 |
| Volume [Å$^3$/cell] | 2513.0 |
| Chiral Contents ? | Chiral |
| Extinction Symbol | P 21 21 21 |
| Space Group(s) | P2$_1$2$_1$2$_1$ (19) |
| Source | Manual Input |

Figure 23:
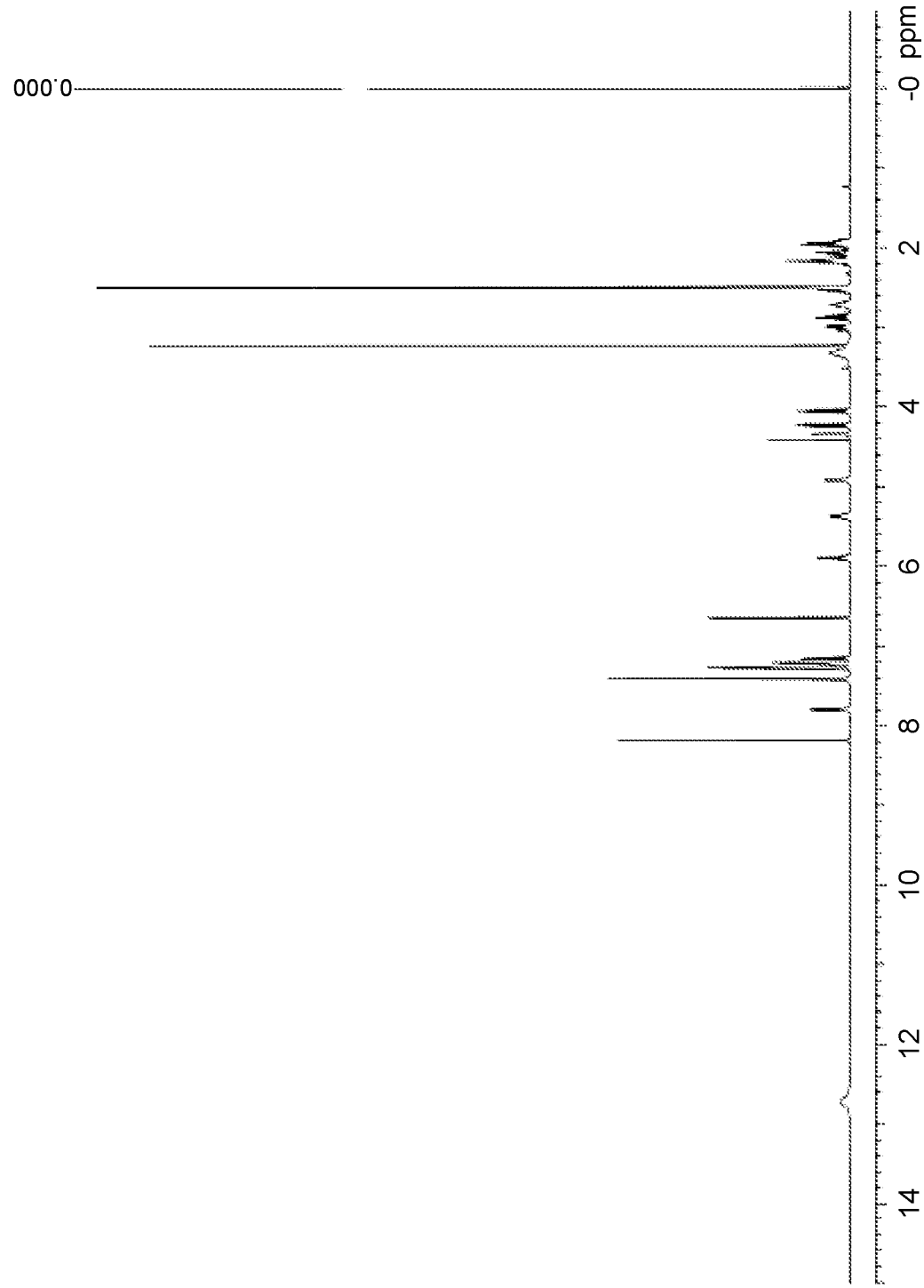
FIG. 23 is a ¹H-NMR of cocrystal Form M which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and malonic acid.

FIG. 23 shows a $^1$H-NMR of cocrystal Form M. The $^1$H-NMR indicates that the stoichiometric ratio of MLN4924 to malonic acid is 1:1 and cocrystal Form M is anhydrous mono-malonic acid cocrystal. In one embodiment, the cocrystal is characterized by a $^1$H-NMR substantially similar to FIG. 23.

Figure 24:
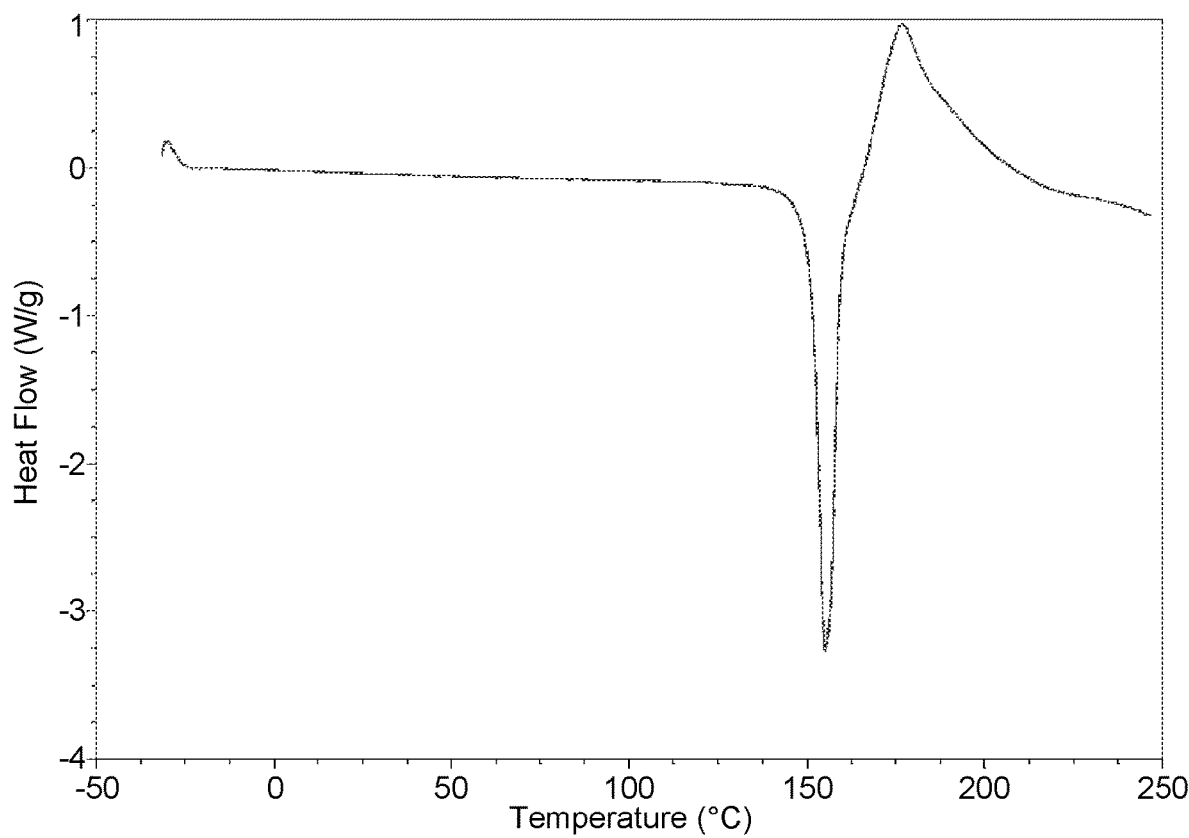
FIG. 24 is a differential scanning calorimetry (DSC) profile for cocrystal Form M which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and malonic acid.

FIG. 24 shows a differential scanning calorimetry profile (DSC) of cocrystal Form M. The DSC graph plots the heat flow as a function of temperature from a sample, the temperature rate change being about 10° C./min. In one embodiment, the cocrystal is characterized by a DSC profile characterized by an endothermic peak at about 155.1° C. In another embodiment, the cocrystal is characterized by a DSC profile as shown in FIG. 24.

Figure 25:
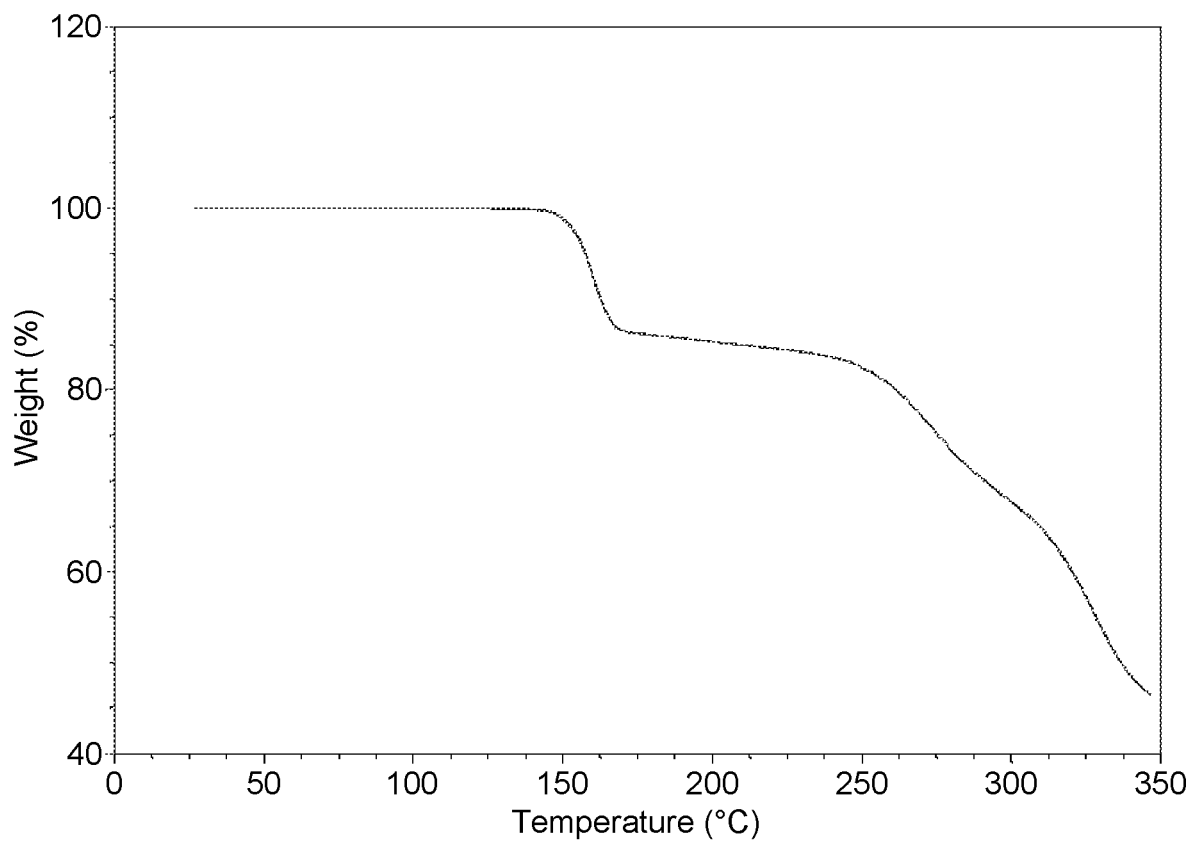
FIG. 25 is a thermal gravimetric analysis (TGA) profile for cocrystal Form M which is a cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and malonic acid.

FIG. 25 shows a thermal gravimetric analysis (TGA) profile of cocrystal Form M. The TGA profile plots the percent loss of weight of the sample as a function of temperature, the temperature rate change being about 10° C./min. In one embodiment, the cocrystal is characterized by a TGA characterized by an about 14.0 wt % loss between about 135° C. and about 184° C. In another embodiment, the cocrystal is characterized by a TGA profile as shown in FIG. 25.

In one embodiment, the cocrystal is characterized by at least two of the following features (I-i)-(I-iv):
(I-i) an XRPD pattern having peaks at 2θ angles of 3.66°, 19.24°, and 25.14°+0.2°;
(I-ii) a $^1$H-NMR substantially similar to FIG. 23;
(I-iii) a DSC profile as shown in FIG. 24; or
(I-iv) a TGA profile as shown in FIG. 25.

In one embodiment, the cocrystal is cocrystal Form M, which is characterized by one or more of the following features: an XRPD pattern as shown in FIG. 22, a $^1$H-NMR substantially similar to FIG. 23, a DSC profile as shown in FIG. 24, or a TGA profile as shown in FIG. 25.

Other embodiments of the invention are directed to cocrystal forms of MLN4924 characterized by a combination of the aforementioned characteristics of any of the crystalline forms discussed herein. The characterization may be by any combination of one or more of the XRPD, TGA, and DSC, described for a particular polymorph. For example, a cocrystal form of MLN4924 may be characterized by any combination of the XRPD results regarding the position of the major peaks in a XRPD scan; and/or any combination of one or more of the cell parameters derived from data obtained from a XRPD scan. A cocrystal form of MLN4924 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of anhydrous cocrystal of MLN4924 as determined by water sorption/desorption measurements over a range of relative humidity (e.g., 0% to 90%) may also characterize a cocrystal form of MLN4924.

Examples of combinations of cocrystal form characterizations using multiple analytical techniques include the location of at least one of the major peaks of a XRPD scan and the temperature associated with the maximum heat flow during one or more heat flow transitions observed by a corresponding DSC measurement; the location of at least one of the major peaks of a XRPD scan and one or more weight losses associated with a sample over a designated temperature range in a corresponding TGA measurement; the location of at least one of the major peaks of a XRPD scan, the temperature associated with the maximum heat flow during one or more heat flow transitions observed by a corresponding DSC measurement, and one or more weight losses associated with a sample over a designated temperature range in a corresponding TGA measurement; and the location of at least one of the major peaks of a XRPD scan, the temperature associated with the maximum heat flow during one or more heat flow transitions observed by a corresponding DSC measurement, one or more weight losses associated with a sample over a designated temperature range in a corresponding TGA measurement, and the change in sorption/desorption of water per molecule of anhydrous salt as determined by water sorption/desorption measurements over a range of relative humidity. As well, each of the aforementioned examples may replace the use of the location of at least one of the major peaks of a XRPD scan with one or more cell parameters of the cocrystal form.

The combinations of characterizations that are discussed above may be used to describe any of the cocrystal forms discussed herein.

Pharmaceutical Compositions and Methods

The compound of formula (I) (MLN4924), or a crystalline form thereof, or a solvate thereof, or a cocrystal form, is a useful inhibitor of E1 enzyme activity. In particular, a cocrystal form of MLN4924 is designed to be an inhibitor of NAE, UAE, and/or SAE. An inhibitor is meant to include compounds which reduce the promoting effects of E1 enzymes in ubl conjugation to target proteins (e.g., reduction of ubiquitination, neddylation, sumoylation), reduce intracellular signaling mediated by ubl conjugation, and/or reduce proteolysis mediated by ubl conjugation (e.g., inhibition of cullin-dependent ubiquitination and proteolysis (e.g., the ubiquitin-proteasome pathway)). Thus, a cocrystal form of MLN4924 may be assayed for its ability to inhibit the E1 enzyme in vitro or in vivo, or in cells or animal models according to methods provided in further detail herein, or methods known in the art. A cocrystal form of MLN4924 may be assessed for its ability to bind or mediate E1 enzyme activity directly. Alternatively, the activity of a cocrystal form of MLN4924 may be assessed through indirect cellular assays, or assays measuring downstream effects of E1 activation to assess inhibition of downstream effects of E1 inhibition (e.g., inhibition of cullin-dependent ubiquitination and proteolysis). For example, activity may be assessed by detection of ubl-conjugated substrates (e.g., ubl-conjugated E2s, neddylated cullins, ubiquitinated substrates, sumoylated substrates); detection of downstream protein substrate stabilization (e.g., stabilization of p27, stabilization of IκB); detection of inhibition of UPP activity; detection of downstream effects of protein E1 inhibition and substrate stabilization (e.g., reporter assays, e.g., NFκB reporter assays, p27 reporter assays). Assays for assessing activities are known in the art.

One embodiment of this invention relates to a pharmaceutical composition comprising a cocrystal form of MLN4924, and a pharmaceutically acceptable carrier or diluent. The pharmaceutical compositions preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include, but are not limited to, ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as, but not limited to, an oil, water, an alcohol, and combinations of these. Solubilizing agents such as cyclodextrins including beta-cyclodextrin sulfobutylether and hydroxypropyl beta-cyclodextrin may be included. Other excipients present in the formulation include citric acid or sodium citrate. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes; e.g., to mask taste, to affect the site of dissolution or absorption, or to prolong drug action. Coatings may be applied to a tablet or to granulated particles for use in a capsule.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). Preferably, the composition is formulated for administration to a patient having or at risk of developing or experiencing a recurrence of the relevant disorder being treated. The term "patient", as used herein, means an animal, preferably a mammal, more preferably a human. Preferred pharmaceutical compositions are those formulated for oral, intravenous, or subcutaneous administration. However, any of the above dosage forms containing a therapeutically effective amount of a compound are well within the bounds of routine experimentation and therefore, well within the scope of the instant invention. In certain embodiments, the pharmaceutical composition may further comprise another therapeutic agent. Preferably, such other therapeutic agent is one normally administered to patients with the disorder, disease or condition being treated.

By "therapeutically effective amount" is meant an amount of compound or composition sufficient, upon single or multiple dose administration, to cause a detectable decrease in E1 enzyme activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of E1 enzyme inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

One embodiment relates to a method of inhibiting or decreasing E1 enzyme activity in a sample comprising contacting the sample with a cocrystal form of MLN4924, or a composition comprising a cocrystal form of MLN4924. The sample, as used herein, includes, without limitation, sample comprising purified or partially purified E1 enzyme, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of E1 enzyme activity in a sample may be carried out in vitro or in vivo, in cellulo, or in situ.

In another embodiment, the invention provides a method for treating a patient having a disorder, a symptom of a disorder, at risk of developing, or experiencing a recurrence of a disorder, comprising administering to the patient a pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Disease applications include those disorders in which inhibition of E1 enzyme activity is detrimental to survival and/or expansion of diseased cells or tissue (e.g., cells are sensitive to E1 inhibition; inhibition of E1 activity disrupts disease mechanisms; reduction of E1 activity stabilizes protein which are inhibitors of disease mechanisms; reduction of E1 activity results in inhibition of proteins which are activators of disease mechanisms). Disease applications are also intended to include any disorder, disease or condition which requires effective cullin and/or ubiquitination activity, which activity can be regulated by diminishing E1 enzyme activity (e.g., NAE, UAE activity).

For example, methods are useful in treatment of disorders involving cellular proliferation, including, but not limited to, disorders which require an effective cullin-dependent ubiquitination and proteolysis pathway (e.g., the ubiquitin proteasome pathway) for maintenance and/or progression of the disease state. The methods are useful in treatment of disorders mediated via proteins (e.g., NFκB activation, $p27^{Kip}$ activation, $p21^{WAF/CIP1}$ activation, p53 activation) which are regulated by E1 activity (e.g., NAE activity, UAE activity, SAE activity). Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neurone disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

A cocrystal form of MLN4924 and pharmaceutical compositions are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Non-limiting examples of solid tumors that can be treated by the methods include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); chronic myelomonocytic leukemia (CMML); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the compound or composition is used to treat a patient having or at risk of developing or experiencing a recurrence in a cancer selected from the group consisting of colorectal cancer, ovarian cancer, lung cancer, breast cancer, gastric cancer, prostate cancer, and pancreatic cancer. In certain preferred embodiments, the cancer is selected from the group consisting of lung cancer, colorectal cancer, ovarian cancer and hematologic cancers.

Depending on the particular disorder or condition to be treated, in some embodiments, the E1 enzyme inhibitor is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated". The other therapeutic agent may be administered prior to, at the same time as, or following administration of the E1 inhibitor.

In some embodiments, a cocrystal form of MLN4924 or pharmaceutical compositions containing a cocrystal form of MLN4924 are administered in conjunction with a therapeutic agent selected from the group consisting of cytotoxic agents, radiotherapy, and immunotherapy appropriate for treatment of proliferative disorders and cancer. Non-limiting examples of cytotoxic agents suitable for use in combination with the E1 enzyme inhibitors include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs including, e.g., CC-5013 and CC-4047; protein tyrosine kinase inhibitors, including, e.g., imatinib mesylate and gefitinib; proteasome inhibitors, including, e.g., bortezomib; antibodies, including, e.g., trastuzumab, rituximab, cetuximab, and bevacizumab; mitoxantrone; dexamethasone; prednisone; and temozolomide.

Other examples of agents the cocrystal form of MLN4924 or pharmaceutical compositions containing a cocrystal form of MLN4924 may be combined with include anti-inflammatory agents such as corticosteroids, TNF blockers, Il-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

Methods of Preparing Cocrystal Forms

In some embodiments, a cocrystal form of MLN4924 can be synthesized by cooling a solution containing dissolved MLN4924 and a coformer prepared at a specified elevated temperature. In some other embodiments, the solution is allowed to cool down to room or subambient temperature either by turning the heating device off while keeping the sample in the oil bath or on the hot plate or by removing the sample from the oil bath or hot plate. Solids were collected by vacuum filtration and analyzed.

In some embodiments, a cocrystal form of MLN4924 can be synthesized by slurrying a suspension of MLN4924 and a coformer prepared by adding solvent such that excess solids remained. The resulting mixture is then agitated in a sealed vial at the specified temperature. After a given amount of time, the solids are isolated by vacuum filtration.

In some embodiments, a cocrystal form of MLN4924 can be synthesized by solvent assisted grinding. Samples of MLN4924 and coformer are transferred to agate milling containers. An agate milling ball is added to the container and, a small amount of solvent is added. The milling container is then attached to a Retsch mill. The samples are milled for specific time periods at 20 Hz or 30 Hz, and the solids are scraped down the walls of the jars between milling periods. The resulting solids are transferred to clean vials and analyzed.

In some embodiments, a cocrystal form of MLN4924 can be synthesized by solvent/anti-solvent precipitation. Solutions of MLN4924 and coformers are prepared in various solvents. An excess of an anti-solvent is added to the solution to precipitate solids. Solids are allowed to slurry at the listed time period prior to isolation by vacuum filtration.

In some embodiments, a cocrystal form of MLN4924 can be synthesized by vapor diffusion. Solutions of MLN4924 and coformer are prepared in specified solvents in small vials. The small vial is left uncapped and placed into a larger vial containing an anti-solvent. The larger vial is capped to allow vapor diffusion to occur. Solids are collected by vacuum filtration prior to analysis.

In one embodiment, a method for the preparation of cocrystal Form A, comprises:
  a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of acetone to obtain a 0.08 M to 0.1 M solution;
  b) adding a 0.08 M to 0.1 M solution of glycolic acid in a solvent system of 2:1 to 4:1 MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:glycolic acid;
  c) adding ethyl acetate at 0.5 to 1.5 times of the amount of acetone in step a) to the solution from step b);
  d) evaporating the solvent system from step c) at 15-35° C. for a suitable period of time;
  e) adding a solvent system of ethyl acetate:ethanol of a ratio between 80:20 and 95:5 at 1.5 to 3.5 times of the amount of acetone in step a) to the residue from step d);
  f) evaporating the solvent system from step e) at 15-35° C. for a suitable period of time; and
  g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form A, comprises:
  a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:glycolic acid in a suitable amount of isopropyl acetate to obtain a suspension of 0.05 to 0.15 M of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in isopropyl acetate;
  b) slurrying the suspension from step a) at 15-55° C. for a suitable period of time;
  c) collecting the solid produced from step b); and
  d) drying the solid from step c) in air at room temperature for a suitable period of time.

In one embodiment, the suitable period of time in step b) is about 1 day to about 3 days.

In another embodiment, a method for the preparation of cocrystal Form A, comprises:
  a) preparing a solution of about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:glycolic acid in a suitable amount of acetone;
  b) allowing vapor diffusion with methyl tert-butyl ether to occur to the solution from step a) at room temperature; and
  c) collecting the solid produced from step b).

In one embodiment, a method for the preparation of cocrystal Form C, comprises:
  a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of hexafluoroisopropanol to obtain a 0.08 M to 0.1 M solution;
  b) adding a 0.08 M to 0.1 M solution of glycolic acid in a solvent system of 2:1 to 4:1 MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:glycolic acid;
  c) adding toluene at 0.5 to 1.5 times of the amount of hexafluoroisopropanol in step a) to the solution from step b);
  d) evaporating the solvent system from step c) under ambient conditions for a suitable period of time;
  e) adding a solvent system of ethyl acetate:ethanol of a ratio between 80:20 and 95:5 at 1.5 to 3.5 times of the amount of hexafluoroisopropanol in step a) to the residue from step d);
  f) evaporating the solvent system from step e) at 15-35° C. for a suitable period of time; and
  g) collecting the solid produced from step f).

In one embodiment, the suitable period of time in step d) is about 2 days to about 4 days. In another embodiment, the suitable period of time in step f) is about 1 day to about 3 days.

In one embodiment, a method for the preparation of cocrystal Form B, comprises:
  a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of acetone to obtain a 0.08 M to 0.1 M solution;
  b) adding a 0.08 M to 0.1 M solution of hippuric acid in MeOH to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid;
  c) adding ethyl acetate at 0.5 to 1.5 times of the amount of acetone in step a) to the solution from step b);
  d) evaporating the solvent system from step c) at 15-35° C. for a suitable period of time;
  e) adding a solvent system of ethyl acetate:ethanol of a ratio between 80:20 and 95:5 at 1.5 to 3.5 times of the amount of acetone to the residue from step d);
  f) evaporating the solvent system from step e) at 15-35° C. for a suitable period of time; and
  g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form B, comprises:
  a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of methanol to obtain a 0.08 M to 0.1 M solution;
  b) adding a 0.08 M to 0.1 M solution of hippuric acid in MeOH to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid;

c) adding isopropyl ether at 0.5 to 1.5 times of the amount of methanol in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of methanol in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form B, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of hexafluoroisopropanol to obtain a 0.08 M to 0.1 M solution;
b) adding a 0.08 M to 0.1 M solution of hippuric acid in MeOH to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid;
c) adding water at 0.5 to 1.5 times of the amount of hexafluoroisopropanol in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of hexafluoroisopropanol in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form B, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of tetrahydrofuran to obtain a 0.08 M to 0.1 M solution;
b) adding a 0.08 M to 0.1 M solution of hippuric acid in MeOH to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid;
c) adding heptane at 0.5 to 1.5 times of the amount of tetrahydrofuran in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of tetrahydrofuran in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form B, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid in a suitable amount of solvent system of 2:1 to 8:1 p-dioxane:ethanol to obtain a mixture of 0.2 to 0.36 M of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in p-dioxane:ethanol;
b) stirring the mixture from step a) at room temperature for a suitable period of time to obtain a solution;
c) adding heptane at 2 to 6 times of the amount of p-dioxane:ethanol in step a) to the solution from step b);
d) slurrying the mixture from step c) at room temperature for a suitable period of time;
e) collecting the solid produced from step d); and
f) drying the solid from step e) in air at room temperature for a suitable period of time.

In one embodiment, the suitable period of time in step d) is about 0.5 day to about 1.5 days.

In another embodiment, a method for the preparation of cocrystal Form B, comprises:
a) dissolving 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:hippuric acid in a suitable amount of solvent system of 2:1 to 8:1 p-dioxane:ethanol;
b) slurrying the mixture from step a) at room temperature for a suitable period of time;
c) adding a suitable amount of ethanol to the suspension from step b);
d) stirring the mixture from step c) at room temperature for a suitable period of time;
e) keeping the mixture from step d) frozen for a suitable period of time;
f) adding a suitable amount of heptane to the mixture from step e);
g) stirring the mixture from step f) at room temperature for a suitable period of time; and
h) collecting the solid produced from step g).

In one embodiment, the suitable period of time in step b) is about 2 days to about 4 days. In another embodiment, the suitable period of time in step d) is about 0.5 day to about 1.5 days. In another embodiment, the suitable period of time in step e) is about 1 day to about 3 days. In another embodiment, the suitable period of time in step g) is about 0.5 day to about 1.5 days.

In one embodiment, a method for the preparation of cocrystal Form D, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of acetone to obtain a 008 M to 0.1 M solution;
b) adding a 0.08 M to 0.1 M solution of L-proline in a solvent system of 2:1 to 4:1 MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:L-proline;

c) adding ethyl acetate at 0.5 to 1.5 times of the amount of acetone in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of acetone in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form D, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of methanol to obtain a 0.08 M to 0.1 M solution; b) adding a 0.08 M to 0.1 M solution of L-proline in a solvent system of 2:1 to 4:1 MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:L-proline;
c) adding isopropyl ether at 0.5 to 1.5 times of the amount of methanol in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of methanol in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form D, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of hexafluoroisopropanol to obtain a 0.08 M to 0.1 M solution;
b) adding a 0.08 M to 0.1 M solution of L-proline in a solvent system of 2:1 to 4:1 MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:L-proline;
c) adding toluene at 0.5 to 1.5 times of the amount of hexafluoroisopropanol in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of hexafluoroisopropanol in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form D, comprises:
a) dissolving ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in a suitable amount of tetrahydrofuran to obtain a 0.08 M to 0.1 M solution;
b) adding a 0.08 M to 0.1 M solution of L-proline in a solvent system of MeOH:water to the solution from step a) at about 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:L-proline;
c) adding heptane at 0.5 to 1.5 times of the amount of tetrahydrofuran in step a) to the solution from step b);
d) evaporating the solvent system from step c) at 15-35° C. for a suitable period of time;
e) adding a solvent system of ethyl acetate:ethanol of a ratio between 80:20 and 95:5 at 1.5 to 3.5 times of the amount of tetrahydrofuran in step a) to the residue from step d);
f) evaporating the solvent system from step e) at 15-35° C. for a suitable period of time; and
g) collecting the solid produced from step f).

In one embodiment, the suitable period of time in step d) is about 2 days to about 4 days. In another embodiment, the suitable period of time in step f) is about 1 day to about 3 days.

In another embodiment, a method for the preparation of cocrystal Form D, comprises:
a) preparing a solution of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and L-proline at about 1:2 to 2:1 molar ratio in a suitable amount of solvent system of THF:MeOH:water:EtOAc;
b) evaporating the solvent system at 15-35° C. or under a nitrogen stream for a suitable period of time; and
c) drying the residue from step b) in the vacuum oven at room temperature for a suitable period of time.

In one embodiment, the suitable period of time in step c) is about 0.5 day to about 1.5 days.

In another embodiment, a method for the preparation of cocrystal Form D, comprises:
a) preparing a solution of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and L-proline at about 1:2 to 2:1 molar ratio in a suitable amount of solvent system of acetone:MeOH:water:EtOAc;
b) evaporating the solvent system at 15-35° C. for a suitable period of time; and
c) drying the residue from step b) in the vacuum oven at room temperature for a suitable period of time.

In one embodiment, the suitable period of time in step c) is about 0.5 to about 1.5 days.

In one embodiment, a method for the preparation of cocrystal Form F, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:saccharin in a suitable amount of ethanol at room temperature to obtain a mixture of 0.1 to 0.2 M of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in ethanol;
b) stirring the mixture from step a) at room temperature for a suitable period of time;
c) adding additional ethanol at 12% to 32% of the amount of ethanol in step a) to the suspension from step b);
d) stirring the mixture from step c) at room temperature for a suitable period of time;
e) collecting the solid produced from step d); and
f) drying the solid from step e) in air at room temperature for a suitable period of time.

In one embodiment, the suitable period of time in step b) is about 0.5 day to about 1.5 days. In another embodiment, the suitable period of time in step d) is about 0.5 day to about 1.5 days.

In another embodiment, a method for the preparation of cocrystal Form F, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:saccharin in a suitable amount of ethanol;
b) stirring the suspension from step a) at room temperature for a suitable period of time;
c) collecting the solid produced from step b).

In one embodiment, the suitable period of time in step b) is about 1 day to about 3 days.

In another embodiment, a method for the preparation of cocrystal Form F, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:saccharin in a suitable amount of ethyl acetate at 62-82° C. to obtain a suspension;
b) stirring the suspension from step a) at 62-82° C. for a suitable period of time;
c) cooling the suspension from step b) to room temperature;
d) stirring the suspension from step c) at room temperature for a suitable period of time; and
e) collecting the solid produced from step d).

In one embodiment, the suitable period of time in step b) is about 10 minutes to about 50 minutes. In another embodiment, the suitable period of time in step d) is about 2 days to about 4 days.

In another embodiment, a method for the preparation of cocrystal Form F, comprises:
a) transferring ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate and saccharin at about 1:2 to 2:1 molar ratio to an agate milling container;
b) adding one or more agate milling balls to the container;
c) adding a suitable amount of isopropyl alcohol to the container;
d) milling the mixture form step c) for time periods at 10-40 Hz; and
e) collecting the solid produced from step d).

In one embodiment, a method for the preparation of cocrystal Form G, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:piperazine in a suitable amount of acetonitrile to obtain a mixture of 0.06 to 0.18 M of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in acetonitrile;
b) heating the mixture from step a) at 62-82° C. to obtain a solution;
c) stirring the solution from step b) at 62-82° C. for a suitable period of time;
d) cooling the solution from step c) to room temperature;
e) stirring the mixture from step d) at room temperature for a suitable period of time; and
f) collecting the solid produced from step e).

In one embodiment, the suitable period of time in step c) is about 10 minutes to about 50 minutes. In another embodiment, the suitable period of time in step e) is about 0.5 day to about 1.5 days.

In one embodiment, a method for the preparation of cocrystal Form H, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:gentisic in a solvent system of 20:1 to 40:1 nitromethane:EtOH at a suitable amount;
b) heating the mixture from step a) at 60-80° C. for a suitable period of time to obtain a solution;
c) cooling the solution from step b) to room temperature;
d) stirring the mixture from step c) at room temperature for a suitable period of time;
e) sonicating the mixture from step d) for a suitable amount of time;
f) keeping the mixture from step e) at 0-30° C. for a suitable period of time;
g) collecting the solid produced from step f); and
h) drying the solid in air at room temperature for a suitable period of time.

In one embodiment, the suitable period of time in step d) is about 1 day to about 3 days. In another embodiment, the suitable period of time in step f) is about 12 days to about 16 days. In another embodiment, the suitable period of time in step h) is about 2 days to about 4 days.

In one embodiment, a method for the preparation of cocrystal Form J, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:gentisic in a suitable amount of acetonitrile;
b) heating the mixture from step a) at 62-82° C. for a suitable period of time to obtain a solution;
c) stirring the solution from step b) at 62-82° C. for a suitable period of time;
d) cooling the solution from step c) to room temperature;
e) stirring the mixture from step d) at room temperature for a suitable period of time;
f) adding additional suitable amount of acetonitrile to the mixture for step e);
g) stirring the mixture from step f) at room temperature for a suitable period of time; and
h) collecting the solid produced from step g).

In one embodiment, the suitable period of time in step c) is about 5 minutes to about 25 minutes. In another embodiment, the suitable period of time in step e) is about 1 day to about 3 days. In another embodiment, the suitable period of time in step g) is about 10 minutes to about 50 minutes.

In one embodiment, a method for the preparation of cocrystal Form L, comprises:
a) drying cocrystal Form J in vacuum oven at 28-48° C. for a suitable period of time; and
b) collecting the solid produced from step a).

In one embodiment, the suitable period of time in step a) is about 0.5 day to about 1.5 days.

In one embodiment, a method for the preparation of cocrystal Form N, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:gentisic in a suitable amount of isopropanol;
b) heating the mixture from step a) at 62-82° C. for a suitable period of time to obtain a solution;
c) cooling the solution from step b) to room temperature;
d) stirring the mixture from step c) at room temperature for a suitable period of time;
e) evaporating the solvent system from step d) to a suitable amount of volume;
f) keeping the mixture from step e) at −14 to −22° C. a suitable period of time;
g) adding a suitable amount of heptane to the mixture form step f);
h) keeping the mixture from step g) at −14 to −22° C. for a suitable period of time;
i) collecting the solid produced from step h); and
j) drying the solid in air at room temperature for a suitable period of time.

In one embodiment, the suitable period of time in step d) is about 0.5 day to about 1.5 days. In another embodiment, the suitable period of time in step f) is about 2 days to about 4 days.

In one embodiment, a method for the preparation of cocrystal Form M, comprises:
a) dispensing 1:2 to 2:1 molar ratio of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate:malonic acid in a suitable amount of nitromethane to obtain a mixture of 0.06 to 0.18 M of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate in nitromethane;
b) heating the mixture from step a) at 75-95° C. for a suitable period of time;
c) cooling the mixture from step b) to room temperature;
d) stirring the suspension from step c) at room temperature for a suitable period of time;
e) collecting the solid produced from step d); and
f) drying the solid from step e) in air at room temperature for a suitable period of time.

In one embodiment, the suitable period of time in step b) is about 10 minutes to about 50 minutes. In another embodiment, the suitable period of time in step d) is about 0.5 day to about 1.5 days.

EXAMPLES

Abbreviations

ACN Acetonitrile
DCM Dichloromethane
DMF Dimethylformamide
DMSO Dimethylsulfoxide
EtOH Ethanol
EtOAc Ethyl acetate
HFIPA Hexafluoroisopropanol
IPA Isopropanol
IPE Isopropyl ether
MeOH Methanol
MTBE Methyl tert-butyl ether
NMP n-Methylpyrrolidone
TFA Trifluoroacetic acid
THF Tetrahydrofuran
TFE 2,2,2-trifluoroethanol
SC Slow cool
SE Slow evaporation
FC Fast cool
FE Fast evaporation
VD Vapor diffusion
API Active pharmaceutical ingredient (MLN4924)
b/e Birefringence/extinction
eq. Equivalent
ppt Precipitation
RRT Relative Retention Time
RT Room (ambient) temperature
RH Relative humidity
VF Vacuum filter
VO Vacuum oven
DSC Differential scanning calorimetry
$^1$H NMR Proton nuclear magnetic resonance spectroscopy
HPLC High performance liquid chromatography
TGA Thermogravimetric analysis
XRPD X-ray powder diffraction General Methods Crystallization Techniques: 96-Well Plate: API stock solutions were prepared at ~45 mg/mL in acetone, HFIPA, MeOH, and THF and dispensed into a 96-well plate. Coformer solutions, prepared at 0.1M concentration in methanol or methanol:water mixtures, were added at 1:1 or 2:1 API:coformer ratio. A small amount of antisolvent (ethyl acetate, heptane, IPE, toluene, or water) was also added to each well. Wells were covered with aluminum foil and a small hole placed in each well to allow for slow evaporation. The majority of the wells were observed to be oils after ~3 days of evaporation. 100 µL of 90:10 ethyl acetate:ethanol was added to each well and the plate was sonicated. Plate was again covered with aluminum foil with pinholes for each well and allowed to slowly evaporate. After ~2 days, the solvent was evaporated and the plate was analyzed by XRPD.

Computational Methods: Indexed XRPD Data: XRPD patterns were indexed using X-Pert High Score Plus (v.2.2.1) or proprietary SSCI software (Triads v 1.0). Successful indexing of a pattern indicates that the sample is composed primarily of a single crystalline phase. Space groups consistent with the assigned extinction symbol, unit cell parameters, and derived quantities are tabulated in the respective figures providing the indexing solution for each form. To confirm the tentative indexing solution, the molecular packing motifs within the crystallographic unit cells must be determined. No attempts at molecular packing were performed.

X-ray Powder Diffraction Peak Identification Process: The data contain X-ray diffraction patterns with labeled peaks and tables with peak lists. Peak labels in the image are meant as a visual aid. Accurate peak positions are listed in the tables. Under most circumstances, peaks within the range of up to about 30° (2θ) were selected. Rounding algorithms were used to round each peak to the nearest 0.1° or 0.01° (2θ), depending upon the instrument used to collect the data and/or the inherent peak resolution. The location of the peaks along the horizontal axis, ° (2θ), in both the figures and the tables were automatically determined using proprietary software and rounded to one or two significant figures after the decimal point based upon the above criteria. Peak position variabilities are given to within ±0.2° (2θ) based upon recommendations outlined in the USP discussion of variability in X-ray powder diffraction. The accuracy and precision associated with any particular measurement reported herein has not been determined. To calculate d-spacings, the wavelength used was 1.541874 Å, a weighted average of the Cu-Kα1 and Cu-Kα2 wavelengths. Variability associated with d-spacing estimates was calculated from the USP recommendation, at each d-spacing, and provided in the respective data tables. Per USP guidelines, variable hydrates and solvates may display peak variances greater than 0.2° (2θ) and therefore peak variances of 0.2° (2θ) are not applicable to these materials. For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity.

Nuclear Magnetic Resonance Spectroscopy (NMR): Samples were prepared in deuterated dimethyl sulfoxide (DMSO). The specific acquisition parameters are listed on the plot of the first spectrum displayed in the data section. The solution NMR spectra were acquired at ambient temperature with a Varian$^{UNITY}$INOVA-400 spectrometer at 400 MHz. For $^1$H-NMR, the spectra were referenced to internal tetramethylsilane (TMS) at 0.0 ppm.

Differential Scanning Calorimetry (DSC): DSC analysis was performed using a TA Instruments differential scanning calorimeter Q2000 or 2920. The sample was placed into an aluminum DSC pan, its weight accurately recorded. In most analysis the lid was hermetically sealed and perforated with a laser pinhole. In one case a Tzero crimped pan was utilized. The sample cell was equilibrated at −30° C. and heated under a nitrogen purge at a rate of 10° C./min, up to final temperature of 250° C. or 260° C. Indium metal was used as the calibration standard.

Thermal Gravimetric Analysis (TGA): TGA analyses were performed using a TA Instruments 2950 thermogravimetric analyzer. Temperature calibration was performed using nickel and Alumel™. Each sample was placed in an aluminum or platinum pan and then inserted into the TG furnace. The furnace was heated under nitrogen.

High Performance Liquid Chromatography (HPLC): HPLC analyses were performed using an Agilent 1100 series liquid chromatograph equipped with a variable wavelength detector and binary pump for sequence file 552094, and a diode array detector and quaternary pump for the remaining sequences. Configurations differ due to instrument availability at the time of assay. Degasser and an autosampler (set to ~5° C.) were equipped for all sequences. The chromatographic column was a 150×4.6 mm Aquasil C18 column with 3 µm packing (Thermo Scientific). The column temperature was set to 40° C., and the detector wavelength was 280 nm with a bandwidth of 8 nm. The injection volume was 15 µL. Mobile phase A was 0.1% TFA in Water, and mobile phase B was 0.1% TFA in Acetonitrile. The flow rate used was 0.5 L/minute. Mobile phases were filtered and degassed through a 0.45 µm nylon filter under vacuum prior to use, except for Mobile phase A used in sequence file 554410 due to time constraints.

| Gradient Table | | |
|---|---|---|
| Time (min) | % A | % B |
| 0 | 95 | 5 |
| 2 | 95 | 5 |
| 38 | 10 | 90 |
| 43 | 10 | 90 |
| 43.01 | 95 | 5 |
| 60 | 95 | 5 |

X-Ray Powder Diffraction (XRPD): Figures of XRPD patterns were generated using Pattern Match 2.3.6. XRPD patterns were collected with either PANalytical or Bruker.

PANalytical: XRPD patterns were collected with a PANalytical X'Pert PRO MPD diffractometer either in reflection or transmission geometry. For reflection geometry, the diffractometer was configured using the symmetric Bragg-Brentano geometry and the incident beam of Cu-Kα radiation was produced using a long, fine-focus source and a nickel filter. A specimen of the sample was prepared as a thin, circular layer centered on a silicon zero-background substrate. Antiscatter slits (SS) were used to minimize the background generated by air. In transmission geometry, the diffractometer used an incident beam of Cu radiation produced using an Optix long, fine-focus source. An elliptically graded multilayer mirror was used to focus Cu-Kα X-rays through the specimen and onto the detector. A specimen of the sample was sandwiched between 3-µm-thick films and analyzed in transmission geometry. A beam-stop, short antiscatter extension, and antiscatter knife edge, were used to minimize the background generated by air. Transmission configuration was used most frequently throughout this study. For either configuration, prior to the analysis, a silicon specimen (NIST SRM 640d) was analyzed to verify the Si 111 peak position. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Bruker: XRPD patterns were collected using a Bruker D8 DISCOVER diffractometer and Bruker's General Area-Detector Diffraction System (GADDS, v. 4.1.20). An incident microbeam of Cu-Kα radiation was produced using a long, fine-focus tube (40 kV, 40 mA), a parabolically graded multilayer mirror, and a 0.5 mm double-pinhole collimator. Prior to the analysis, a silicon specimen (NIST SRM 640c embedded in epoxy) was analyzed to verify the observed position of the Si 111 peak is consistent with the NIST-certified position. The samples were positioned for analysis by securing the well plate to a translation stage and moving each sample to intersect the incident beam in transmission geometry. The incident beam was scanned and rastered during the analysis to optimize orientation statistics. A beam-stop was used to minimize the background from air. Diffraction patterns were collected using a HISTAR™ area detector located 15 cm from the sample and processed using GADDS. The intensity in the GADDS image of the diffraction pattern was integrated and displayed as a function of 2θ. The instrument was operated under non-GMP conditions, and the results are non-GMP.

Example 1

Microscale Cocrystal Formation of MLN4924

A cocrystal formation of MLN4924 was performed using twenty-five coformers including acetic acid, benzoic acid, camphoric acid, caproic acid, trans-cinnamic acid, ethylenediamine, fumaric acid, gentisic acid, D-glucuronic acid, glycolic acid, hippuric acid, DL-lactic acid, L-lysine, L-malic acid, malonic acid, DL-mandelic acid, meglumine, orotic acid, oxalic acid, piperazine, L-proline, L-pyroglutamic acid, saccharin, succinic acid, and vanillin. Crystallization techniques included evaporation, precipitation using an anti-solvent, slow cooling, vapor diffusion, slurrying, and liquid-assisted grinding. MLN4924 was used as starting material for the cocrystal formation experiments. XRPD data of isolated solids were compared to the pattern of MLN4924 free base, to each other, and to the patterns of respective coformers which are solid at ambient temperature.

Cocrystal formation experiments were first conducted on microscale in a 96-well plate to test a variety of coformers, solvents, and stoichiometries. Coformers used for these experiments included acetic acid, benzoic acid, camphoric acid, caproic acid, trans-cinnamic acid, ethylenediamine, fumaric acid, D-glucuronic acid, glycolic acid, hippuric acid, DL-lactic acid, L-lysine, L-malic acid, DL-mandelic acid, piperazine, L-proline, L-pyroglutamic acid, saccharin, succinic acid, and vanillin. Mole ratios studied varied between 1:1 and 2:1 MLN4924 free base to coformer. Evaporation of the initial solvent system resulted in oily material or glassy films; therefore a second solvent system was added (ethyl acetate:ethanol (90:10)) followed by sonication. Evaporation following this step resulted in an increase in observed crystallinity based on XRPD results.

TABLE 17

Cocrystal Formation of MLN4924

| Well | Coformer(s) | Solvent$^{a,b}$ | Mole Ratio$^c$ | Results |
|---|---|---|---|---|
| A1 | Acetic acid | MeOH:acetone:EtOAc 40:40:40 | 1:1 | Free base |
| A2 | Benzoic acid | MeOH:acetone:EtOAc 40:40:40 | 1:1 | Free base |
| A3 | Camphoric acid | MeOH:acetone:EtOAc 40:40:40 | 1:1 | amorphous |
| A4 | Caproic acid | MeOH:acetone:EtOAc 40:40:40 | 1:1 | amorphous |
| A5 | trans-Cinnamic acid | MeOH:acetone:EtOAc 40:40:40 | 1:1 | amorphous |
| A6 | Fumaric acid | MeOH:acetone:EtOAc 40:40:40 | 1:1 | Halo + fumaric acid peak |
| A7 | Fumaric acid | MeOH:acetone:EtOAc 40:80:40 | 2:1 | Free base |
| A8 | D-glucuronic acid | MeOH$^d$:acetone:EtOAc 40:40:40 | 1:1 | amorphous |
| A9 | Glycolic acid | MeOH$^d$:acetone:EtOAc 40:40:40 | 1:1 | Form A |
| A10 | Hippuric acid | MeOH:acetone:EtOAc 40:40:40 | 1:1 | Form B |
| A11 | DL-lactic acid | MeOH:acetone:EtOAc 40:40:40 | 1:1 | amorphous |
| A12 | L-malic acid | MeOH:acetone:EtOAc 40:40:40 | 1:1 | amorphous |
| B1 | Acetic acid | MeOH:MeOH:IPE 40:40:40 | 1:1 | Free base |
| B2 | Benzoic acid | MeOH:MeOH:IPE 40:40:40 | 1:1 | amorphous |
| B3 | Camphoric acid | MeOH:MeOH:IPE 40:40:40 | 1:1 | amorphous |
| B4 | Caproic acid | MeOH:MeOH:IPE 40:40:40 | 1:1 | Free base |
| B5 | trans-Cinnamic acid | MeOH:MeOH:IPE 40:40:40 | 1:1 | amorphous |
| B6 | Fumaric acid | MeOH:MeOH:IPE 40:40:40 | 1:1 | Halo + fumaric acid peak |
| B7 | Fumaric acid | MeOH:MeOH:IPE 40:80:40 | 2:1 | amorphous |
| B8 | D-glucuronic acid | MeOH$^d$:MeOH:IPE 40:40:40 | 1:1 | amorphous |
| B9 | Glycolic acid | MeOH$^d$:MeOH:IPE 40:40:40 | 1:1 | amorphous |
| B10 | Hippuric acid | MeOH:MeOH:IPE 40:40:40 | 1:1 | Form B |
| B11 | DL-lactic acid | MeOH:MeOH:IPE 40:40:40 | 1:1 | amorphous |
| B12 | L-malic acid | MeOH:MeOH:IPE 40:40:40 | 1:1 | amorphous |
| C1 | Acetic acid | MeOH:HFIPA:toluene 40:40:40 | 1:1 | amorphous |
| C2 | Benzoic acid | MeOH:HFIPA:toluene 40:40:40 | 1:1 | amorphous |
| C3 | Camphoric acid | MeOH:HFIPA:toluene 40:40:40 | 1:1 | amorphous |

TABLE 17-continued

Cocrystal Formation of MLN4924

| Well | Coformer(s) | Solvent[a,b] | Mole Ratio[c] | Results |
|---|---|---|---|---|
| C4 | Caproic acid | MeOH:HFIPA:toluene 40:40:40 | 1:1 | amorphous |
| C5 | trans-Cinnamic acid | MeOH:HFIPA:toluene 40:40:40 | 1:1 | amorphous |
| C6 | Fumaric acid | MeOH:HFIPA:toluene 40:40:40 | 1:1 | amorphous |
| C7 | Fumaric acid | MeOH:HFIPA:toluene 40:80:40 | 2:1 | amorphous |
| C8 | D-glucuronic acid | MeOH[d]:HFIPA:toluene 40:40:40 | 1:1 | amorphous |
| C9 | Glycolic acid | MeOH[d]:HFIPA:toluene 40:40:40 | 1:1 | Form C |
| C10 | Hippuric acid | MeOH:HFIPA:water 40:40:40 | 1:1 | Form B |
| C11 | DL-lactic acid | MeOH:HFIPA:water 40:40:40 | 1:1 | amorphous |
| C12 | L-malic acid | MeOH:HFIPA:water 40:40:40 | 1:1 | amorphous |
| D1 | Acetic acid | MeOH:THF:heptane 40:40:40 | 1:1 | amorphous |
| D2 | Benzoic acid | MeOH:THF:heptane 40:40:40 | 1:1 | amorphous |
| D3 | Camphoric acid | MeOH:THF:heptane 40:40:40 | 1:1 | amorphous |
| D4 | Caproic acid | MeOH:THF:heptane 40:40:40 | 1:1 | amorphous |
| D5 | trans-Cinnamic acid | MeOH:THF:heptane 40:40:40 | 1:1 | amorphous |
| D6 | Fumaric acid | MeOH:THF:heptane 40:40:40 | 1:1 | Halo + fumaric acid peak |
| D7 | Fumaric acid | MeOH:THF:heptane 40:80:40 | 2:1 | amorphous |
| D8 | D-glucuronic acid | MeOH[d]:THF:heptane 40:40:40 | 1:1 | amorphous |
| D9 | Glycolic acid | MeOH[d]:THF:heptane 40:40:40 | 1:1 | amorphous |
| D10 | Hippuric acid | MeOH:THF:heptane 40:40:40 | 1:1 | Form B |
| D11 | DL-lactic acid | MeOH:THF:heptane 40:40:40 | 1:1 | amorphous |
| D12 | L-malic acid | MeOH:THF:heptane 40:40:40 | 1:1 | amorphous |
| E1 | L-malic acid | MeOH:acetone:EtOAc 40:80:40 | 2:1 | Free base |
| E2 | DL-mandelic acid | MeOH:acetone:EtOAc 40:40:40 | 1:1 | amorphous |
| E3 | DL-mandelic acid | MeOH:acetone:EtOAc 40:80:40 | 2:1 | Few new peaks |
| E4 | L-pyroglutamic acid | MeOH:acetone:EtOAc 40:40:40 | 1:1 | amorphous |
| E5 | Succinic acid | MeOH:acetone:EtOAc 40:40:40 | 1:1 | Halo + succinic acid peaks |
| E6 | Succinic acid | MeOH:acetone:EtOAc 40:80:40 | 2:1 | Free base |
| E7 | Ethylenediamine | MeOH:acetone:EtOAc 40:40:40 | 1:1 | Free base |
| E8 | L-lysine | MeOH[d]:acetone:EtOAc 40:40:40 | 1:1 | Free base + L-lysine + few new peaks |
| E9 | L-proline | MeOH[d]:acetone:EtOAc 40:40:40 | 1:1 | Form D |
| E10 | Piperazine | MeOH:acetone:EtOAc 40:80:40 | 2:1 | Free base |
| E11 | Saccharin | MeOH:acetone:EtOAc 40:40:40 | 1:1 | Form E + free base |
| E12 | Vanillin | MeOH:acetone:EtOAc 40:40:40 | 1:1 | Free base |
| F1 | L-malic acid | MeOH:MeOH:IPE 40:80:40 | 2:1 | amorphous |
| F2 | DL-mandelic acid | MeOH:MeOH:IPE 40:40:40 | 1:1 | amorphous |
| F3 | DL-mandelic acid | MeOH:MeOH:IPE 40:80:40 | 2:1 | Free base |
| F4 | L-pyroglutamic acid | MeOH:MeOH:IPE 40:40:40 | 1:1 | amorphous |

TABLE 17-continued

Cocrystal Formation of MLN4924

| Well | Coformer(s) | Solvent[a,b] | Mole Ratio[c] | Results |
|---|---|---|---|---|
| F5 | Succinic acid | MeOH:MeOH:IPE 40:40:40 | 1:1 | Halo + succinic acid peaks |
| F6 | Succinic acid | MeOH:MeOH:IPE 40:80:40 | 2:1 | Free base |
| F7 | Ethylenediamine | MeOH:MeOH:IPE 40:40:40 | 1:1 | Free base |
| F8 | L-lysine | MeOH[d]:MeOH:IPE 40:40:40 | 1:1 | Free base + L-lysine |
| F9 | L-proline | MeOH[d]:MeOH:IPE 40:40:40 | 1:1 | Free base + L-proline + Form D |
| F10 | Piperazine | MeOH:MeOH:IPE 40:80:40 | 2:1 | Free base |
| F11 | Saccharin | MeOH:MeOH:IPE 40:40:40 | 1:1 | amorphous |
| F12 | Vanillin | MeOH:MeOH:IPE 40:40:40 | 1:1 | Free base |
| G1 | L-malic acid | MeOH:HFIPA:toluene 40:80:40 | 2:1 | amorphous |
| G2 | DL-mandelic acid | MeOH:HFIPA:toluene 40:40:40 | 1:1 | amorphous |
| G3 | DL-mandelic acid | MeOH:HFIPA:toluene 40:80:40 | 2:1 | amorphous |
| G4 | L-pyroglutamic acid | MeOH:HFIPA:toluene 40:40:40 | 1:1 | amorphous |
| G5 | Succinic acid | MeOH:HFIPA:toluene 40:40:40 | 1:1 | amorphous |
| G6 | Succinic acid | MeOH:HFIPA:toluene 40:80:40 | 2:1 | amorphous |
| G7 | Ethylenediamine | MeOH:HFIPA:toluene 40:40:40 | 1:1 | amorphous |
| G8 | L-lysine | MeOH[d]:HFIPA:toluene 40:40:40 | 1:1 | Free base + L-lysine + few new peaks |
| G9 | L-proline | MeOH[d]:HFIPA:toluene 40:40:40 | 1:1 | Form D |
| G10 | Piperazine | MeOH:HFIPA:water 40:80:40 | 2:1 | Free base |
| G11 | Saccharin | MeOH:HFIPA:water 40:40:40 | 1:1 | amorphous |
| G12 | Vanillin | MeOH:HFIPA:water 40:40:40 | 1:1 | amorphous |
| H1 | L-malic acid | MeOH:THF:heptane 40:80:40 | 2:1 | amorphous |
| H2 | DL-mandelic acid | MeOH:THF:heptane 40:40:40 | 1:1 | amorphous |
| H3 | DL-mandelic acid | MeOH:THF:heptane 40:80:40 | 2:1 | Free base |
| H4 | L-pyroglutamic acid | MeOH:THF:heptane 40:40:40 | 1:1 | amorphous |
| H5 | Succinic acid | MeOH:THF:heptane 40:40:40 | 1:1 | Halo + succinic acid peaks |
| H6 | Succinic acid | MeOH:THF:heptane 40:80:40 | 2:1 | amorphous |
| H7 | Ethylenediamine | MeOH:THF:heptane 40:40:40 | 1:1 | Few new peaks |
| H8 | L-lysine | MeOH[d]:THF:heptane 40:40:40 | 1:1 | Free base + L-lysine |
| H9 | L-proline | MeOH[d]:THF:heptane 40:40:40 | 1:1 | Form D |
| H10 | Piperazine | MeOH:THF:heptane 40:80:40 | 2:1 | amorphous |
| H11 | Saccharin | MeOH:THF:heptane 40:40:40 | 1:1 | amorphous |
| H12 | Blank | — | — | — |

[a]X/Y/Z x/y/z: x μL of ~0.1M solution of coformer in solvent X + y μL of ~45 mg/mL solution of MLN4924 in solvent Y + z μL of solvent Z
[b]Microplate wells were initially slowly evaporated. The majority of wells resulted in oily material or films. 100 μL of 90:10 EtOAc:EtOH was added to each well, followed by sonication. The solvent was then allowed to evaporate slowly again.
[c]Approximate molar ratio of MLN4924:coformer(s)
[d]Indicates additional water was added to solubilize coformer. ~3:1 MeOH:water ratio was used.

Example 2

Medium Scale Cocrystal Formation of MLN4924

Medium scale experiments then followed which allowed for a wider range of experimental techniques to be employed (Table 18). Isolated solids which exhibited a unique XRPD pattern were further characterized by proton spectroscopy to determine chemical composition and stoichiometry. Thermal analysis were conducted on selected solids.

Overall, sixty single or multi-step medium scale (~50 mg to ~200 mg) experiments were performed targeting various cocrystals of MLN4924 free base. Twenty coformers were studied including mono-, di-, and aromatic carboxylic acids (acetic acid, benzoic acid, trans-cinnamic acid, fumaric acid, gentisic acid, D-glucuronic acid, glycolic acid, hippuric acid, malonic acid, DL-mandelic acid, orotic acid, oxalic acid, L-pyroglutamic acid, and succinic acid), bases (ethylenediamine, meglumine, and piperazine), amino acids (L-lysine and L-proline), and saccharin. Crystallization techniques included evaporation, cooling, vapor diffusion, precipitation with an anti-solvent, slurrying, and liquid assisted grinding. The majority of experiments were conducted using a 1:1, 2:1, or 1:2 molar ratio of MLN4924 to coformer. A few experiments were done such that a large molar excess of one of the components was present (either MLN4924 or coformer), a technique that is designed to reduce the solubility of a potential cocrystal in a given medium and thus promote its crystallization.

TABLE 18

Cocrystal Formation of MLN4924 at Medium Scale

| Coformer (X:Y)$^a$ | Conditions | Observations | Result |
|---|---|---|---|
| Acetic acid (1:1) | Dissolved API in IPA at ~70° C., added coformer (clear), SC to RT, let stir at RT for ~2 days (clear), kept sample in freezer | Slightly hazy solution, no solids | — |
| Benzoic acid (1:1) | Dissolved API and coformer in acetone, crash precipitate with IPE (solids), let slurry at RT for ~1 day | Opaque aggregates, no b/e | Free base |
| | Dissolved API and coformer in ACN at ~70° C., let stir at ~70° C. for ~30 min, SC to RT, stirred at RT for ~1 day (few solids), kept sample in freezer for ~1 day | Opaque aggregates, no b/e | Free base |
| Benzoic acid (1:7) | Slurried API in coformer solution in chloroform:EtOH (10:1) at RT (clear), added coformer to 1:10 mole ratio, let stir at RT | Clear pale yellow solution | — |
| trans-cinnamic acid (1:1) | Dissolved API and coformer at ~75° C., SC to RT (solids), let stir for ~1 day. | Aggregates and small particles with some b/e | Free base |
| Ethylenediamine (1:1) | Dissolved API and coformer in THF, VD with heptane | Yellow, green sticky solids | — |
| | Slurried API and coformer in EtOAc for ~2 days (pale pink solids) | Opaque aggregates, small particles with b/e | Free base |
| | Dissolved API in IPA at ~70° C., added coformer (clear), let stir at ~70° C. for ~30 min, FC to RT, let stir at RT for ~5 hrs (clear), kept sample in refrigerator for ~4 days (clear), kept sample in freezer for ~2 days (solids + sticky substance), added IPE (ppt.), let stir at RT for ~2 days (few solids), kept sample in freezer (few solids), FE | Opaque aggregates, small particles have b/e | Form K + minor free base |
| Fumaric acid (1:1) | Dissolved API and coformer in EtOH at ~66° C., let stir at ~66° C. for ~30 min, SC to RT, let stir at RT for ~2 days (clear), kept sample in freezer | Clear solution | — |
| | Dissolved API and coformer in ACN at ~70° C., let stir at ~70° C. for ~30 min, SC to RT, stirred at RT for ~1 day (sticky solids), kept sample in freezer for ~1 day (sticky solids), added IPE, kept sample in freezer for ~7 days (sticky solids), FE | Sticky film | — |
| | Slurried API and coformer in EtOH at RT for ~3 days | Opaque aggregates, no b/e | Free base |
| Gentisic acid (1:1) | Slurried API in IPA solution of coformer at RT for ~8 days | Opaque aggregates, no b/e | Free base |
| | Dissolved API and coformer in nitromethane:EtOH (30:1) at ~70° C., SC to RT, let stir at RT for ~2 days (thick gel), sonicated (no change), kept sample in sub-ambient conditions for ~14 days (gel-like solids), air dried for ~3 hrs after filtration | Aggregates, broken chunks, some with b/e | Form H (disordered) |

TABLE 18-continued

Cocrystal Formation of MLN4924 at Medium Scale

| Coformer (X:Y)[a] | Conditions | Observations | Result |
|---|---|---|---|
| | Dissolved API and coformer in CAN at ~72° C., let stir at ~72° C. for ~15 min, SC to RT, let stir at RT for ~2 days (thick slurry), added more ACN to loosen solids for filtration, let stir at RT for ~30 min | Opaque aggregates, minor b/e | Form J |
| | From 4922-99-01 (LIMS 302521), VO at ~38° C. for ~1 day | Aggregates, some b/e | Form L (disordered) |
| | Dissolved API and coformer in IPA at ~72° C., SC to RT, stirred for ~1 day (clear), partial FE (clear), kept sample in freezer for ~3 days (clear solution), added heptane (hazy solution), kept sample in freezer (gel-like solids present), attempted VF (very wet solids), let air dry | Aggregates, few short needles, B/E | Form N (disordered) + possible gentisic acid |
| D-glucuronic acid (1:1) | SC in MeOH:water (10:1) from ~56° C. to RT, let stir at RT for ~1 day (clear), kept sample in refrigerator (clear), kept in freezer | Clear solution | — |
| | Grinding with EtOH, 2-10 minute cycles at 30 Hz (scraping and repacking solids in between) | — | Free base + D-glucuronic acid |
| Glycolic acid (1:1) | Slurried API in EtOAc at ~72° C., added coformer (solids remained), let stir at ~72° C. for ~30 min (solids moved to solvent level along vial walls), SC to RT, let stir at RT for ~3 days | Opaque aggregates, b/e on edges | Free base |
| | Slurried API and coformer in isopropyl acetate at RT for ~2 days | Opaque aggregates, few small particles have b/e | Form A + minor free base |
| | Dissolved API and coformer in acetone, VD with MTBE at RT | Broken chunks, some b/e | Form A |
| Glycolic acid (1:2) | Slurried API and coformer in isopropyl acetate at ~38° C. for ~2 days (solids along vial walls), sonicated, let stir at RT for ~30 min | Opaque aggregates, few small particles have b/e | Form A |
| Glycolic acid (2:1) | Dissolved API and coformer in EtOAc:EtOH (4:1) at ~72° C., let stir at ~72° C. for ~30 min, SC to RT, let stir at RT for ~5 days (clear), FE | Oily film | — |
| Glycolic acid (1:7) | Slurried API in coformer solution in CAN (clear), continued stirring at RT (clear), added coformer to 1:10 mole ratio | Clear dark yellow solution | — |
| Hippuric acid (1:1) | Slurried coformer in API solution in p- dioxane at RT for ~3 days (solids of coformer remained), added EtOH, continued stirring at RT for ~1 day (clear), kept sample in freezer for ~2 days (frozen), let come to RT (clear), added heptane (gum and hazy solution), let stir at RT for ~1 day | Opaque aggregates, no b/e | Form B |
| | Dissolved API and coformer in MeOH, VD with MTBE | Clear solution | — |
| | Grinding with IPA, 2-10 minute cycles at 25 Hz (scraping and repacking solids in between) | Opaque aggregates, small particles with some b/e | Free base + hippuric acid |
| Hippuric acid (5:1) | Slurried coformer in API solution in acetone (clear), continued stirring at RT | Clear yellow solution | — |
| L-lysine (1:1) | Slurried API and coformer in IPA:MeOH (10:1) at RT for ~4 days | Opaque aggregates, minor b/e | Free base + L-lysine |
| | SE in acetone:MeOH:H₂O:EtOAc | Irregular fragments, some b/e | Free base + L-lysine + few new peaks |
| | FE in THF:MeOH:H₂O:heptane | Aggregates, some b/e | Form K + minor free base |

TABLE 18-continued

Cocrystal Formation of MLN4924 at Medium Scale

| Coformer (X:Y)[a] | Conditions | Observations | Result |
|---|---|---|---|
| Malonic acid (1:1) | Attempted to dissolve API and coformer in nitromethane at ~85° C. (dissolution followed by ppt), SC to RT, let stir at RT for ~1 day | Opaque aggregates, some b/e | Form M |
| DL-mandelic acid (1:1) | Dissolved API and coformer in ACN at ~70° C., let stir at ~70° C. for ~30 min, SC to RT, let stir at RT for ~5 hrs (clear), kept sample in refrigerator for ~4 days (clear), kept sample in freezer for ~2 days (clear), added IPE (ppt., turned oily), let stir at RT for ~2 days (solids mainly along vial walls), sonicated to loosen solids | Aggregates, small particles have b/e | Free base |
|  | Dissolved API and coformer in isopropyl acetate:EtOH (5:1) at ~73° C., SC to RT, let stir at RT for ~1 day (clear), kept sample in freezer ~1 day (clear), SE (oily film), triturate with EtOAc, sonicated (hazy solution), kept sample in freezer for ~4 days (hazy solution), added heptane (ppt followed by formation of one large clump), FE | Sticky clear film | — |
| Meglumine (1:1) | Slurried API and coformer in EtOH for ~1 day | Aggregates, tiny particles, no b/e | Free base + meglumine |
|  | Dissolved API and coformer in ACN:EtOH (2:1) at ~70° C., let stir at ~70° C. for ~30 min, SC to RT, stirred at RT for ~2 days | Aggregates, thin needles, some b/e | Meglumine |
| Orotic acid (1:1) | Grinding with ACN, 2-10 minute cycles at 30 Hz (scraping and repacking solids in between) | — | Free base + orotic acid (disordered) |
|  | Slurried coformer in MeOH solution of API at ~38° C. for ~2 days, let cool to RT | Opaque aggregates, no b/e | Orotic acid |
| Oxalic acid (1:1) | Dissolved API and coformer in nitromethane at ~85° C., SC to RT (gummy solids), added MTBE (no change), kept sample in freezer for ~1 day (sticky solids), decanted solvent, dried solids with $N_2$ stream (still tacky) | Appeared to deliquesce at ambient RH | — |
| Piperazine (1:1) | Slurried API and coformer in EtOH at RT for ~2 days | Opaque aggregates, few small particles have b/e | Free base |
|  | Dissolved API and coformer in ACN at ~72° C., let stir at ~72° C. for ~30 min, SC to RT, let stir at RT for ~1 day | Opaque aggregates, broken fragments, no b/e | Form G |
|  | From 4922-63-01 (LIMS 301164), VO at ~38° C. for ~1 day | Aggregates, no b/e | Form G (slightly disordered) |
| Piperazine (2:1) | Dissolved API and coformer in EtOAc:EtOH (~13:1) at ~70° C., SC to RT, let stir at RT for ~5 hrs (clear), kept sample in refrigerator for ~4 days (clear), kept sample in freezer (few solids), FE | Sticky film | — |
|  | Dissolved API and coformer in IPA at ~72° C., SC to RT, stirred ~1 day (clear), partial FE (slightly hazy), kept in freezer for ~3 days (slightly hazy solution), added MTBE (no change), kept sample in freezer (few solids), partial FE at RT (solids) | Aggregates, b/e on edges, b/e on small particles | Free base |
| L-proline (1:1) | Grinding with EtOH, 2-10 minute cycles at 30 Hz (scraping and repacking solids in between) | — | Free base + L-proline |
|  | Slurried coformer in API solution in MeOH (clear after ~30 min, remained clear after ~2 hrs), kept sample in refrigerator (clear), added IPE (clear), SE (slightly tacky solids), VO at RT for ~1 day | Irregular fragments, opaque aggregates, b/e | Free base + L-proline |

TABLE 18-continued

Cocrystal Formation of MLN4924 at Medium Scale

| Coformer (X:Y)[a] | Conditions | Observations | Result |
|---|---|---|---|
| | Dissolved API and coformer in IPA:MeOH (10:1) at ~72° C., let stir at ~72° C. for ~15 min, SC to RT, let stir at RT for ~5 days (some solids), kept sample in freezer for ~4 days | Aggregates, b/e on edges | L-proline (anhydrous + monohydrate) |
| | SE in acetone:MeOH:water:EtOAc (slightly tacky solids), VO at RT for ~1 day | Aggregates, small particles with b/e | Free base + L-proline + Form D |
| | FE in THF:MeOH:water:heptane (slightly tacky solids), VO at RT for ~1 day | Aggregates, some b/e | Form D |
| | Dissolved API and coformer in acetone:water (~7:1) at ~50° C., FC to RT, let stir at RT for ~1 day (slightly hazy solution), kept sample in refrigerator | Clear solution | — |
| L-pyroglutamic acid (1:1) | Slurried coformer in THF solution of API (clear), kept sample in freezer | Clear yellow solution | — |
| | Slurried API and coformer in IPA at RT for ~2 days | Opaque aggregates, some smaller particles have b/e | Free base |
| | Attempted to dissolve API and coformer in EtOAc at ~75° C. (some dissolution observed, solids crept up along sides of vial, let stir at ~75° C. for ~20 min (solids remained), FC to RT, let stir at RT for ~1 day | Small aggregates, b/e | Free base + pyroglutamic acid |
| Saccharin (1:1) | Grinding with IPA, 1-10 minute cycle at 30 Hz (tacky solids), air dried ~3 days | — | Free base + saccharin + Form F |
| | Slurried API in EtOAc at ~72° C., added coformer (partial dissolution observed, large clump of solids formed), let stir at ~72° C. for ~30 min (large clump loosened into solids), SC to RT, let stir at RT for ~3 days | Opaque aggregates, minor b/e | Form F |
| | Slurried API and coformer in EtOH at RT (partial dissolution, followed by ppt), let stir at RT for ~2 days | Opaque aggregates, few small particles have b/e | Form F |
| Succinic acid (1:1) | Slurried API and coformer in EtOAc for ~1 day | Aggregates with small particles, some b/e | Free base + succinic acid |
| | Dissolved API and coformer in ACN at ~70° C., let stir at ~70° C. for ~30 min, SC to RT, stirred at RT for ~1 day (few solids), kept sample in freezer for ~1 day | Small aggregates, tiny particles have b/e | Free base (slightly shifted) |

[a]X:Y = approximate molar ratio of API:coformer
[b]Non-cGMP sample

Cocrystal Form A was observed from slurrying in isopropyl acetate and from vapor diffusion between acetone and methyl tert-butyl ether. The XRPD pattern of cocrystal Form A (FIG. 1) was successfully indexed indicating the presence of a single crystalline phase. Agreement between the allowed peak positions and the observed peaks indicates a consistent unit cell determination. Proton NMR data for cocrystal Form A (FIG. 2) are consistent with MLN4924 containing approximately one mole of glycolic acid per mole of MLN4924. Thermogravimetric data for cocrystal Form A (FIG. 4) show an about 5.3 wt % loss between about 101° C. and about 175° C. possibly related to the endothermic event as seen in the DSC thermogram and a sharp weight loss at about 216° C., possibly attributed to decomposition. The DSC thermogram (FIG. 3) shows a minor endothermic peak at about 121.3° C. followed immediately by a sharp endothermic peak at about 138.1° C. (peak maximum), likely attributed to volatilization and decomposition or the material melting.

Cocrystal Form B was observed from only one attempt targeting a hippuric acid cocrystal. This material observed at medium scale is the same as that observed at microscale, based on XRPD results. Cocrystal Form B was isolated from a multi-step experiment involving precipitation of a p-dioxane:ethanol (5:1) solution containing the API and coformer with heptane. A gummy, hazy solution resulted immediately upon antisolvent addition, but slurrying at ambient temperature for one day resulted in handleable solids for isolation. The XRPD pattern of cocrystal Form B (FIG. 5) was indexed with two possible solutions indicating either the presence of a single crystalline phase (monoclinic—red bars) or, more likely, a mixture of a single crystalline phase with free hippuric acid (orthorhombic—blue bars). Proton NMR data (FIG. 6) are consistent with MLN4924 containing approximately one mole of hippuric acid per mole of API. Thermogravimetric data for cocrystal Form B show negligible weight loss prior to the sharp weight loss at about 235° C., suggesting the material is anhydrous and unsolvated (FIG. 8). The DSC thermogram shows a sharp endothermic peak at about 150.9° C. (peak maximum), possibly attributed to the material melting followed by possible decomposition (FIG. 7).

Cocrystal Form D was observed from an attempt targeting an L-proline cocrystal from a slow evaporation experiment in acetone:MeOH:water:EtOAc. This same XRPD pattern (FIG. 10) was observed from all four microscale experiments also targeting an L-proline cocrystal. Proton NMR data (FIG. 11) indicate the presence of ~0.3 moles of L-proline per mole of MLN4924.

Cocrystal Form F was observed from two experiments targeting a saccharin cocrystal. An attempted cooling experiment in ethyl acetate and an ambient temperature slurry in ethanol both resulted in cocrystal Form F. Liquid assisted grinding with isopropyl alcohol resulted in cocrystal Form F as a mixed phase with both starting materials. The following phase and composition data are sufficient to designate this material as cocrystal Form F. The XRPD pattern of cocrystal Form F (FIG. 12) was successfully indexed indicating the presence of a single crystalline phase. Agreement between the allowed peak positions, marked with red bars, and the observed peaks indicates a consistent unit cell determination. Proton NMR data for cocrystal Form F (FIG. 13) are consistent with MLN4924 containing approximately one mole of saccharin per mole of API. Thermogravimetric data show a stepwise about 1.9 wt % loss between about 171° C. and about 200° C. and a sharp weight loss at about 219° C. likely associated with decomposition of the material (FIG. 15). The DSC thermogram shows a sharp endothermic peak at about 198.5° C. overlapping with a sharp exothermic peak at about 201.8° C., possibly attributed to a melt/decomposition event (FIG. 14).

Cocrystal Form G was observed while targeting a piperazine cocrystal from a slow cooling experiment in acetonitrile. The XRPD pattern of cocrystal Form G (FIG. 16) was successfully indexed indicating the presence of a single crystalline phase. Agreement between the allowed peak positions, marked with red bars, and the observed peaks indicates a consistent unit cell determination. The predicted unit cell volume based from the indexing results suggests a stoichiometry of either a 1:1 MLN4924:piperazine cocrystal or a 1:2 MLN4924:acetonitrile solvate. Proton NMR data of cocrystal Form G (FIG. 17) were consistent with MLN4924 containing approximately 0.5 moles of piperazine and approximately 0.6 moles of acetonitrile per mole of API. Drying cocrystal Form G under vacuum at ~38° C. for ~1 day resulted in material exhibiting a similar XRPD pattern, but more representative of disordered material based on peak broadening.

Cocrystal Form J was observed from a cooling experiment in acetonitrile, and although the material is highly crystalline based on XRPD results (FIG. 20), the proton NMR data (FIG. 21) indicate the presence of approximately one mole of gentisic acid and three moles of acetonitrile per mole of MLN4924. Drying cocrystal Form J under vacuum to remove the acetonitrile resulted in a disordered material, identified as Form L. Only residual levels of acetonitrile were detected in the proton NMR data of Form L. Two other materials (designated as Form H and Form N), exhibiting broadened peaks in the XRPD pattern, indicative of disordered material, were observed from crystallization attempts in nitromethane:ethanol (~30:1) and isopropyl alcohol:heptane (~4:1).

Cocrystal Form M was observed from one sample targeting a malonic acid cocrystal. Cocrystal Form M was prepared by an attempted slow cooling experiment in nitromethane. Partial dissolution of the starting materials followed by precipitation was observed and the sample was allowed to cool slowly to ambient temperature prior to isolation. The XRPD pattern of Form M (FIG. 22) was successfully indexed indicating the presence of a single crystalline phase. Agreement between the allowed peak positions, marked with red bars, and the observed peaks indicates a consistent unit cell determination. Proton NMR data (FIG. 23) are consistent with MLN4924 containing approximately one mole of malonic acid per mole of API. Thermogravimetric data of cocrystal Form M (FIG. 25) show a stepwise about 14.0 wt % loss between about 135° C. and about 184° C. potentially due to the loss of malonic acid. A sharp weight loss at about 254° C. is also observed and likely attributable to decomposition of the material (FIG. 24). The DSC thermogram shows a sharp endotherm at about 155.1° C. (peak maximum) possibly attributed to volatilization and decomposition or the material melting.

Other Forms Observed During the Formation Experiment: A new material, designated as Form K, was isolated as a mixture with a small amount of MLN4924 free base from select experiments with ethylenediamine and L-lysine. Proton NMR data of Form K from both cocrystal experiments indicate that ethylenediamine and L-lysine are not present or only at residual levels, indicating they are not cocrystals. Although the proton NMR data are consistent with the chemical structure of MLN4924, an increase in small unknown peaks was observed, suggesting an increase in impurities. This result suggests the possibility that Form K is a polymorph of MLN4924 which may be related to the basic conditions and/or level of impurities that resulted from these experimental conditions.

Example 3

Preliminary Evaluation of Selected MLN4924 Cocrystals

The aqueous solubility of new materials was estimated in water using a solvent addition method (Table 19). All new materials that were confirmed to contain a stoichiometric ratio of MLN4924 to coformer were estimated to have a solubility of less than 1 mg/mL.

TABLE 19

Aqueous Solubility Estimates of MLN4924 Cocrystal Candidates

| Material tested | Coformer | X:Y [a] | Solubility Estimate[b](mg/mL) |
|---|---|---|---|
| Form A | Glycolic acid | 1:1 | <1[c] |
| Form B | Hippuric acid | 1:1 | <1 |
| Form F | Saccharin | 1:1 [d] | <1 |
| Form G | Piperazine | 2:1 | <1 |
| Form H | Gentisic acid | 1:1 [d] | <1 |
| Form J | Gentisic acid | 1:1 | <1 |
| Form L | Gentisic acid | 1:1 | <1 |
| Form M | Malonic acid | 1:1 | <1 |
| Form N | Gentisic acid | 1:1 | <1[c] |

[a] API:coformer stoichiometry as confirmed by proton NMR spectroscopy unless otherwise noted
[b] Values are rounded to nearest whole number. If dissolution did not occur as determined by visual assessment value is reported as "<"
[c] Few solids remained
[d] Ratio reported is from experimental conditions and was not confirmed by proton NMR Each cocrystal was also exposed to elevated relative humidity (first ~75% RH, then ~97% RH) for specified time periods (Table 20). All new materials, except for the solvated piperazine cocrystal (Material G), showed no propensity for deliquescence and remained free flowing solids. The solvated piperazine cocrystal became slightly tacky after exposure to ~97% RH for approximately two days.

TABLE 20

Physical Stability Studies of Selected MLN4924 Cocrystal Candidates

| Material Source | coformer | X:Y [a] | Conditions | Observations After Stress |
|---|---|---|---|---|
| Form A | Glycolic acid | 1:1 | ~75% RH stress, ~3 days, RT | Free flowing solids |
|  |  |  | ~97% RH stress, ~2 days, RT | Free flowing solids |
| Form B | Hippuric acid | 1:1 | ~75% RH stress, ~3 days, RT | Free flowing solids |
|  |  |  | ~97% RH stress, ~2 days, RT | Free flowing solids |
| Form F | Saccharin | 1:1 | ~75% RH stress, ~3 days, RT | Free flowing solids |
|  |  |  | ~97% RH stress, ~2 days, RT | Free flowing solids |
| Form G | Piperazine | 2:1 | ~75% RH stress, ~3 days, RT | Free flowing solids |
|  |  |  | ~97% RH stress, ~2 days, RT | Slightly tacky solids which stick to vial walls |
| Form H | Gentisic acid | 1:1 [b] | ~75% RH stress, ~3 days, RT | Free flowing solids |
|  |  |  | ~97% RH stress, ~2 days, RT | Free flowing solids |
| Form J | Gentisic acid | 1:1 | ~75% RH stress, ~3 days, RT | Free flowing solids |
|  |  |  | ~97% RH stress, ~2 days, RT | Free flowing solids |
| Form L | Gentisic acid | 1:1 | ~75% RH stress, ~4 days, RT | Free flowing solids |
|  |  |  | ~97% RH stress, ~1 day, RT | Free flowing solids |
| Form M | Malonic acid | 1:1 | ~75% RH stress, ~4 days, RT | Free flowing solids |
|  |  |  | ~97% RH stress, ~1 day, RT | Free flowing solids |
| Form N | Gentisic acid | 1:1 | ~75% RH stress, ~4 days, RT | Free flowing solids |
|  |  |  | ~97% RH stress, ~1 day, RT | Free flowing solids |

[a] API:coformer stoichiometry as confirmed by proton NMR spectroscopy unless specified
[b] Stoichiometry as used for the experimental conditions but not confirmed by proton NMR spectroscopy Example 4

Scale Up of Selected MLN4924 Cocrystals

Initial scale-ups were attempted for the glycolic acid, hippuric acid, malonic acid, piperazine, and saccharin cocrystals at about 200-300 mg scale with respect to MLN4924. Experimental details and results are included in Table 21. The first attempt with malonic acid and saccharin resulted in the same materials observed during the medium scale formation experiment. Two attempts to reproduce the piperazine cocrystal at larger scale were unsuccessful; one resulted in the free base and the other resulted in material exhibiting a similar XRPD pattern as Form G, but a few additional peaks were observed. These peaks were not allowed based on the indexing solution of the XRPD pattern of Form G and were not attributed to any known forms of the starting components at the time of this study. An underlying halo was also observed in the XRPD pattern of this material prepared at scale-up, suggesting the presence of disorder or amorphous content. Thermogravimetric data of this sample shows a weight loss of about 5.7% from about 24° C. to about 150° C. (FIG. 19). The DSC thermogram shows several thermal events between about 46° C. and about 166° C. Proton NMR data of this sample was consistent with MLN4924 containing about 0.5 moles of piperazine and about ~0.2 moles of acetonitrile per mole of API. The NMR data suggests that the acetonitrile content of this material may be variable.

TABLE 21

Scale up of Selected MLN4924 Cocrystals

| Targeted Material | Conditions [a] | Observations | Yield | Result |
|---|---|---|---|---|
| Glycolic acid cocrystal (Form A) | Slurried ~300 mg API and coformer (~1:2 API:coformer molar ratio) in isopropyl acetate at ~38° C. for ~2 days, sonicated, let stir at RT for ~1 hr | Aggregates, no distinct morphology, no b/e | — | Minor Form A + free base |
|  | Slurried ~300 mg of API and coformer (~1:1.5 API:coformer | Opaque aggregates, no | 71% | Form A |

TABLE 21-continued

Scale up of Selected MLN4924 Cocrystals

| Targeted Material | Conditions[a] | Observations | Yield | Result |
|---|---|---|---|---|
| | molar ratio) in isopropyl acetate, stir at RT for ~2 days | distinct morphology, no b/e | | |
| Hippuric acid cocrystal (Form B) | Dissolved ~300 mg API and coformer in p-dioxane:EtOH (4:1), added heptane (oily slurry with ppt), stirred at RT for ~2 days (paste-like mass sticking to vial walls), kept in refrigerator for ~3 days (no change), decanted solvent, left for air drying of sticky mass | Aggregates, no distinct morphology, no b/e | — | Free base + hippuric acid |
| | Dissolved ~150 mg of API and coformer in p-dioxane:EtOH (5:1), let stir at RT for ~1 hr (clear), added heptane, immediate ppt and phase separation to an oil phase, let slurry at RT for ~1 day | Opaque aggregates, no distinct morphology, w/ b/e in few small particles | 46% peak | Form B + one unknown |
| | Dissolved ~150 mg of API and coformer in p-dioxane:EtOH (5:1), let stir at RT for ~1 hr (clear), added heptane, immediate ppt and phase separation, let slurry at RT for ~1 day | Opaque aggregates, no distinct morphology, no b/e | 39% | Form B |
| Saccharin cocrystal (Form F) | Slurried ~300 mg API and coformer in EtOH at RT, let stir at RT for ~2 days | Opaque aggregates, no distinct morphology, w/ b/e | 85% | Form F |
| Piperazine cocrystal (Form G) | Dissolved ~240 mg API and coformer (2:1 molar ratio) in ACN at ~71° C., SC to RT, let stir at RT for ~3 days | Very fine opaque particles, no distinct morphology, no b/e | — | Free base |
| | Dissolved ~250 mg API and coformer in ACN at ~71° C., SC to RT, let stir at RT for ~4 days | Opaque aggregates, no distinct morphology, no b/e | — | Form G + peaks |
| Malonic acid cocrystal (Form M) | Attempted to dissolve ~300 mg API and co- former in nitromethane at ~85° C., SC to RT, let stir at RT for ~1 day | Aggregates with no distinct morphology, some b/e | 78% | Form M |

[a] Unless stated, a ~1:1 molar ratio of MLN4924 and respective coformer was used.

Example 5

Physical and Chemical Stability Studies of Selected Cocrystals

The physical and chemical stability of the glycolic acid, hippuric acid, malonic acid, and saccharin cocrystals were evaluated at two stress conditions (60° C./ambient relative humidity and 60° C./75% relative humidity) and compared to MLN4924 HCl salt. These results are summarized in Table 22.

TABLE 22

Relative Humidity/Temperature Stressing of MLN4924 Cocrystals and HCl Salts

| Cocrystal/Salt | Purity T = 0 | 60° C./ambient RH, 2 weeks | 60° C./75% RH, 2 weeks |
|---|---|---|---|
| HCl | 98.2% | 94.6% | 96.6% |
| Glycolic acid (Form A) | 96.9% | 95.9% | 93.0% |
| Hippuric acid (Form B) | 94.4% | 94.1% | 93.9% |
| Saccharin (Form F) | 91.2% | 91.2% | 91.0% |
| Malonic acid (Form M) | 99.0% | 99.1% | 99.0% | a. 60° C./ambient RH, 60° C./75% RH, 2 weeks.
b. Results:
HCl salt changed forms to the hydrate at 60° C./75% RH;
No form changed with the cocrystals.

Physical stability was assessed by comparison of XRPD patterns of the unstressed and stressed samples. No form changes were observed for any of the cocrystals studied. However, the 2-week MLN4924-HCl 60° C./75% RH sample was observed to have a new unique crystalline XRPD pattern suggesting a change in form may have occurred, possibly to a hydrated form.

Chemical stability was assessed via HPLC analysis of samples at t=0 and t=14 days. The initial t=0 data for the glycolic and hippuric acid samples was repeated due to poor agreement between working and check standards. This second run occurred about 1-2 days after the initial samples.

The glycolic acid cocrystal and MLN4924-HCl showed limited stability under the stressed conditions compared to the other samples. Each of these samples showed a loss of at least 3% of API area percent at one of the stressed conditions after two weeks. Of the samples tested, the malonic acid had the highest initial purity and the highest final purity in each of the stress conditions. The saccharin cocrystal had the lowest initial purity (about 91%) but did not show significant changes upon stressing. Specifically, the hippuric acid, saccharin, and malonic acid cocrystals show little decomposition under both stress conditions.

The hippuric acid, saccharin, and malonic acid cocrystals showed improvement in stability over the current MLN4924 HCl form and could be potential alternative forms for development.

Example 6

Scale-Up Preparation of Cocrystal Form A 300.7 mg of MLN4924 and 77.6 mg (about 1.5 molar equivalent) of glycolic acid were weighed out. Added 7 mL of isopropyl acetate by pipette to obtain a suspension of 0.097 M of MLN4924 in isopropyl acetate. The suspension was stirred at room temperature for about 2 days. Solids were isolated via vacuum filtration and air dried at room temperature. Yield was about 71%.

Example 7

Scale-Up Preparation of Cocrystal Form B 151.0 mg of MLN4924 and 61.6 mg (about 1 molar equivalent) of hippuric acid were weighed out. 1.2 mL 5:1 p-dioxane:ethanol was added by pipette to obtain a mixture of 0.28 M of MLN4924 in p-dioxane:ethanol. The mixture was allowed to stir at room temperature for about 1 hour until a clear solution was obtained. 5 mL of heptane (4.2 times of the amount of p-dioxane:ethanol) was added. Precipitation and phase separation was observed upon addition of heptane solution. The mixture was stirred at room temperature for about 1 day when the mixture was observed to be a slurry. Solids were isolated via vacuum filtration and air dried at room temperature. Yield was about 39%.

Example 8

Scale-Up Preparation of Cocrystal Form F 301.4 mg of MLN4924 and 124.8 mg (about 1 molar equivalent) of saccharin were weighed out. 4.5 mL of ethanol was added by pipette to obtain a mixture of 0.15 M MLN4924 in ethanol. The sample was allowed to stir at room temperature for about 1 day. An additional 1 mL of ethanol (22% of the amount of the initially added ethanol) was added and the sample was stirred for about 1 additional day at room temperature. Solids were isolated via vacuum filtration and air dried at room temperature. Yield was about 85%.

Example 9

Medium Scale Preparation of Cocrystal Form G 108.8 mg of MLN4924 and 22.6 mg (about 1 molar equivalent) of piperazine were weighed out. 2 mL of acetonitrile was added by pipette to obtain a mixture of 0.12 M of MLN4924 in acetonitrile. Sample was stirred and heated to about 72° C. in an oil bath and a clear solution was observed. The sample was held at about 72° C. for about 30 minutes before heat was turned off and the sample was allowed to slowly cool to room temperature and stir for about 1 day. A slurry was observed. Solids were isolated via vacuum filtration.

Example 10

Scale-Up Preparation of Cocrystal Form F 299.9 mg of MLN4924 and 70.4 mg (about 1 molar equivalent) of malonic acid were weighed out. 5.5 mL of nitromethane was added by pipette to obtain a mixture of 0.12 M of MLN4924 in nitromethane. Sample was stirred and heated to about 85° C. in an oil bath for about 30 minutes. A slurry was observed. Heat was turned off and the sample was allowed to cool to room temperature and continue stirring for about 1 day. A slurry was observed. Solids were isolated via vacuum filtration and air dried at room temperature. Yield was about 78%.

What is claimed is:

1. A cocrystal of ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulfamate of formula (I) and a coformer:

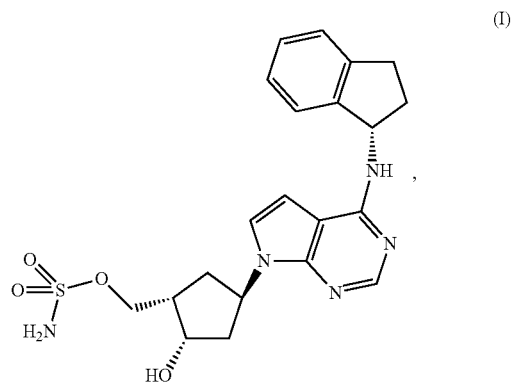 [SMILES: NS(=O)(=O)OC[C@@H]1C[C@@H](n2ccc3c(N[C@H]4CCc5ccccc54)ncnc32)C[C@@H]1O]

wherein the coformer is selected from the group consisting of acetic acid, benzoic acid, camphoric acid, caproic acid, trans-cinnamic acid, ethylenediamine, fumaric acid, gentisic acid, D-glucuronic acid, glycolic acid, hippuric acid, DL-lactic acid, L-lysine, L-malic acid, malonic acid, DL-mandelic acid, meglumine, orotic acid, oxalic acid, piperazine, L-proline, L-pyroglutamic acid, saccharin, succinic acid, and vanillin.

2. The cocrystal of claim 1, wherein the coformer is glycolic acid.

3. The cocrystal of claim 2 which is an anhydrous mono-glycolic acid cocrystal.

4. The cocrystal of claim 3, characterized by an XRPD pattern having peaks at 2θ angles of 8.94°±0.2°, 18.48°±0.2°, and 20.41°±0.2°.

5. The cocrystal of claim 3, characterized by an endothermic peak at about 138.1° C., as determined by differential scanning calorimetry.

6. The cocrystal of claim 3, characterized by an about 5.3 wt % loss between about 101° C. and about 175° C. and a weight loss at about 216° C., as determined by thermal gravimetric analysis.

7. The cocrystal of claim 1, wherein the coformer is hippuric acid.

8. The cocrystal of claim 7 which is an anhydrous mono-hippuric acid cocrystal.

9. The cocrystal of claim 8, characterized by an XRPD pattern having peaks at 2θ angles of 4.05°±0.2°, 19.25°±0.2°, and 22.60°±0.2°.

10. The cocrystal of claim 8, characterized by an endothermic peak at about 150.9° C., as determined by differential scanning calorimetry.

11. The cocrystal of claim 8, characterized by a weight loss at about 235° C., as determined by thermal gravimetric analysis.

12. The cocrystal of claim 1, wherein the coformer is saccharin.

13. The cocrystal of claim 12 which is an anhydrous mono-saccharin cocrystal.

14. The cocrystal of claim 13, characterized by an XRPD pattern having peaks at 2θ angles of 7.86°±0.2°, 15.81°±0.2°, and 17.97°±0.2°.

15. The cocrystal of claim 13, characterized by an endothermic peak at about 198.5° C. overlapping with an exothermic peak at about 201.8° C., as determined by differential scanning calorimetry.

16. The cocrystal of claim 13, characterized by an about 1.9 wt % loss between about 171° C. and about 200° C., as determined by thermal gravimetric analysis.

17. The cocrystal of claim 1, wherein the coformer is malonic acid.

18. The cocrystal of claim 17 which is an anhydrous mono-malonic acid cocrystal.

19. The cocrystal of claim 18, characterized by an XRPD pattern having peaks at 2θ angles of 3.66°±0.2°, 19.24°±0.2°, and 25.14°±0.2°.

20. The cocrystal of claim 18, characterized by an endothermic peak at about 155.1° C., as determined by differential scanning calorimetry.

21. The cocrystal of claim 18, characterized by an about 14.0 wt % loss between about 135° C. and about 184° C., as determined by thermal gravimetric analysis.

22. A pharmaceutical composition comprising any one of the cocrystals of claim 1, and pharmaceutically acceptable carrier or diluent.

* * * * *